US008249329B2

(12) United States Patent
Silver

(10) Patent No.: US 8,249,329 B2
(45) Date of Patent: *Aug. 21, 2012

(54) METHOD AND APPARATUS FOR DETECTING AND CHARACTERIZING AN OBJECT

(75) Inventor: William M Silver, Weston, MA (US)

(73) Assignee: Cognex Technology and Investment Corporation, Mt. View, CA (US)

(*) Notice: Subject to any disclaimer, the term of this patent is extended or adjusted under 35 U.S.C. 154(b) by 807 days.

This patent is subject to a terminal disclaimer.

(21) Appl. No.: 11/136,019

(22) Filed: May 24, 2005

(65) Prior Publication Data

US 2005/0275833 A1 Dec. 15, 2005

Related U.S. Application Data

(63) Continuation of application No. 10/865,155, filed on Jun. 9, 2004.

(51) Int. Cl.
*G06K 9/00* (2006.01)

(52) U.S. Cl. ........ 382/141; 382/151; 382/152; 382/192; 382/232

(58) Field of Classification Search .................. 382/141, 382/151, 152, 192, 232
See application file for complete search history.

(56) References Cited

U.S. PATENT DOCUMENTS

| | | | |
|---|---|---|---|
| 4,214,265 A | 7/1980 | Olesen | |
| 4,384,195 A | 5/1983 | Nosler | |
| 4,647,979 A | 3/1987 | Urata | |
| 4,847,772 A | 7/1989 | Michalopoulos et al. | |
| 4,916,640 A | 4/1990 | Gasperi et al. | |
| 4,962,538 A | 10/1990 | Eppler et al. | |
| 4,972,494 A | 11/1990 | White et al. | |
| 5,018,213 A | 5/1991 | Sikes | |
| 5,040,056 A | 8/1991 | Sager et al. | |
| 5,121,201 A | 6/1992 | Seki | |
| 5,146,510 A | 9/1992 | Cox et al. | |
| 5,164,998 A | 11/1992 | Reinsch | |
| 5,177,420 A | 1/1993 | Wada et al. | |

(Continued)

FOREIGN PATENT DOCUMENTS

DE 10012715 9/2000

(Continued)

OTHER PUBLICATIONS

Chen, Y. H., "Computer Vision for General Purpose Visual Inspection: a Fuzzy Logic Approach", *Optics and Lasers in Engineering 22*, Elsevier Science Limited, vol. 22, No. 3,(1995),pp. 182-192.

(Continued)

*Primary Examiner* — Mike Rahmjoo

(57) ABSTRACT

Disclosed are methods and apparatus for automatic optoelectronic detection and inspection of objects, based on capturing digital images of a two-dimensional field of view in which an object to be detected or inspected may be located, analyzing the images, and making and reporting decisions on the status of the object. Decisions are based on evidence obtained from a plurality of images for which the object is located in the field of view, generally corresponding to a plurality of viewing perspectives. Evidence that an object is located in the field of view is used for detection, and evidence that the object satisfies appropriate inspection criteria is used for inspection. Methods and apparatus are disclosed for capturing and analyzing images at high speed so that multiple viewing perspectives can be obtained for objects in continuous motion.

49 Claims, 26 Drawing Sheets

U.S. PATENT DOCUMENTS

| | | |
|---|---|---|
| 5,184,217 A | 2/1993 | Doering |
| 5,198,650 A | 3/1993 | Wike et al. |
| 5,210,798 A | 5/1993 | Ekchian et al. |
| 5,233,541 A | 8/1993 | Corwin et al. |
| 5,262,626 A | 11/1993 | Goren et al. |
| 5,286,960 A | 2/1994 | Longacre, Jr. et al. |
| 5,298,697 A | 3/1994 | Suzuki et al. |
| 5,317,645 A | 5/1994 | Perozek et al. |
| 5,345,515 A | 9/1994 | Nishi et al. |
| 5,365,596 A | 11/1994 | Dante et al. |
| 5,420,409 A | 5/1995 | Longacre, Jr. et al. |
| 5,476,010 A | 12/1995 | Fleming et al. |
| 5,481,712 A | 1/1996 | Silver et al. |
| 5,581,625 A | 12/1996 | Connell et al. |
| 5,687,249 A | 11/1997 | Kato |
| 5,717,834 A | 2/1998 | Werblin et al. |
| 5,734,742 A | 3/1998 | Asaeda et al. |
| 5,742,037 A | 4/1998 | Scola et al. |
| 5,751,831 A | 5/1998 | Ono |
| 5,802,220 A | 9/1998 | Black et al. |
| 5,809,161 A | 9/1998 | Auty et al. |
| 5,825,483 A | 10/1998 | Michael et al. |
| 5,852,669 A | 12/1998 | Eleftheriadis et al. |
| 5,872,354 A | 2/1999 | Hanson |
| 5,917,602 A | 6/1999 | Bonewitz et al. |
| 5,932,862 A | 8/1999 | Hussey et al. |
| 5,937,096 A | 8/1999 | Kawai |
| 5,942,741 A | 8/1999 | Longacre et al. |
| 5,943,432 A | 8/1999 | Gilmore et al. |
| 5,960,097 A | 9/1999 | Pfeiffer et al. |
| 5,960,125 A | 9/1999 | Michael et al. |
| 6,046,764 A | 4/2000 | Kirby et al. |
| 6,049,619 A | 4/2000 | Anandan et al. |
| 6,061,471 A | 5/2000 | Coleman, Jr. |
| 6,072,494 A | 6/2000 | Nguyen |
| 6,072,882 A | 6/2000 | White et al. |
| 6,078,251 A | 6/2000 | Landt et al. |
| 6,088,467 A | 7/2000 | Sarpeshkar et al. |
| 6,115,480 A | 9/2000 | Washizawa |
| 6,158,661 A | 12/2000 | Chadima, Jr. et al. |
| 6,160,494 A | 12/2000 | Sodi et al. |
| 6,161,760 A | 12/2000 | Marrs et al. |
| 6,169,535 B1 | 1/2001 | Lee |
| 6,169,600 B1 | 1/2001 | Ludlow |
| 6,173,070 B1 | 1/2001 | Michael et al. |
| 6,175,644 B1 | 1/2001 | Scola et al. |
| 6,184,924 B1 | 2/2001 | Schneider et al. |
| 6,215,892 B1 | 4/2001 | Douglass et al. |
| 6,282,462 B1 | 8/2001 | Hopkins |
| 6,285,787 B1 | 9/2001 | Kawachi et al. |
| 6,298,176 B2 | 10/2001 | Longacre, Jr. et al. |
| 6,333,993 B1 | 12/2001 | Sakamoto |
| 6,346,966 B1 | 2/2002 | Toh |
| 6,347,762 B1 | 2/2002 | Sims et al. |
| 6,360,003 B1 | 3/2002 | Doi et al. |
| 6,396,517 B1 | 5/2002 | Beck et al. |
| 6,396,949 B1 | 5/2002 | Nichani |
| 6,408,429 B1 | 6/2002 | Marrion et al. |
| 6,446,868 B1 | 9/2002 | Robertson et al. |
| 6,483,935 B1 | 11/2002 | Rostami et al. |
| 6,487,304 B1 | 11/2002 | Szeliski |
| 6,525,810 B1 | 2/2003 | Kipman |
| 6,526,156 B1 | 2/2003 | Black et al. |
| 6,539,107 B1 | 3/2003 | Michael et al. |
| 6,545,705 B1 | 4/2003 | Sigel et al. |
| 6,549,647 B1 | 4/2003 | Skunes et al. |
| 6,573,929 B1 | 6/2003 | Glier et al. |
| 6,580,810 B1 | 6/2003 | Yang et al. |
| 6,587,122 B1 | 7/2003 | King |
| 6,597,381 B1 | 7/2003 | Eskridge et al. |
| 6,608,930 B1 | 8/2003 | Agnihotri et al. |
| 6,618,074 B1 | 9/2003 | Seeley et al. |
| 6,621,571 B1 | 9/2003 | Maeda et al. |
| 6,628,805 B1 | 9/2003 | Hansen et al. |
| 6,629,642 B1 | 10/2003 | Swartz et al. |
| 6,646,244 B2 | 11/2003 | Aas et al. |
| 6,668,075 B1 | 12/2003 | Nakamura |
| 6,677,852 B1 | 1/2004 | Landt |
| 6,681,151 B1 | 1/2004 | Weinzimmer et al. |
| 6,741,977 B1 | 5/2004 | Nagaya et al. |
| 6,753,876 B2 | 6/2004 | Brooksby et al. |
| 6,761,316 B2 | 7/2004 | Bridgelall et al. |
| 6,816,063 B2 | 11/2004 | Kubler et al. |
| 6,891,570 B2 | 5/2005 | Tantalo et al. |
| 6,919,793 B2 | 7/2005 | Heinrich et al. |
| 6,944,584 B1 | 9/2005 | Tenney et al. |
| 6,973,209 B2 | 12/2005 | Tanaka |
| 6,985,827 B2 | 1/2006 | Williams et al. |
| 6,987,528 B1 | 1/2006 | Nagahisa et al. |
| 6,997,556 B2 | 2/2006 | Pfleger |
| 6,999,625 B1 | 2/2006 | Nelson |
| 7,062,071 B2 | 6/2006 | Tsujino et al. |
| 7,066,388 B2 | 6/2006 | Perez |
| 7,070,099 B2 | 7/2006 | Patel |
| 7,085,401 B2 | 8/2006 | Averbuch et al. |
| 7,088,387 B1 | 8/2006 | Freeman et al. |
| 7,088,846 B2 | 8/2006 | Han et al. |
| 7,097,102 B2 | 8/2006 | Patel et al. |
| 7,175,090 B2 | 2/2007 | Nadabar |
| 7,181,066 B1 | 2/2007 | Wagman et al. |
| 7,227,978 B2 | 6/2007 | Komatsuzaki et al. |
| 7,266,768 B2 | 9/2007 | Ferlitsch et al. |
| 7,274,808 B2 | 9/2007 | Baharav et al. |
| 7,280,685 B2 | 10/2007 | Beardsley |
| 7,604,174 B2 | 10/2009 | Gerst et al. |
| 7,657,081 B2 | 2/2010 | Blais et al. |
| 7,751,625 B2 | 7/2010 | Ulrich et al. |
| 7,984,854 B2 | 7/2011 | Nadabar |
| 8,108,176 B2 | 1/2012 | Nadabar et al. |
| 2001/0042789 A1 | 11/2001 | Krichever et al. |
| 2002/0005895 A1 | 1/2002 | Freeman et al. |
| 2002/0099455 A1 | 7/2002 | Ward |
| 2002/0122582 A1 | 9/2002 | Masuda et al. |
| 2002/0177918 A1 | 11/2002 | Pierel et al. |
| 2002/0181405 A1 | 12/2002 | Ying |
| 2002/0196336 A1 | 12/2002 | Batson et al. |
| 2002/0196342 A1 | 12/2002 | Walker et al. |
| 2003/0062418 A1 | 4/2003 | Barber et al. |
| 2003/0095710 A1 | 5/2003 | Tessadro |
| 2003/0113018 A1 | 6/2003 | Nefian et al. |
| 2003/0137590 A1 | 7/2003 | Barnes et al. |
| 2003/0201328 A1 | 10/2003 | Jam et al. |
| 2003/0219146 A1 | 11/2003 | Jepson et al. |
| 2003/0227483 A1 | 12/2003 | Schultz et al. |
| 2004/0148057 A1 | 7/2004 | Breed et al. |
| 2004/0218806 A1 | 11/2004 | Phillips |
| 2005/0226490 A1 | 10/2005 | Phillips et al. |
| 2005/0257646 A1 | 11/2005 | Yeager |
| 2005/0275728 A1 | 12/2005 | Mirtich et al. |
| 2005/0275831 A1 | 12/2005 | Silver |
| 2005/0275833 A1 | 12/2005 | Silver |
| 2005/0275834 A1 | 12/2005 | Silver |
| 2005/0276445 A1 | 12/2005 | Silver et al. |
| 2005/0276459 A1 | 12/2005 | Eames et al. |
| 2005/0276460 A1 | 12/2005 | Silver, et al. |
| 2005/0276461 A1 | 12/2005 | Silver et al. |
| 2005/0276462 A1 | 12/2005 | Silver et al. |
| 2006/0022052 A1 | 2/2006 | Patel et al. |
| 2006/0107211 A1 | 5/2006 | Mirtich et al. |
| 2006/0107223 A1 | 5/2006 | Mirtich et al. |
| 2006/0131419 A1 | 6/2006 | Nunnink |
| 2006/0133757 A1 | 6/2006 | Nunnink |
| 2006/0146337 A1 | 7/2006 | Marshall et al. |
| 2006/0146377 A1* | 7/2006 | Marshall et al. .............. 358/486 |
| 2006/0223628 A1 | 10/2006 | Walker et al. |
| 2006/0249581 A1 | 11/2006 | Smith |
| 2006/0249587 A1 | 11/2006 | Choi et al. |
| 2006/0283952 A1 | 12/2006 | Wang |
| 2007/0146491 A1 | 6/2007 | Tremblay et al. |
| 2007/0181692 A1 | 8/2007 | Barkan et al. |
| 2008/0004822 A1 | 1/2008 | Nadabar et al. |
| 2008/0011855 A1 | 1/2008 | Nadabar |
| 2008/0036873 A1 | 2/2008 | Silver |
| 2008/0063245 A1 | 3/2008 | Benkley et al. |
| 2008/0166015 A1 | 7/2008 | Haering et al. |
| 2008/0205714 A1 | 8/2008 | Benkley |
| 2008/0219521 A1 | 9/2008 | Benkly |

| | | | |
|---|---|---|---|
| 2008/0226132 A1 | 9/2008 | Gardner et al. | |
| 2008/0309920 A1 | 12/2008 | Silver | |
| 2008/0310676 A1 | 12/2008 | Silver | |
| 2009/0121027 A1 | 5/2009 | Nadabar | |
| 2009/0154779 A1 | 6/2009 | Satyan et al. | |
| 2009/0257621 A1 | 10/2009 | Silver | |
| 2009/0273668 A1 | 11/2009 | Mirtich et al. | |
| 2010/0241901 A1 | 9/2010 | Mirtich et al | |
| 2010/0241911 A1 | 9/2010 | Shih et al. | |
| 2010/0318936 A1 | 12/2010 | Tremblay et al. | |

FOREIGN PATENT DOCUMENTS

| | | |
|---|---|---|
| DE | 10040563 | 2/2002 |
| EP | 0815688 | 1/1998 |
| EP | 0939382 | 9/1999 |
| EP | 0896290 | 10/2004 |
| EP | 1469420 | 10/2004 |
| EP | 1975849 | 10/2008 |
| GB | 2226130 | 6/1990 |
| GB | 2309078 | 7/1997 |
| JP | 09185710 | 7/1997 |
| JP | 9288060 | 11/1997 |
| JP | 11101689 | 4/1999 |
| JP | 200084495 | 3/2000 |
| JP | 2000-293694 | 10/2000 |
| JP | 2000298103 | 10/2000 |
| JP | 2000322450 | 11/2000 |
| JP | 2001-109884 | 4/2001 |
| JP | 2001-194323 | 7/2001 |
| JP | 2002148205 | 5/2002 |
| JP | 2002214153 | 7/2002 |
| JP | 2002318202 | 10/2002 |
| JP | 2003270166 | 9/2003 |
| JP | 2004145504 | 5/2004 |
| WO | WO 96/09597 | 3/1996 |
| WO | WO-200215120 | 2/2002 |
| WO | 02075637 | 9/2002 |
| WO | 03102859 | 12/2003 |
| WO | 2005050390 | 6/2005 |
| WO | WO-2005124317 | 6/2005 |
| WO | WO-2005124709 | 12/2005 |
| WO | WO-2005124719 | 12/2005 |
| WO | 2008118419 | 10/2008 |
| WO | 2008118425 | 10/2008 |

OTHER PUBLICATIONS

Di Mauro, E. C., et al., "Check—a generic and specific industrial inspection tool", *IEE Proc.-Vis. Image Signal Process.*, vol. 143, No. 4,(Aug. 27, 1996),pp. 241-249.
National Instruments, "IMAQVision Builder Tutorial", *IMAQ XP-002356530*, http://www.ni.com/pdf/manuals/322228c.pdf,(Dec. 2000).
"Cellular device processes at ultrafast speeds", *VisionSystems Design*, (Feb. 2003).
"ADSP-BF533 Blackfin Processor Hardware Reference", *Analog Devices Inc.—Media Platforms and Services Group*, Preliminary Revision—Part No. 82-002005-01,(Mar. 2003).
"Blackfin Processor Instruction Set Reference", *Analog Devices, Inc.*, Revision 2.0, Part No. 82-000410-14,(May 2003).
"LM9630 100×128, 580 fps UltraSensitive Monochrome CMOS Image Sensor", *National Semiconductor Corp.*, www.national.com Rev. 1.0,(Jan. 2004).
"CCD/CMOS Sensors Spot Niche Application", *PennWell Corporation*, Vision System Design—Imaging and Machine Vision Technology,(2004).
"iQ 180", *Adaptive Optics Associates 900 Coles Road Blackwood*, NJ 08012-4683, (Dec. 2003).
"Laser Scanning Product Guide", *Adaptive Optics Associates—Industrial Products and Systems 90 Coles Road Blackwood*, NJ 08012, Industrial Holographic and Conventional Laser 1D, Omnidirectional Bar Codes Scanners,(Mar. 2003).
"Matsushita Imagecheckers", *NaiS Machine Vision—Matsushita Machine Vision Systems*, (2003).
"Matsushita LightPix AE10", *NAiS Machine Vision—Matsushita Machine Vision Systems*, (2003).
"Simatic Machine Vision", *Simatic VS 100 Series Siemens AG*, www.siemens.com/machine-vision,(Apr. 1, 2003).
"SmartCapture Tool", *Feature Fact Sheet, Visionx Inc.*, www.visionxinc.com, (2003).
Asundi, A., et al., "High-Speed TDI Imaging for Peripheral Inspection", *Proc. SPIE* vol. 2423, Machine Vision Applications in Industrial Inspection III, Frederick Y. Wu; Stephen S. Wilson; Eds.,(Mar. 1995),189-194.
Baillard, C., et al., "Automatic Reconstruction of Piecewise Planar Models from Multiple Views", *CVPR*, vol. 2, No. 2,(1999),2559.
Baumberg, A. M., et al., "Learning Flexible Models from Image Sequences", *University of Leeds, School of Computer Studies, Research Report Series*, Report 93.36, (Oct. 1993),pp. 1-13.
Chang, Dingding, et al., "Feature Detection of Moving Images using a Hierarchical Relaxation Method", *IEICE Trans. Inf. & Syst.*, vol. E79-D, (Jul. 7, 1996).
Corke, Peter I., et al., "Real Time Industrial Machine Vision", *Electrical Engineering Congress Sydney, Australia*, CSIRO Divison of Manufacturing Technology,(1994).
Demotte, Donald, "Visual Line Tracking", *Application Overview & Issues Machine Vision for Robot Guidance Workshop*, (May 5, 2004).
Kim Zuwhan, et al., "Automatic Description of Complex Buildings with Multiple Images", *IEEE 0-7695-0813-8/00*, (2000),155-162.
Marsh, R, et al., "The application of knowledge based vision to closed-loop control of the injection molding process", *SPIE* vol. 3164, Faculty of Engineering University of the West of England United Kingdon,(1997),605-16.
Rohr, K., "Incremental Recognition of Pedestrians from Image Sequences", *CVPR93*, (1993).
West, Perry C., "High Speed, Real-Time Machine Vision", *Imagenation and Automated Vision Systems, Inc.*, (2001).
Wilson, Andrew, "CMOS/CCD sensors spot niche applications", *Vision Systems Design*, (Jun. 2003).
Zarandy, Akos, et al., "Ultra-High Frame Rate Focal Plane Image Sensor and Processor", *IEEE Sensors Journal*, vol. 2, No. 6,(2002).
Zarandy, A., et al., "Vision Systems Based on the 128X128 Focal Plane Cellular Visual Microprocessor Chips", *IEEE*, (Mar. 2003),III-518-III-521.
"Cognex VisionPro", *Getting Started—QuickStart Tutorial*, Cognex Corporation, 590-6560, Revision 3.5,(May 2004),69-94.
Haering, N., et al., "Visual Event Detection", *Kluwer Academic Publishers*, Chapter 2, Section 8,(2001).
Uno, T., et al.,"A Method of Real-Time Recognition of Moving Objects and its Application", *Pattern Recognition; Pergamon Press*, vol. 8, pp. 201-208, (1976),pp. 201-208.
Shane C. Hunt, Mastering Microsoft PhotoDraw 2000, SYBEX, Inc., May 21, 1999.
Integrated Design Tools, High-Speed CMOS Digital Camera, X-Stream Vision User's Manual, 2000.
IO Industries, High Speed Digital Video Recording Software 4.0,IO industries, Inc.—Ontario, CA, 2002.
Phillip Kahn, Building Blocks for Computer Vision Systems, IEEE Expert, vol. 8, No. 6, XP002480004, pp. 40-50, Dec. 6, 1993.
Matrox, Interactive Windows Imaging Software for Industrial and Scientific Applications, Inspector 4.0-Matrox Imaging, pp. 8, Apr. 15, 2002.
Whelan, P. et al., Machine Vision Algorithms in Java, Chapter 1—An Introduction to Machine Vision, Springer Verlag, XP002480005, 2001.
Photron, USA, Product information for FASTCAM-X 1280 PCI, Copyright 2004, www.photron.com.
Photron, USA, Product information for FASTCAM PCI, Copyright 2004, www.photron.com.
Photron, USA, Product information for ULTIMA 1024, Copyright 2004, www.photron.com.
Photron, USA, Product information for Ultima 512, Copyright 2004, www.photron.com.
Photron, USA, Product information for Ultima APX, Copyright 2004, www.photron.com.
KSV Instruments Ltd., HiSIS 2002—High Speed Imaging System, copyright 1996-1998, http://www.changkyung.co.kr/ksv/hisis/highsp.htm.

Cognex Corporation 3000/4000/5000 Image Processing, Revision 7.4 590-0135 Edge Detection Tool, 1996.
Cognex Corporation 4000/5000 SMD Placement Guidance Package, User's Manual, Release 3.8.00, Chapter 15, 1998.
Cognex Corporation, CVL Vision Tools Guide, Cognex MVS-8000 Series, Chapter 5, Symbol Tool, CVL 5.4, Dec. 1999.
Adaptive Optics Associates, Laser Scanning Product Guide, Industrial Products and Systems, Mar. 2003.
Wright, Anne, et al, Cognachrome Vision System User's Guide, Newton Research Labs, Manual Edition 2.0, Documents Software Version 26.0, Jun. 3, 1996.
Stemmer Imaging GmbH, Going Multimedia with Common Vision Blox, Product News, www.stemmer-imaging.de, http://www.imasys.fr/pages/news/item.php?view=319&item=313, Feb. 20, 2003.
Cordin Company, Electronic Imaging Systems, High Speed Imaging Solutions: 200-500 Series Cameras, www.cordin.com, 2004.
Bi-i, Bio-inspired Real-Time Very High Speed Image Processing Systems, AnaLogic Computers Ltd., http://www.analogic-computers.com/cgi-bin/phprint21.php, 2004.
Bi-i, AnaLogic Computers Ltd., 2003.
RVSI, Smart Camera Reader for Directly Marked Data Matrix Codes, HawkEye 1515 with GUI, 2004.
Olympus Industrial, High Speed, High Quality Imaging Systems, i-speed Product Brochure—Publisher Olympus Industrial, 2002.
Olympus Industrial, Design Philosophy, i-speed, 2002.
ICS 100, Intelligent Camera Sensor, SICK Product Information, SICK Industrial Sensors, 6900 West 110th St., Minneapolis, MN 55438, www.sickusa.com, Jan., 3, 2002.
Denis, Jolivet, LabView and IMAQ Vision Builder Provide Automated Visual Builder, LabVIEW, National Instruments, XP002356529, http://www.ni.com/pdf/csma/us/JNDESWG.pdf, 2001.
CV-2100 Series, Keyence America, http://www.keyence.com/products/vision/cv_2100_spec.html, High-Speed Digital Machine Vision System, Dec. 29, 2003.
Stauffer, Chris et al., Tracking-Based Automatic Object Recognition, Artificial Intelligence Laboratory, Massachusetts Institute of Technology, Cambridge, MA http://www.ai.mit.edu, pp. 133-134, 2001.
Singapore Patent Application No. 200608485-9, 1st Written Opinion, Australian Patent Office, dated Feb. 15, 2008.
European Patent Application No., 05 758 780.0, Communication pursuant to 94(3) EPC, dated Mar. 25, 2009.
Singapore Patent Application No. 200608485-9, 2nd Written Opinion, Australian Patent Office, dated Sep. 24, 2008.
The International Search Report and Written Opinion of the International Searching Authority, International Application No. PCT/US2005/019923 dated Jan. 9, 2006.
Non-Final Office Action, U.S. Appl. No. 10/865,155, Dec. 17, 2008.
Non-Final Office Action, U.S. Appl. No. 10/865,155, Jun. 10, 2009.
Final Office Action, U.S. Appl. No. 10/865,155, Jul. 23, 2009.
Amendment, U.S. Appl. No. 10/186,155, Jan. 15, 2010.
Interview Summary, U.S. Appl. No. 10/865,155, Jan. 21, 2010.
Non-Final Office Action, U.S. Appl. No. 10/865,155, dated Feb. 17, 2010.
Notice of Allowance, U.S. Appl. No. 11/138,025, Mar. 9, 2009.
Notice of Allowance, U.S. Patent Appl. No. 11/138,025, Nov. 17, 2009.
Amendment, U.S. Appl. No. 11/138,025, Apr. 8, 2009.
Non-Final Office Action, U.S. Appl. No. 11/138,025, Dec. 19, 2008.
Non Final Office Action, U.S. Appl. No. 11/138,033, Jun. 14, 2010.
Amendment, U.S. Appl. No. 11/138,033, Dec. 18, 2009.
Amendment, U.S. Appl. No. 11/136,103, Dec. 18, 2009.
Amendment, U.S. Appl. No. 11/136,103, Jun. 23, 2009.
Amendment, U.S. Appl. No. 11/136,103, Feb. 12, 2009.
Non-Final Office Action, U.S. Appl. No. 11/136,103, Nov. 13, 2008.
Amendment, U.S. Appl. No. 11/136,103, Mar. 10, 2008.
Non-Final Office Action, U.S. Appl. No. 11/136,103, Dec. 10, 2007.
Amendment, U.S. Appl. No. 11/136,103, Jun. 23, 2008.
Notice of Allowance, U.S. Appl. No. 11/136,103, May 1, 2008.
Response to OA in European Patent Application No. 05763341.4, Dec. 27, 2007.
European Office Action for Application 05758780.0, dated Mar. 25, 2009.
Response to OA in European Patent Application No. 05763341.4, Oct. 1, 2009.
International Preliminary Report on Patentability, European Patent Application No., 05763341.4, dated May 11, 2006.
Singapore Patent Application No. 2006 08485-9, Invitation to Respond to Written Opinion, Oct. 20, 2008.
Amendment, U.S. Appl. No. 11/138,023, May 26, 2009.
Non-Final Office Action, U.S. Appl. No. 11/138,023, Jan. 22, 2009.
Amendment, U.S. Appl. No. 11/138,023, Dec. 3, 2008.
Non-Final Office Action, U.S. Appl. No. 11/138,023, sep. 17, 2008.
Amendment, U.S. Appl. No. 11/138,023, Jun. 9, 2008.
Non-Final Office Action, U.S. Appl. No. 11/138,023, Jan. 9, 2008.
European Patent application No. 05758780.0, response to office action, Oct. 5, 2009.
U.S. Appl. No. 10/865,155, prosecution file history from Feb. 17, 2010 through Sep. 30, 2010, Non-Final OA dated Feb. 17, 2010, response to non-final dated Jul. 19, 2010, final rejection dated Jul. 30, 2010, final rejection response dated Sep. 30, 2010.
Communication from the Examining Division of the European Patent Office, European application No. 05763341.4, communication dated, Jul. 6, 2010 through Sep. 20, 2010.
PCT/US2008/083191, Search Report, Feb. 17, 2009.
Response to Written Opinion, Singapore patent No. 200608484-2, Dec. 11, 2009.
Prosecution file history for U.S. Appl. No. 10/865,155, Jun. 9, 2004 through Jan. 10, 2011.
Prosecution file history for U.S. Appl. No. 10/979,535, Nov. 2, 2004 through Jan. 29, 2009.
Prosecution file history for U.S. Appl. No. 10/979,572, Nov. 2, 2004 through Jan. 11, 2001.
Prosecution file history for U.S. Appl. No. 10/987,497, Oct. 2, 2008 through Mar. 30, 2009.
Prosecution file history for U.S. Appl. No. 10/988,120, Nov. 12, 2004 through Dec. 31, 2009.
Prosecution file history for U.S. Appl. No. 11/059,512, Feb. 16, 2005 through Dec. 18, 2008.
Non-Final Office Action for U.S. Appl. No. 11/094,650, dated Jan. 28, 2009.
Prosecution file history for U.S. Appl. No. 11/136,019, May 24, 2005 through Oct. 29, 2010.
Prosecution file history for U.S. Appl. No. 11/136,103, May 24, 2005 through Dec. 18, 2009.
Prosecution file history for U.S. Appl. No. 11/138,033, Jun. 27, 2007 through Oct. 25, 2007.
Prosecution file history for U.S. Appl. No. 11/138,025, May 26, 2005, through Jan. 17, 2009.
Prosecution file history for U.S. Appl. No. 11/616,726, Dec. 27, 2006 through Aug. 20, 2010.
Prosecution file history for U.S. Appl. No. 11/769,494, Jun. 27, 2007 through Oct. 25, 2007.
European Patent application No. 05758781, file history Feb. 18, 2006 through Mar. 25, 2009.
PCT/US2005/019923 International Preliminary Report on Patentability, May 12, 2006.
European Patent application No. 05763341, file history Jun. 13, 2007 through Sep. 20, 2010.
Japanese Patent application No. 2007-527,637, Office action English translation, dated May 25, 2010.
Japanese Patent Application 2007-527 637, Response to Office action dated, Sep. 1, 2010, English translation.
European Patent application No. 05756516, file history Feb. 23, 2006 through Feb. 10, 2009.
International Preliminary Report on Patentability, PCT/US2008/007280 Publication Date Dec. 17, 2009.
International Search Report, PCT/US2008/007302, Publication Date Nov. 5, 2009.
Written Opinion of the International Searching Authority PCT/US20081007302, Publication Date Nov. 5, 2009.
Written Opinion of the International Searching Authority, PCT/US2008/007280, Publication Date Dec. 15, 2009.

Apple Computer Inc., Studio Display User's Manual online, retrieved on Nov. 24, 2010, retrieved from the Internet http://manuals.info.apple.com/en/studioDisplay_15inLCDUserManual.pdf, 1998.
Search Report, PCT/US2008/083191, Publication Date Feb. 17, 2009.
Cognex Corporation, VisionPro Getting Started, Revision 3.2, 590-6508, copyright 2003.
National Instruments, IMAQVision Builder Tutorial, IMAQ XP-002356530, b, ttp://www.ni.com.'pdf,'manuals/322228c.pdf, Publication Date, Dec. 2000.
Japanese patent application No. 2007-527,613, 1st office action translation, dated Dec. 21, 2010.
Japanese patent application No. 2007-527,637, 1st office action translation, dated Jan. 26, 2011.
Allen-Bradley, Bulletin 2803 VIM Vision Input Module, Cat. No. 2803-VIM2, Printed USA, (1991) (submitted in 3 parts).
Allen-Bradley, User's Manual, Bulletin 2803 VIM Vision Input Module, Cat. No. 2803-VIM1, (1987) (submitted in 2 parts).
Allen-Bradley, Bulletin 5370 CVIM Configurable Vision Input Module, User Manual Cat. No. 5370-CVIM, (1995) (submitted in 3 parts).
European patent 05763341.4, response to examination report, Jul. 18, 2011.
Japanese patent No. 2007-527,620, office action translated, dated Jan. 18, 2011.
Cognex Corporation, 3000/4000/5000 Vision Tools, revision 7.6, 590-0136, Chapter 10, 1996.
Cognex Corporation, 3000/4000/5000 Vision Tools, revision 7.6, 590-0136, Chapter 13, 1996.
Japanese patent No. 2007-527,620, office action response machine translated, dated Dec. 2010.
Japanese patent No. 2007-527,637, office action response machine translated, dated Aug. 1, 2011.
Japanese patent No. 2007-527,620, office action response machine translated, dated Jul. 19, 2011.
Office Action, Japanese patent application No. 2007-527620, dated Mar. 28, 2012.
"Cognex VisionPro", Getting Started—QuickStart Tutorial, Cognex Corporation, 590-6560, Revision 3.5,(May 2004), 69-94.
IBM, "Software Controls for Automated Inspection Device Used to Check Interposer Buttons for Defects", IP.com Journal, IP.com Inc., West Henrietts, NY, US, (Mar. 27, 2003).
Lavision GmbH, "High Speed CCD/CMOS Camera Systems", Overview of state-of-the-art High Speed Digital Camera Systems—UltraSpeedStar, www.lavision.de,(Sep. 24, 2004).
KSV Instruments Ltd., "HiSIS 2002—High Speed Imaging System", www.ksvltd.fi,(Sep. 24, 2004).
Non-Final Office Action, U.S. Appl. No. 10/865,155, dated Jan. 10, 2011.
Response to Office Action, U.S. Appl. No. 10/865,155, dated Jan. 10, 2011, filed May 10, 2011.
Final Office Action, U.S. Appl. No. 10/865,155, dated Jun. 16, 2011.
Response to Final Office Action, U.S. Appl. No. 10/865,155, dated Jun. 16, 2011, filed Dec. 15, 2011.
Non-Final Office Action, U.S. Appl. No. 11/136,103, dated Dec. 10, 2007.
Response to Non-Final Office Action, U.S. Appl. No. 11/136,103, dated Dec. 10, 2007, filed Mar. 10, 2008.
Non-Final Office Action, U.S. Appl. No. 11/136,103, dated Nov. 13, 2008.
Response to Non-Final Office Action, U.S. Appl. No. 11/136,103, dated Nov. 13, 2008, filed Feb. 12, 2009.
Notice of Allowance, U.S. Appl. No. 11/136,103, dated May 1, 2008.
Amendment in Response to Notice of Allowance, U.S. Appl. No. 11/136,103, dated May 1, 2008, filed Jun. 23, 2008.
Notice of Allowance, U.S. Appl. No. 11/136,103, dated Mar. 23, 2009.
Amendment in Response to Notice of Allowance, U.S. Appl. No. 11/136,103, dated Mar. 23, 2009, filed Jun. 23, 2009.
Amendment, U.S. Appl. No. 11/136,103, filed Dec. 18, 2009.
Notice of Allowance, U.S. Appl. No. 11/136,103, dated Feb. 21, 2012.
Non-Final Office Action, U.S. Appl. No. 11/769,494, dated Jun. 29, 2011.
Response to Non-Final Office Action, U.S. Appl. No. 11/769,494, dated Jun. 29, 2011, dated Dec. 28, 2011.
Notice of Allowance, U.S. Appl. No. 11/769,494, dated Jan. 11, 2012.
Non-Final Office Action, U.S. Appl. No. 11/059,512, dated Jul. 6, 2007.
Response to Non-Final Office Action, U.S. Appl. No. 11/059,512, dated Jul. 6, 2007, filed Dec. 4, 2007.
Final Office Action, U.S. Appl. No. 11/059,512, dated Apr. 25, 2008.
Response to Final Office Action, U.S. Appl. No. 11/059,512, dated Apr. 25, 2008, filed Sep. 23, 2008.
Non-Final Office Action, U.S. Appl. No. 11/059,512, dated Dec. 18, 2008.
Amendment, U.S. Appl. No. 11/138,033, dated Dec. 18, 2009.
Non-Final Office Action, U.S. Appl. No. 11/138,033, dated Jun. 14, 2010.
Response to Non-Final Office Action, U.S. Appl. No. 11/138,033, dated Jun. 14, 2010, filed Nov. 15, 2010.
Final Office Action, U.S. Appl. No. 11/138,033, dated Jan. 10, 2011.
Response to Final Office Action, U.S. Appl. No. 11/138,033, dated Jan. 10, 2011, filed Jun. 10, 2011.
Notice of Allowablility, U.S. Appl. No. 11/138,033, dated Jan. 11, 2010.
Notice of Allowance, U.S. Appl. No. 11/138,033, dated Oct. 28, 2011.
Non-Final Office Action, U.S. Appl. No. 11/138,023, dated Jan. 9, 2008.
Response to Non-Final Office Action, U.S. Appl. No. 11/138,023, dated Jan. 9, 2008, filed Jun. 9, 2008.
Non-Final Office Action, U.S. Appl. No. 11/138,023, dated Jan. 22, 2009.
Response to Non-Final Office Action, U.S. Appl. No. 11/138,023, dated Jan. 22, 2009, filed May 26, 2009.
Amendment filed with Request for Continued Examination, U.S. Appl. No. 11/138,023, dated Aug. 25, 2011.
Notice of Allowance, U.S. Appl. No. 11/138,023, dated Sep. 6, 2011.
Non-Final Office Action, U.S. Appl. No. 11/138,025, dated Dec. 19, 2008.
Response to Non-Final Office Action, U.S. Appl. No. 11/138,025, dated Dec. 19, 2008, filed Apr. 8, 2009.
Restriction Requirement, U.S. Appl. No. 11/138,025, dated Jul. 21, 2009.
Response to Restriction Requirement, U.S. Appl. No. 11/138,025, dated Jul. 21, 2009, filed Sep. 21, 2009.
Notice of Allowance, U.S. Appl. No. 11/138,025, dated Dec. 28, 2011.
Office Action, Japan Application No. 2007527620, dated Jan. 18, 2011.
Response to Office Action, Japan Application No. 2007-527,620, dated Jan. 18, 2011, filed Jul. 19, 2011.
Office Action, Japan Application No. 2007-527,637, dated Jun. 1, 2010.
Response to Office Action, Japan Application No. 2007-527,637, Jun. 1, 2010, filed Dec. 1, 2010.
Office Action, Japan Application No. 2007-527,637, dated Feb. 1, 2011.
Response to Office Action, Japan Application No. 2007-527,637, dated Feb. 1, 2011, filed Aug. 1, 2011.
Office Action, Europen Patent Application No. 05763341.4, dated Jun. 13, 2007.
Response to Office Action, Europen Patent Application No. 05763341.4, dated Jun. 13, 2007, filed Dec. 24, 2007.
Office Action, Europen Patent Application No. 05763341.4, dated Mar. 25, 2009.
Office Action, Europen Patent Application No. 05763341.4, dated Sep. 20, 2010.
Response to Office Action, Europen Patent Application No. 05763341.4, dated Sep. 20, 2010, filed Jul. 18, 2011.
"International Preliminary Report on Patentability", International Searching Authority, Application No. PCT/US2005/019923, dated May 12, 2006.

* cited by examiner

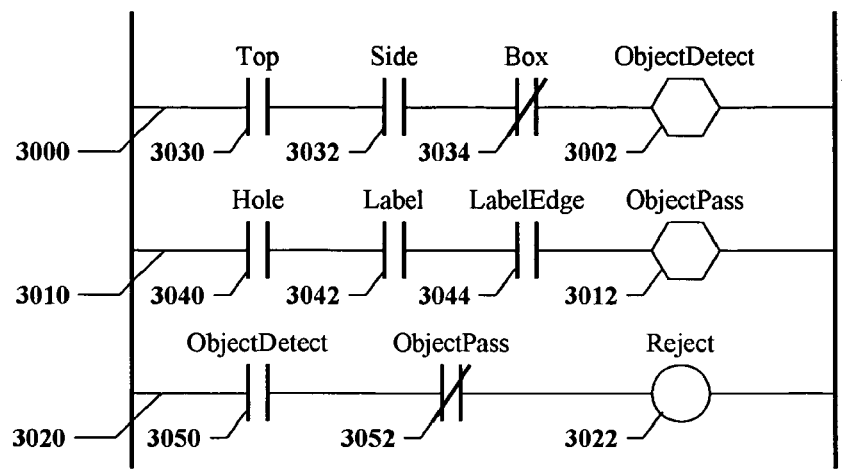
Fig 30
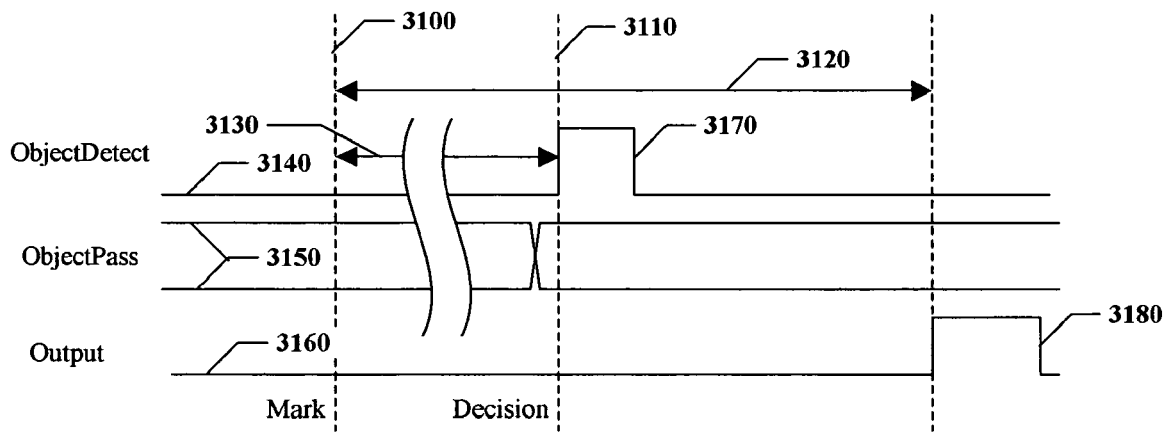
Fig 31
| | Frame | 57 | 58 | 59 | 60 | 61 | 62 | 63 | 64 | 65 | 66 | 67 | 68 |
|---|---|---|---|---|---|---|---|---|---|---|---|---|---|
| 3210 | Frame | 57 | 58 | 59 | 60 | 61 | 62 | 63 | 64 | 65 | 66 | 67 | 68 |
| 3220 | Time (ms) | 36.1 | 38.1 | 40.1 | 42.2 | 44.2 | 46.2 | 48.3 | 50.3 | 52.4 | 54.4 | 56.4 | 58.5 |
| 3225 | Encoder | 381 | 429 | 475 | 521 | 569 | 617 | 663 | 709 | 756 | 804 | 852 | 898 |
| 3230 | ObjectDetect | 0.00 | 0.17 | 0.89 | 1.00 | 1.00 | 0.96 | 1.00 | 0.73 | 0.06 | 0.00 | 0.00 | 0.00 |
| 3240 | Location (pixels) | | | -3.5 | -2.1 | -0.6 | 0.9 | 2.3 | 3.9 | | | | |
| 3250 | Mark location | | | | | | | | | | 45.0 | | |
| 3260 | Mark first | | | 40.1 | | | | | | | | | |
Fig 32

METHOD AND APPARATUS FOR DETECTING AND CHARACTERIZING AN OBJECT

CROSS REFERENCE TO RELATED APPLICATIONS

This application is a continuation of U.S. patent application Ser. No. 10/865,155, filed Jun. 9, 2004.

BACKGROUND OF THE INVENTION

1. Field of the Invention

The invention relates to automated detection and inspection of objects being manufactured on a production line, and more particularly to the related fields of industrial machine vision and automated image analysis.

2. Description of the Related Art

Industrial manufacturing relies on automatic inspection of objects being manufactured. One form of automatic inspection that has been in common use for decades is based on optoelectronic technologies that use electromagnetic energy, usually infrared or visible light, photoelectric sensors, and some form of electronic decision making.

One well-known form of optoelectronic automatic inspection uses an arrangement of photodetectors. A typical photodetector has a light source and a single photoelectric sensor that responds to the intensity of light that is reflected by a point on the surface of an object, or transmitted along a path that an object may cross. A user-adjustable sensitivity threshold establishes a light intensity above which (or below which) an output signal of the photodetector will be energized.

One photodetector, often called a gate, is used to detect the presence of an object to be inspected. Other photodetectors are arranged relative to the gate to sense the light reflected by appropriate points on the object. By suitable adjustment of the sensitivity thresholds, these other photodetectors can detect whether certain features of the object, such as a label or hole, are present or absent. A decision as to the status of the object (for example, pass or fail) is made using the output signals of these other photodetectors at the time when an object is detected by the gate. This decision is typically made by a programmable logic controller (PLC), or other suitable electronic equipment.

Automatic inspection using photodetectors has various advantages. Photodetectors are inexpensive, simple to set up, and operate at very high speed (outputs respond within a few hundred microseconds of the object being detected, although a PLC will take longer to make a decision).

Automatic inspection using photodetectors has various disadvantages, however, including:

Simple sensing of light intensity reflected from a point on the object is often insufficient for inspection. Instead it may be necessary to analyze a pattern of brightness reflected from an extended area. For example, to detect an edge it may be necessary to analyze a pattern of brightness to see if it corresponds to a transition from a lighter to a darker region;

It may be hard to arrange the photodetectors when many points on an object need to be inspected. Each such inspection point requires the use of a separate photodetector that needs to be physically mounted in such a way as to not interfere with the placement of the other photodetectors. Interference may be due to space limitations, crosstalk from the light sources, or other factors;

Manufacturing lines are usually capable of producing a mix of products, each with unique inspection requirements. An arrangement of photodetectors is very inflexible, so that a line changeover from one product to another would require the photodetectors to be physically moved and readjusted. The cost of performing a line changeover, and the risk of human error involved, often offset the low cost and simplicity of the photodetectors; and Using an arrangement of photodetectors requires that objects be presented at known, predetermined locations so that the appropriate points on the object are sensed. This requirement may add additional cost and complexity that can offset the low cost and simplicity of the photodetectors.

Another well-known form of optoelectronic automatic inspection uses a device that can capture a digital image of a two-dimensional field of view in which an object to be inspected is located, and then analyze the image and make decisions. Such a device is usually called a machine vision system, or simply a vision system. The image is captured by exposing a two-dimensional array of photosensitive elements for a brief period, called the integration or shutter time, to light that has been focused on the array by a lens. The array is called an imager and the individual elements are called pixels. Each pixel measures the intensity of light falling on it during the shutter time. The measured intensity values are then converted to digital numbers and stored in the memory of the vision system to form the image, which is analyzed by a digital processing element such as a computer, using methods well-known in the art to determine the status of the object being inspected.

In some cases the objects are brought to rest in the field of view, and in other cases the objects are in continuous motion through the field of view. An event external to the vision system, such as a signal from a photodetector, or a message from a PLC, computer, or other piece of automation equipment, is used to inform the vision system that an object is located in the field of view, and therefore an image should be captured and analyzed. Such an event is called a trigger.

Machine vision systems avoid the disadvantages associated with using an arrangement of photodetectors. They can analyze patterns of brightness reflected from extended areas, easily handle many distinct features on the object, accommodate line changeovers through software systems and/or processes, and handle uncertain and variable object locations.

Machine vision systems have disadvantages compared to an arrangement of photodetectors, including:

They are relatively expensive, often costing ten times more than an arrangement of photodetectors;

They can be difficult to set up, often requiring people with specialized engineering training; and They operate much more slowly than an arrangement of photodetectors, typically requiring tens or hundreds of milliseconds to make a decision. Furthermore, the decision time tends to vary significantly and unpredictably from object to object.

Machine vision systems have limitations that arise because they make decisions based on a single image of each object, located in a single position in the field of view (each object may be located in a different and unpredictable position, but for each object there is only one such position on which a decision is based). This single position provides information from a single viewing perspective, and a single orientation relative to the illumination. The use of only a single perspective often leads to incorrect decisions. It has long been observed, for example, that a change in perspective of as little as a single pixel can in some cases change an incorrect decision to a correct one. By contrast, a human inspecting an object usually moves it around relative to his eyes and the lights to make a more reliable decision.

Some prior art vision systems capture multiple images of an object at rest in the field of view, and then average those images to produce a single image for analysis. The averaging reduces measurement noise and thereby improves the decision making, but there is still only one perspective and illumination orientation, considerable additional time is needed, and the object must be brought to rest.

Some prior art vision systems that are designed to read alphanumeric codes, bar codes, or 2D matrix codes will capture multiple images and vary the illumination direction until either a correct read is obtained, or all variations have been tried. This method works because such codes contain sufficient redundant information that the vision system can be sure when a read is correct, and because the object can be held stationary in the field of view for enough time to try all of the variations. The method is generally not suitable for object inspection, and is not suitable when objects are in continuous motion. Furthermore, the method still provides only one viewing perspective, and the decision is based on only a single image, because information from the images that did not result in a correct read is discarded.

Some prior art vision systems are used to guide robots in pick-and-place applications where objects are in continuous motion through the field of view. Some such systems are designed so that the objects move at a speed in which the vision system has the opportunity to see each object at least twice. The objective of this design, however, is not to obtain the benefit of multiple perspectives, but rather to insure that objects are not missed entirely if conditions arise that temporarily slow down the vision system, such as a higher than average number of objects in the field of view. These systems do not make use of the additional information potentially provided by the multiple perspectives.

Machine vision systems have additional limitations arising from their use of a trigger signal. The need for a trigger signal makes the setup more complex—a photodetector must be mounted and adjusted, or software must be written for a PLC or computer to provide an appropriate message. When a photodetector is used, which is almost always the case when the objects are in continuous motion, a production line changeover may require it to be physically moved, which can offset some of the advantages of a vision system. Furthermore, photodetectors can only respond to a change in light intensity reflected from an object or transmitted along a path. In some cases, such a condition may not be sufficient to reliably detect when an object has entered the field of view.

Some prior art vision systems that are designed to read alphanumeric codes, bar codes, or two dimensional (2D) matrix codes can operate without a trigger by continuously capturing images and attempting to read a code. For the same reasons described above, such methods are generally not suitable for object inspection, and are not suitable when objects are in continuous motion.

Some prior art vision systems used with objects in continuous motion can operate without a trigger using a method often called self-triggering. These systems typically operate by monitoring one or more portions of captured images for a change in brightness or color that indicates the presence of an object. Self-triggering is rarely used in practice due to several limitations:

The vision systems respond too slowly for self-triggering to work at common production speeds;
The methods provided to detect when an object is present are not sufficient in many cases; and
The vision systems do not provide useful output signals that are synchronized to a specific, repeatable position of the object along the production line, signals that are typically provided by the photodetector that acts as a trigger and needed by a PLC or handling mechanism to take action based on the vision system's decision.

Many of the limitations of machine vision systems arise in part because they operate too slowly to capture and analyze multiple perspectives of objects in motion, and too slowly to react to events happening in the field of view. Since most vision systems can capture a new image simultaneously with analysis of the current image, the maximum rate at which a vision system can operate is determined by the larger of the capture time and the analysis time. Overall, one of the most significant factors in determining this rate is the number of pixels comprising the imager.

The time needed to capture an image is determined primarily by the number of pixels in the imager, for two basic reasons. First, the shutter time is determined by the amount of light available and the sensitivity of each pixel. Since having more pixels generally means making them smaller and therefore less sensitive, it is generally the case that increasing the number of pixels increases the shutter time. Second, the conversion and storage time is proportional to the number of pixels. Thus the more pixels one has, the longer the capture time.

For at least the last 25 years, prior art vision systems generally have used about 300,000 pixels; more recently some systems have become available that use over 1,000,000, and over the years a small number of systems have used as few as 75,000. Just as with digital cameras, the recent trend is to more pixels for improved image resolution. Over the same period of time, during which computer speeds have improved a million-fold and imagers have changed from vacuum tubes to solid state, machine vision image capture times generally have improved from about $\frac{1}{30}$ second to about $\frac{1}{60}$ second, only a factor of two. Faster computers have allowed more sophisticated analysis, but the maximum rate at which a vision system can operate has hardly changed.

Recently, CMOS imagers have appeared that allow one to capture a small portion of the photosensitive elements, reducing the conversion and storage time. Theoretically such imagers can support very short capture times, but in practice, since the light sensitivity of the pixels is no better than when the full array is used, it is difficult and/or expensive to achieve the very short shutter times that would be needed to make such imagers useful at high speed.

Due in part to the image capture time bottleneck, image analysis methods suited to operating rates significantly higher than 60 images per second have not been developed. Similarly, use of multiple perspectives, operation without triggers, production of appropriately synchronized output signals, and a variety of other useful functions have not been adequately considered in the prior art.

Recently, experimental devices called focal plane array processors have been developed in research laboratories. These devices integrate analog signal processing elements and photosensitive elements on one substrate, and can operate at rates in excess of 10,000 images per second. The analog signal processing elements are severely limited in capability compared to digital image analysis, however, and it is not yet clear whether such devices can be applied to automated industrial inspection.

Considering the disadvantages of an arrangement of photodetectors, and the disadvantages and limitations of current machine vision systems, there is a compelling need for systems and methods that make use of two-dimensional imagers and digital image analysis for improved detection and inspection of objects in industrial manufacturing.

SUMMARY OF THE INVENTION

The present invention provides systems and methods for automatic optoelectronic detection and inspection of objects, based on capturing digital images of a two-dimensional field of view in which an object to be detected or inspected may be located, and then analyzing the images and making decisions. These systems and methods analyze patterns of brightness reflected from extended areas, handle many distinct features on the object, accommodate line changeovers through software means, and handle uncertain and variable object locations. They are less expensive and easier to set up than prior art machine vision systems, and operate at much higher speeds. These systems and methods furthermore make use of multiple perspectives of moving objects, operate without triggers, provide appropriately synchronized output signals, and provide other significant and useful capabilities will become apparent to those skilled in the art.

While the present invention is directed primarily at applications where the objects are in continuous motion, and provides specific and significant advantages in those cases, it may also be used advantageously over prior art systems in applications where objects are brought to rest.

One aspect of the invention is an apparatus, called a vision detector, that can capture and analyze a sequence of images at higher speeds than prior art vision systems. An image in such a sequence that is captured and analyzed is called a frame. The rate at which frames are captured and analyzed, called the frame rate, is sufficiently high that a moving object is seen in multiple consecutive frames as it passes through the field of view (FOV). Since the objects moves somewhat between successive frames, it is located in multiple positions in the FOV, and therefore it is seen from multiple viewing perspectives and positions relative to the illumination.

Another aspect of the invention is a method, called dynamic image analysis, for inspecting objects by capturing and analyzing multiple frames for which the object is located in the field of view, and basing a result on a combination of evidence obtained from each of those frames. The method provides significant advantages over prior art machine vision systems that make decisions based on a single frame.

Yet another aspect of the invention is a method, called visual event detection, for detecting events that may occur in the field of view. An event can be an object passing through the field of view, and by using visual event detection the object can be detected without the need for a trigger signal.

Additional aspects of the invention will become apparent by a study of the figures and detailed descriptions given herein.

One advantage of the methods and apparatus of the present invention for moving objects is that by considering the evidence obtained from multiple viewing perspectives and positions relative to the illumination, a vision detector is able to make a more reliable decision than a prior art vision system, just as a human inspecting an object may move it around relative to his eyes and the lights to make a more reliable decision.

Another advantage is that objects can be detected reliably without a trigger signal, such as a photodetector. This reduces cost and simplifies installation, and allows a production line to be switched to a different product by making a software change in the vision detector without having to manually reposition a photodetector.

Another advantage is that a vision detector can track the position of an object as it moves through the field of view, and determine its speed and the time at which it crosses some fixed reference point. Output signals can then be synchronized to this fixed reference point, and other useful information about the object can be obtained as taught herein.

In order to obtain images from multiple perspectives, it is desirable that an object to be detected or inspected moves no more than a small fraction of the field of view between successive frames, often no more than a few pixels. As taught herein, it is generally desirable that the object motion be no more than about one-quarter of the FOV per frame, and in typical embodiments no more than 5% or less of the FOV. It is desirable that this be achieved not by slowing down a manufacturing process but by providing a sufficiently high frame rate. In an example system the frame rate is at least 200 frames/second, and in another example the frame rate is at least 40 times the average rate at which objects are presented to the vision detector.

An exemplary system is taught that can capture and analyze up to 500 frames/second. This system makes use of an ultra-sensitive imager that has far fewer pixels than prior art vision systems. The high sensitivity allows very short shutter times using very inexpensive LED illumination, which in combination with the relatively small number of pixels allows very short image capture times. The imager is interfaced to a digital signal processor (DSP) that can receive and store pixel data simultaneously with analysis operations. Using methods taught herein and implemented by means of suitable software for the DSP, the time to analyze each frame generally can be kept to within the time needed to capture the next frame. The capture and analysis methods and apparatus combine to provide the desired high frame rate. By carefully matching the capabilities of the imager, DSP, and illumination with the objectives of the invention, the exemplary system can be significantly less expensive than prior art machine vision systems.

The method of visual event detection involves capturing a sequence of frames and analyzing each frame to determine evidence that an event is occurring or has occurred. When visual event detection used to detect objects without the need for a trigger signal, the analysis would determine evidence that an object is located in the field of view.

In an exemplary method the evidence is in the form of a value, called an object detection weight, that indicates a level of confidence that an object is located in the field of view. The value may be a simple yes/no choice that indicates high or low confidence, a number that indicates a range of levels of confidence, or any item of information that conveys evidence. One example of such a number is a so-called fuzzy logic value, further described herein. Note that no machine can make a perfect decision from an image, and so will instead make judgments based on imperfect evidence.

When performing object detection, a test is made for each frame to decide whether the evidence is sufficient that an object is located in the field of view. If a simple yes/no value is used, the evidence may be considered sufficient if the value is "yes". If a number is used, sufficiency may be determined by comparing the number to a threshold. Frames where the evidence is sufficient are called active frames. Note that what constitutes sufficient evidence is ultimately defined by a human user who configures the vision detector based on an understanding of the specific application at hand. The vision detector automatically applies that definition in making its decisions.

When performing object detection, each object passing through the field of view will produce multiple active frames due to the high frame rate of the vision detector. These frames may not be strictly consecutive, however, because as the object passes through the field of view there may be some viewing perspectives, or other conditions, for which the evidence that the object is located in the field of view is not sufficient. Therefore it is desirable that detection of an object begins when a active frame is found, but does not end until a number of consecutive inactive frames are found. This number can be chosen as appropriate by a user.

Once a set of active frames has been found that may correspond to an object passing through the field of view, it is desirable to perform a further analysis to determine whether an object has indeed been detected. This further analysis may consider some statistics of the active frames, including the number of active frames, the sum of the object detection weights, the average object detection weight, and the like.

The above examples of visual event detection are intended to be illustrative and not comprehensive. Clearly there are many ways to accomplish the objectives of visual event detection within the spirit of the invention that will occur to one of ordinary skill.

The method of dynamic image analysis involves capturing and analyzing multiple frames to inspect an object, where "inspect" means to determine some information about the status of the object. In one example of this method, the status of an object includes whether or not the object satisfies inspection criteria chosen as appropriate by a user.

In some aspects of the invention dynamic image analysis is combined with visual event detection, so that the active frames chosen by the visual event detection method are the ones used by the dynamic image analysis method to inspect the object. In other aspects of the invention, the frames to be used by dynamic image analysis can be captured in response to a trigger signal.

Each such frame is analyzed to determine evidence that the object satisfies the inspection criteria. In one exemplary method, the evidence is in the form of a value, called an object pass score, that indicates a level of confidence that the object satisfies the inspection criteria. As with object detection weights, the value may be a simple yes/no choice that indicates high or low confidence, a number, such as a fuzzy logic value, that indicates a range of levels of confidence, or any item of information that conveys evidence.

The status of the object may be determined from statistics of the object pass scores, such as an average or percentile of the object pass scores. The status may also be determined by weighted statistics, such as a weighted average or weighted percentile, using the object detection weights. Weighted statistics effectively weight evidence more heavily from frames wherein the confidence is higher that the object is actually located in the field of view for that frame.

Evidence for object detection and inspection is obtained by examining a frame for information about one or more visible features of the object. A visible feature is a portion of the object wherein the amount, pattern, or other characteristic of emitted light conveys information about the presence, identity, or status of the object. Light can be emitted by any process or combination of processes, including but not limited to reflection, transmission, or refraction of a source external or internal to the object, or directly from a source internal to the object.

One aspect of the invention is a method for obtaining evidence, including object detection weights and object pass scores, by image analysis operations on one or more regions of interest in each frame for which the evidence is needed. In example of this method, the image analysis operation computes a measurement based on the pixel values in the region of interest, where the measurement is responsive to some appropriate characteristic of a visible feature of the object. The measurement is converted to a logic value by a threshold operation, and the logic values obtained from the regions of interest are combined to produce the evidence for the frame. The logic values can be binary or fuzzy logic values, with the thresholds and logical combination being binary or fuzzy as appropriate.

For visual event detection, evidence that an object is located in the field of view is effectively defined by the regions of interest, measurements, thresholds, logical combinations, and other parameters further described herein, which are collectively called the configuration of the vision detector and are chosen by a user as appropriate for a given application of the invention. Similarly, the configuration of the vision detector defines what constitutes sufficient evidence.

For dynamic image analysis, evidence that an object satisfies the inspection criteria is also effectively defined by the configuration of the vision detector.

One aspect of the invention includes determining a result comprising information about detection or inspection of an object. The result may be reported to automation equipment for various purposes, including equipment, such as a reject mechanism, that may take some action based on the report. In one example the result is an output pulse that is produced whenever an object is detected. In another example, the result is an output pulse that is produced only for objects that satisfy the inspection criteria. In yet another example, useful for controlling a reject actuator, the result is an output pulse that is produced only for objects that do not satisfy the inspection criteria.

Another aspect of the invention is a method for producing output signals that are synchronized to a time, shaft encoder count, or other event marker that indicates when an object has crossed a fixed reference point on a production line. A synchronized signal provides information about the location of the object in the manufacturing process, which can be used to advantage by automation equipment, such as a downstream reject actuator.

BRIEF DESCRIPTION OF THE DRAWINGS

The invention will be more fully understood from the following detailed description, in conjunction with the accompanying figures, wherein:

FIG. 30 shows an alternative representation for a portion of the configuration of a vision detector, based on a ladder diagram, a widely used industrial programming language;

FIG. 31 shows a timing diagram that will be used to explain how vision detector output signals are synchronized;

FIG. 32 shows an example of measuring the time at which an object crosses a fixed reference point, and also measuring object speed, pixel size calibration, and object distance and attitude in space;

DETAILED DESCRIPTION OF THE INVENTION

Discussion of Prior Art

Figure 1:
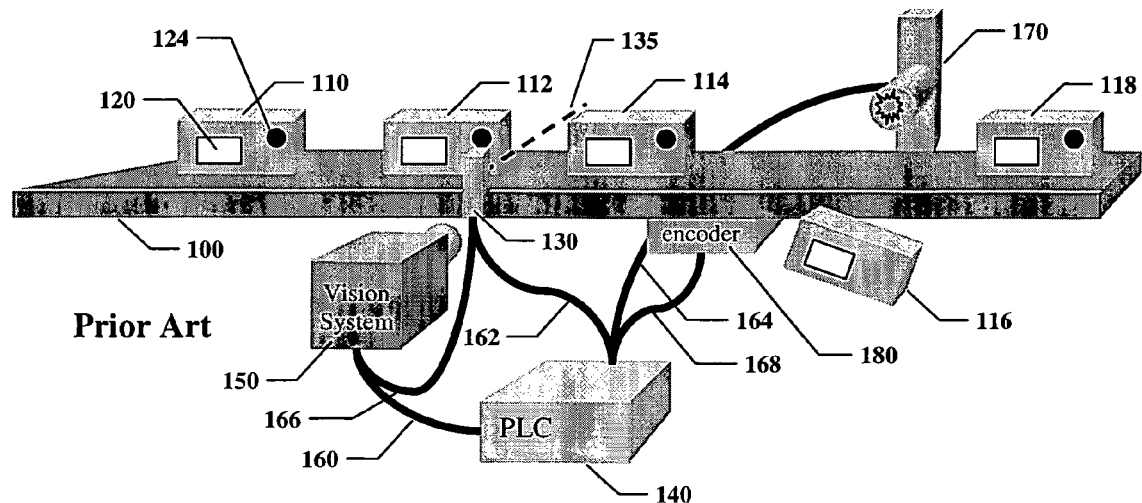
FIG. 1 shows a prior art machine vision system used to inspect objects on a production line.

FIG. 1 shows a prior art machine vision system used to inspect objects on a production line. Objects 110, 112, 114, 116, and 118 move left to right on a conveyer 100. Each object is expected to contain certain features, for example a label 120 and a hole 124. Objects incorrectly manufactured may be missing one or more features, or may have unintended features; for example, object 116 is missing the hole. On many production lines motion of the conveyer is tracked by a shaft encoder 180, which sends a signal 168 to a programmable logic controller (PLC) 140.

The objects move past a photodetector 130, which emits a beam of light 135 for detecting the presence of an object. Trigger signals 162 and 166 are sent from the photodetector to the PLC 140, and a machine vision system 150. On the leading edge of the trigger signal 166 the vision system 150 captures an image of the object, inspects the image to determine if the expected features are present, and reports the inspection results to the PLC via signal 160.

On the leading edge of the trigger signal 162 the PLC records the time and/or encoder count. At some later time the PLC receives the results of the inspection from the vision system, and may do various things with those results as appropriate. For example the PLC may control a reject actuator 170 via signal 164 to remove a defective object 116 from the conveyer. Since the reject actuator is generally downstream from the inspection point defined by the photodetector beam 135, the PLC must delay the signal 164 to the reject actuator until the defective part is in position in front of the reject actuator. Since the time it takes the vision system to complete the inspection is usually somewhat variable, this delay must be relative to the trigger signal 162, i.e. relative to the time and/or count recorded by the PLC. A time delay is appropriate when the conveyer is moving at constant speed; in other cases, an encoder is preferred.

FIG. 1 does not show illumination, which would be provided as appropriate according to various methods well-known in the art.

In the example of FIG. 1, the objects are in continuous motion. There are also many applications for which the production equipment brings objects to rest in front of the vision system.

Figure 2:
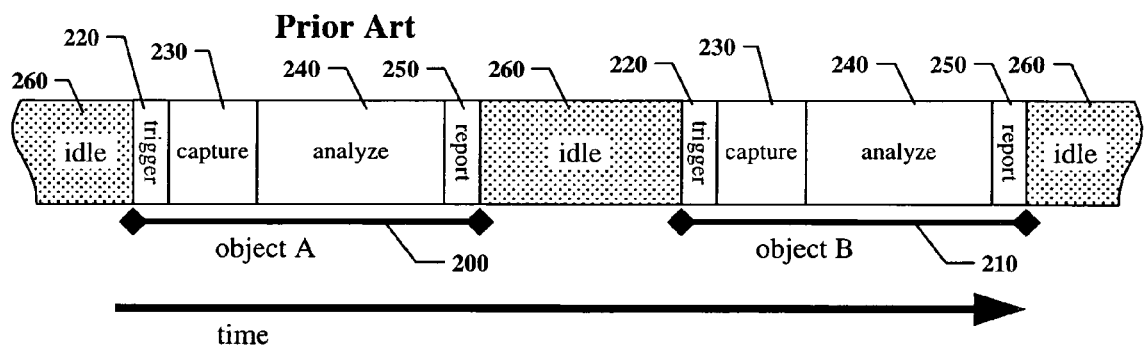
FIG. 2 shows a timeline that illustrates a typical operating cycle of a prior art machine vision system.

FIG. 2 shows a timeline that illustrates a typical operating cycle of a prior art machine vision system. Shown are the operating steps for two exemplary objects 200 and 210. The operating cycle contains four steps: trigger 220, image capture 230, analyze 240, and report 250. During the time between cycles 260, the vision system is idle. The timeline is not drawn to scale, and the amount of time taken by the indicated steps will vary significantly among applications.

The trigger 220 is some event external to the vision system, such as a signal from a photodetector 130, or a message from a PLC, computer, or other piece of automation equipment.

The image capture step 230 starts by exposing a two-dimensional array of photosensitive elements, called pixels, for a brief period, called the integration or shutter time, to an image that has been focused on the array by a lens. Each pixel measures the intensity of light falling on it during the shutter time. The measured intensity values are then converted to digital numbers and stored in the memory of the vision system.

During the analyze step 240 the vision system operates on the stored pixel values using methods well-known in the art to determine the status of the object being inspected. During the report step 250, the vision system communicates information about the status of the object to appropriate automation equipment, such as a PLC.

Figure 3:
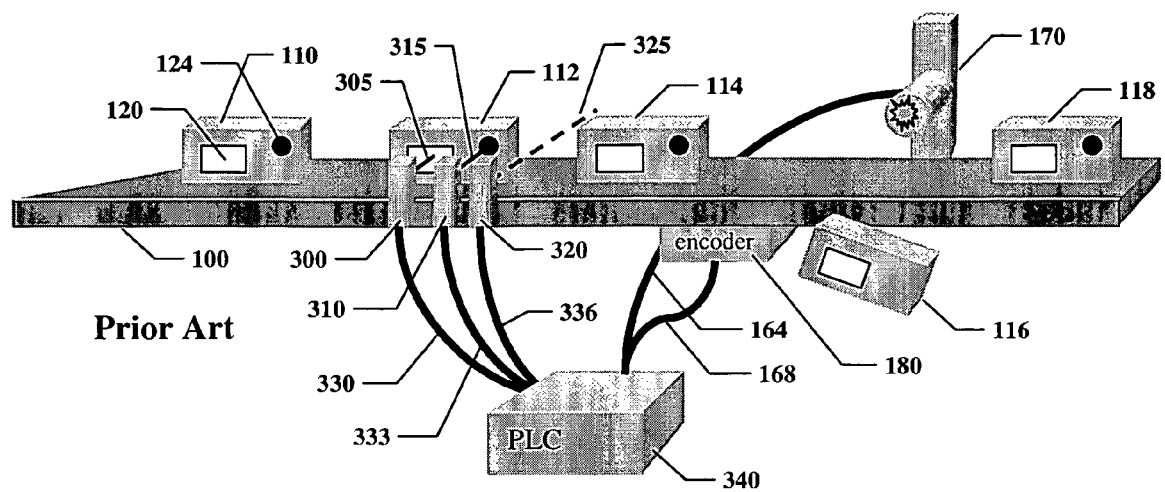
FIG. 3 shows prior art inspection of objects on a production line using photodetectors.

FIG. 3 shows prior art inspection of objects on a production line using photodetectors. Conveyer 100, objects 110, 112, 114, 116, 118, label 120, hole 124, encoder 180, reject actuator 170, and signals 164 and 168 are as described for FIG. 1. A first photodetector 320 with beam 325 is used to detect the presence of an object. A second photodetector 300 with beam 305 is positioned relative to the first photodetector 320 so as to be able to detect the presence of label 120. A third photodetector 310 with beam 315 is positioned relative to the first photodetector 320 so as to be able to detect the presence of hole 124.

A PLC 340 samples signals 330 and 333 from photodetectors 300 and 310 on the leading edge of signal 336 from photodetector 330 to determine the presence of features 120 and 124. If one or both features are missing, signal 164 is sent to reject actuator 170, suitably delayed based on encoder 180, to remove a defective object from the conveyer.

Basic Operation of Present Invention

Figure 4:
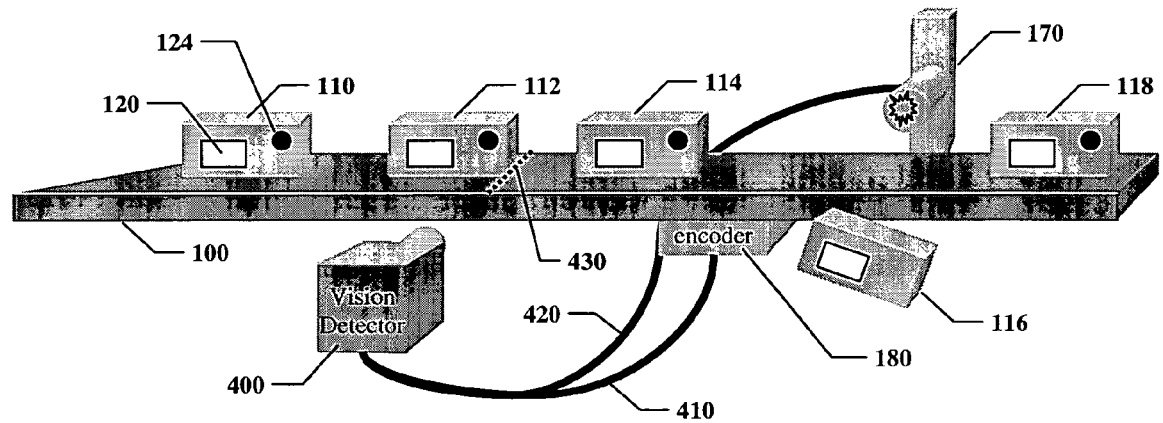
FIG. 4 shows an illustrative embodiment of a vision detector according to the present invention, inspecting objects on a production line.

FIG. 4 shows an illustrative embodiment of a vision detector according to the present invention, inspecting objects on a production line. A conveyer 100 transports objects to cause relative movement between the objects and the field of view of vision detector 400. Objects 110, 112, 114, 116, 118, label 120, hole 124, encoder 180, and reject actuator 170 are as described for FIG. 1. A vision detector 400 detects the presence of an object by visual appearance and inspects it based on appropriate inspection criteria. If an object is defective, the vision detector sends signal 420 to reject actuator 170 to remove the object from the conveyer stream. The encoder 180 sends signal 410 to the vision detector, which uses it to insure proper delay of signal 420 from the encoder count where the object crosses some fixed, imaginary reference point 430, called the mark point. If an encoder is not used, the delay can be based on time instead.

In an alternate embodiment, the vision detector sends signals to a PLC for various purposes, which may include controlling a reject actuator.

In another embodiment, suitable in extremely high speed applications or where the vision detector cannot reliably detect the presence of an object, a photodetector is used to detect the presence of an object and sends a signal to the vision detector for that purpose.

In yet another embodiment there are no discrete objects, but rather material flows past the vision detector continuously, for example a web. In this case the material is inspected continuously, and signals are send by the vision detector to automation equipment, such as a PLC, as appropriate.

When a vision detector detects the presence of discrete objects by visual appearance, it is said to be operating in visual event detection mode. When a vision detector detects the presence of discrete objects using an external signal such as from a photodetector, it is said to be operating in external trigger mode. When a vision detector continuously inspects material, it is said to be operating in continuous analysis mode.

Figure 5:
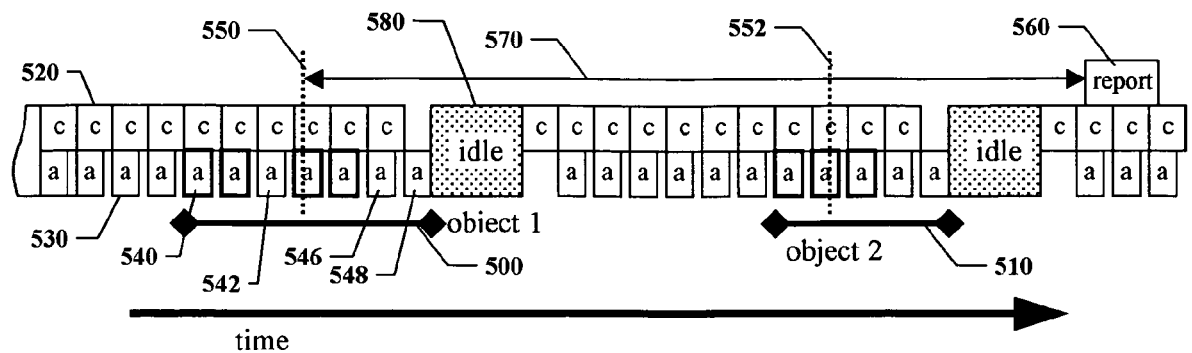
FIG. 5 shows a timeline that illustrates a typical operating cycle for a vision detector using visual event detection.

FIG. 5 shows a timeline that illustrates a typical operating cycle for a vision detector in visual event detection mode. Boxes labeled "c", such as box 520, represent image capture. Boxes labeled "a", such as box 530, represent image analysis. It is desirable that capture "c" of the next image be overlapped with analysis "a" of the current image, so that (for example) analysis step 530 analyzes the image captured in capture step 520. In this timeline, analysis is shown as taking less time than capture, but in general analysis will be shorter or longer than capture depending on the application details.

If capture and analysis are overlapped, the rate at which a vision detector can capture and analyze images is determined by the longer of the capture time and the analysis time. This is the "frame rate".

The present invention allows objects to be detected reliably without a trigger signal, such as that provided by a photodetector 130. Referring to FIG. 4, there is no trigger signal to indicate the presence of an object, and in FIG. 5 there is no corresponding trigger step such as step 220 in FIG. 2.

Referring again to FIG. 5, a portion 500 of the timeline corresponds to the inspection of a first object, and contains the capture and analysis of seven frames. A second portion 510 corresponds to the inspection of a second object, and contains five frames.

Each analysis step first considers the evidence that an object is present. Frames where the evidence is sufficient are called active. Analysis steps for active frames are shown with a thick border, for example analysis step 540. In an illustrative embodiment, inspection of an object begins when an active frame is found, and ends when some number of consecutive inactive frames are found. In the example of FIG. 5, inspection of the first object begins with the first active frame corresponding to analysis step 540, and ends with two consecutive inactive frames, corresponding to analysis steps 546 and 548. Note that for the first object, a single inactive frame corresponding to analysis step 542 is not sufficient to terminate the inspection.

At the time that inspection of an object is complete, for example at the end of analysis step 548, decisions are made on the status of the object based on the evidence obtained from the active frames. In an illustrative embodiment, if an insufficient number of active frames were found then there is considered to be insufficient evidence that an object was actually present, and so operation continues as if no active frames were found. Otherwise an object is judged to have been detected, and evidence from the active frames is judged in order to determine its status, for example pass or fail. A variety of methods may be used to detect objects and determine status within the scope of the invention; some are described below and many others will occur to those skilled in the art.

Once an object has been detected and a judgment made, a report may be made to appropriate automation equipment, such as a PLC, using signals well-known in the art. In such a case a report step similar to step 250 in FIG. 2 would appear in the timeline. The example of FIG. 5 corresponds instead to a setup such as shown in FIG. 4, where the vision detector is used to control a downstream reject actuator 170 via signal 420. By considering the position of the object in the active frames as it passes through the field of view, the vision detector estimates the mark time 550 and 552 at which the object crosses the mark point 430. Note that in cases where an encoder 180 is used, the mark time is actually an encoder count; the reader will understand that time and count can be used interchangeably. A report 560, consisting of a pulse of appropriate duration to the reject actuator 170, is issued after a precise delay 570 in time or encoder count from the mark time 550.

Note that the report 560 may be delayed well beyond the inspection of subsequent objects such as 510. The vision detector uses well-known first-in first-out (FIFO) buffer methods to hold the reports until the appropriate time.

Once inspection of an object is complete, the vision detector may enter an idle step 580. Such a step is optional, but may be desirable for several reasons. If the maximum object rate is known, there is no need to be looking for an object until just before a new one is due. An idle step will eliminate the chance of false object detection at times when an object couldn't arrive, and will extend the lifetime of the illumination system because the lights can be kept off during the idle step.

Figure 6:
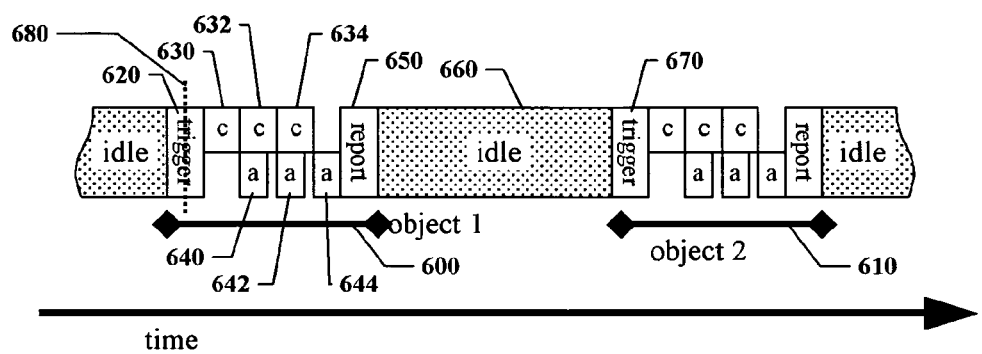
FIG. 6 shows a timeline that illustrates a typical operating cycle for a vision detector using a trigger signal.

FIG. 6 shows a timeline that illustrates a typical operating cycle for a vision detector in external trigger mode. A trigger step 620, similar in function to prior art trigger step 220, begins inspection of a first object 600. A sequence of image capture steps 630, 632, and 634, and corresponding analysis steps 640, 642, and 644 are used for dynamic image analysis. As in visual event detection mode, it is desirable that the frame rate be sufficiently high that the object moves a small fraction of the field of view between successive frames, often no more than a few pixels per frame. After a fixed number of frames, the number being chosen based on application details, the evidence obtained from analysis of the frames is used to make a final judgment on the status of the object, which in one embodiment is provided to automation equipment in a report step 650. Following the report step, an idle step 660 is entered until the next trigger step 670 that begins inspection of a second object 610.

In another embodiment, the report step is delayed in a manner equivalent to that shown in FIG. 5. In this embodiment, the mark time 680 is the time (or encoder count) corresponding to the trigger step 620.

Figure 7:
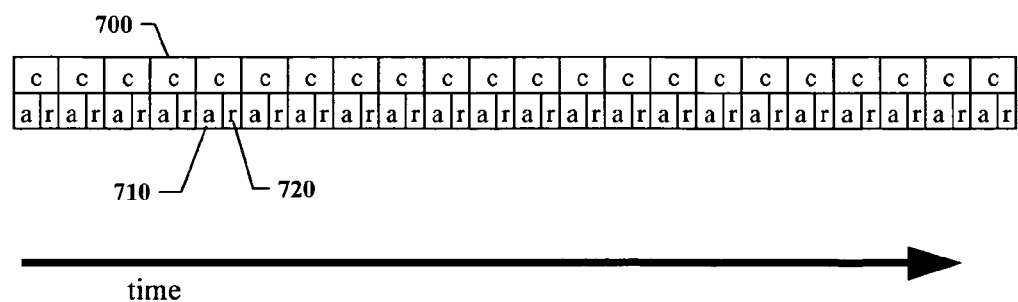
FIG. 7 shows a timeline that illustrates a typical operating cycle for a vision detector performing continuous analysis of a manufacturing process.

FIG. 7 shows a timeline that illustrates a typical operating cycle for a vision detector in continuous analysis mode. Frames are captured, analyzed, and reported continuously. One such cycle comprises capture step 700, analysis step 710, and report step 720.

Illustrative Apparatus

Figure 8:
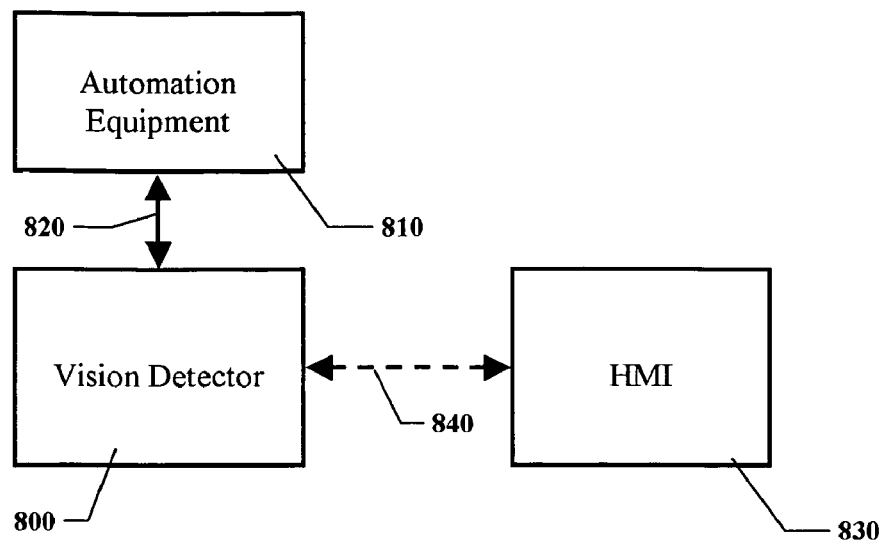
FIG. 8 shows a high-level block diagram for a vision detector in a production environment.

FIG. 8 shows a high-level block diagram for a vision detector in a production environment. A vision detector 800 is connected to appropriate automation equipment 810, which may include PLCs, reject actuators, and/or photodetectors, by means of signals 820. The vision detector may also be connected to a human-machine interface (HMI) 830, such as a PC or hand-held device, by means of signals 840. The HMI is used for setup and monitoring, and may be removed during normal production use. The signals can be implemented in any acceptable format and/or protocol and transmitted in a wired or wireless form.

Figure 9:
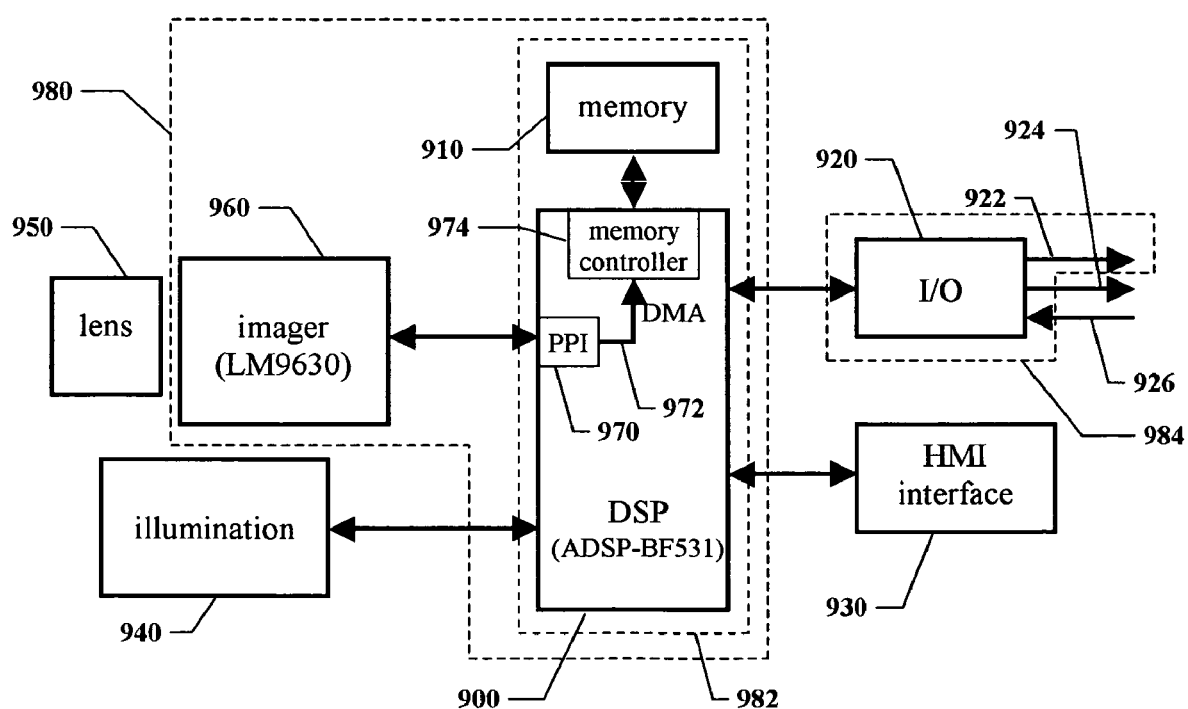
FIG. 9 shows a block diagram of an illustrative embodiment of a vision detector.

FIG. 9 shows a block diagram of an illustrative embodiment of a vision detector. A digital signal processor (DSP) 900 runs software to control capture, analysis, reporting, HMI communications, and any other appropriate functions needed by the vision detector. The DSP 900 is interfaced to a memory 910, which includes high speed random access memory for programs and data and non-volatile memory to hold programs and setup information when power is removed. The DSP is also connected to an I/O module 920 that provides signals to automation equipment, an HMI interface 930, an illumination module 940, and an imager 960. A lens 950 focuses images onto the photosensitive elements of the imager 960.

The DSP 900 can be any device capable of digital computation, information storage, and interface to other digital elements, including but not limited to a general-purpose computer, a PLC, or a microprocessor. It is desirable that the DSP 900 be inexpensive but fast enough to handle a high frame rate. It is further desirable that it be capable of receiving and storing pixel data from the imager simultaneously with image analysis.

In the illustrative embodiment of FIG. 9, the DSP 900 is an ADSP-BF531 manufactured by Analog Devices of Norwood, Mass. The Parallel Peripheral Interface (PPI) 970 of the ADSP-BF531 DSP 900 receives pixel data from the imager 960, and sends the data to memory controller 974 via Direct Memory Access (DMA) channel 972 for storage in memory 910. The use of the PPI 970 and DMA 972 allows, under appropriate software control, image capture to occur simultaneously with any other analysis performed by the DSP 900. Software instructions to control the PPI 970 and DMA 972 can be implemented by one of ordinary skill in the art following the programming instructions contained in the ADSP-BF533 Blackfin Processor Hardware Reference (part number 82-002005-01), and the Blackfin Processor Instruction Set Reference (part number 82-000410-14), both incorporated herein by reference. Note that the ADSP-BF531, and the compatible ADSP-BF532 and ADSP-BF533 devices, have identical programming instructions and can be used interchangeably in this illustrative embodiment to obtain an appropriate price/performance tradeoff.

The high frame rate desired by a vision detector suggests the use of an imager unlike those that have been used in prior art vision systems. It is desirable that the imager be unusually light sensitive, so that it can operate with extremely short shutter times using inexpensive illumination. It is further desirable that it be able to digitize and transmit pixel data to the DSP far faster than prior art vision systems. It is moreover desirable that it be inexpensive and have a global shutter.

These objectives may be met by choosing an imager with much higher light sensitivity and lower resolution than those used by prior art vision systems. In the illustrative embodiment of FIG. 9, the imager 960 is an LM9630 manufactured by National Semiconductor of Santa Clara, Calif. The LM9630 has an array of 128 by 100 pixels, for a total of 12800, about 24 times fewer than typical prior art vision systems. The pixels are relatively large at 20 microns square, providing high light sensitivity. The LM9630 can provide 500 frames per second when set for a 300 microsecond shutter time, and is sensitive enough (in most cases) to allow a 300 microsecond shutter using LED illumination. This resolution would be considered far too low for a vision system, but is quite sufficient for the feature detection tasks that are the objectives of the present invention. Electrical interface and software control of the LM9630 can be implemented by one of ordinary skill in the art following the instructions contained in the LM9630 Data Sheet, Rev 1.0, January 2004, which is incorporated herein by reference.

It is desirable that the illumination 940 be inexpensive and yet bright enough to allow short shutter times. In an illustrative embodiment, a bank of high-intensity red LEDs operating at 630 nanometers is used, for example the HLMP-ED25 manufactured by Agilent Technologies. In another embodiment, high-intensity white LEDs are used to implement desired illumination.

In the illustrative embodiment of FIG. 9, the I/O module 920 provides output signals 922 and 924, and input signal 926. One such output signal can be used to provide signal 420 (FIG. 4) for control of reject actuator 170. Input signal 926 can be used to provide an external trigger.

As used herein an image capture device provides means to capture and store a digital image. In the illustrative embodiment of FIG. 9, image capture device 980 comprises a DSP 900, imager 960, memory 910, and associated electrical interfaces and software instructions.

As used herein an analyzer provides means for analysis of digital data, including but not limited to a digital image. In the illustrative embodiment of FIG. 9, analyzer 982 comprises a DSP 900, a memory 910, and associated electrical interfaces and software instructions.

As used herein an output signaler provides means to produce an output signal responsive to an analysis. In the illustrative embodiment of FIG. 9, output signaler 984 comprises an I/O module 920 and an output signal 922.

It will be understood by one of ordinary skill that there are many alternate arrangements, devices, and software instructions that could be used within the scope of the present invention to implement an image capture device 980, analyzer 982, and output signaler 984.

A variety of engineering tradeoffs can be made to provide efficient operation of an apparatus according to the present invention for a specific application. Consider the following definitions:

b fraction of the FOV occupied by the portion of the object that contains the visible features to be inspected, determined by choosing the optical magnification of the lens 950 so as to achieve good use of the available resolution of imager 960;

e fraction of the FOV to be used as a margin of error;

n desired minimum number of frames in which each object will typically be seen;

s spacing between objects as a multiple of the FOV, generally determined by manufacturing conditions;

p object presentation rate, generally determined by manufacturing conditions;

m maximum fraction of the FOV that the object will move between successive frames, chosen based on above values; and r minimum frame rate, chosen based on above values.

From these definitions it can be seen that $$m \le \frac{1-b-e}{n} \quad (1)$$

and $$r \ge \frac{sp}{m} \quad (2)$$

To achieve good use of the available resolution of the imager, it is desirable that b is at least 50%. For dynamic image analysis, n should be at least 2. Therefore it is further desirable that the object moves no more than about one-quarter of the field of view between successive frames.

In an illustrative embodiment, reasonable values might be b=75%, e=5%, and n=4. This implies that m≦5%, i.e. that one would choose a frame rate so that an object would move no more than about 5% of the FOV between frames. If manufacturing conditions were such that s=2, then the frame rate r would need to be at least approximately 40 times the object presentation rate p. To handle an object presentation rate of 5 Hz, which is fairly typical of industrial manufacturing, the desired frame rate would be at least around 200 Hz. This rate could be achieved using an LM9630 with at most a 3.3 millisecond shutter time, as long as the image analysis is arranged so as to fit within the 5 millisecond frame period. Using available technology, it would be feasible to achieve this rate using an imager containing up to about 40,000 pixels.

With the same illustrative embodiment and a higher object presentation rate of 12.5 Hz, the desired frame rate would be at least approximately 500 Hz. An LM9630 could handle this rate by using at most a 300 microsecond shutter.

In another illustrative embodiment, one might choose b=75%, e=15%, and n=5, so that m≦2%. With s=2 and p=5 Hz, the desired frame rate would again be at least approximately 500 Hz.

Figure 10:
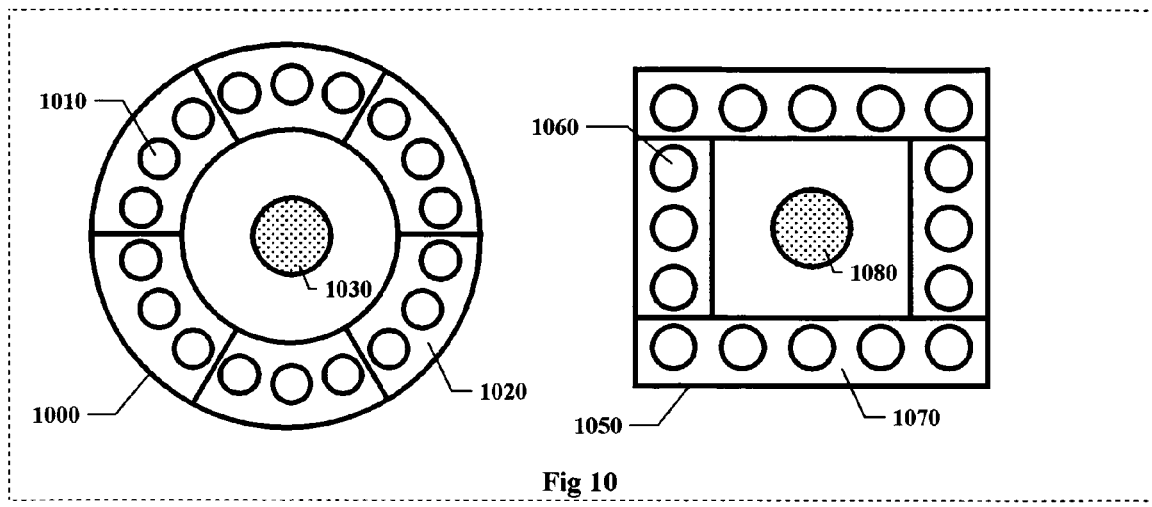
FIG. 10 shows illumination arrangements suitable for a vision detector.

FIG. 10 shows illumination arrangements suitable for a vision detector. In one embodiment, a ring 1000 of 18 LEDs, including exemplary LED 1010, surrounds a lens 1030. The ring is divided into six banks of three LEDs, including example bank 1020, that can be controlled independently. The independent control of the banks allows the illumination direction to be adjusted as appropriate for a given application.

In an alternate embodiment, a rectangular array 1050 of 16 LEDs, including exemplary LED 1060, surrounds a lens 1080. The array is divided into four banks as shown, including example bank 1070.

The capabilities of dynamic image analysis according to the present invention can be enhanced in some cases by controlling the LEDs so that successive frames are captured with varying banks illuminated. By considering the evidence obtained from frames illuminated from varying directions, it is possible to reliably detect features that would be difficult to detect with a fixed illumination direction. Accordingly, the present invention allows analysis utilizing varying direction illumination with moving objects.

Fuzzy Logic Decision Making

Figure 11:
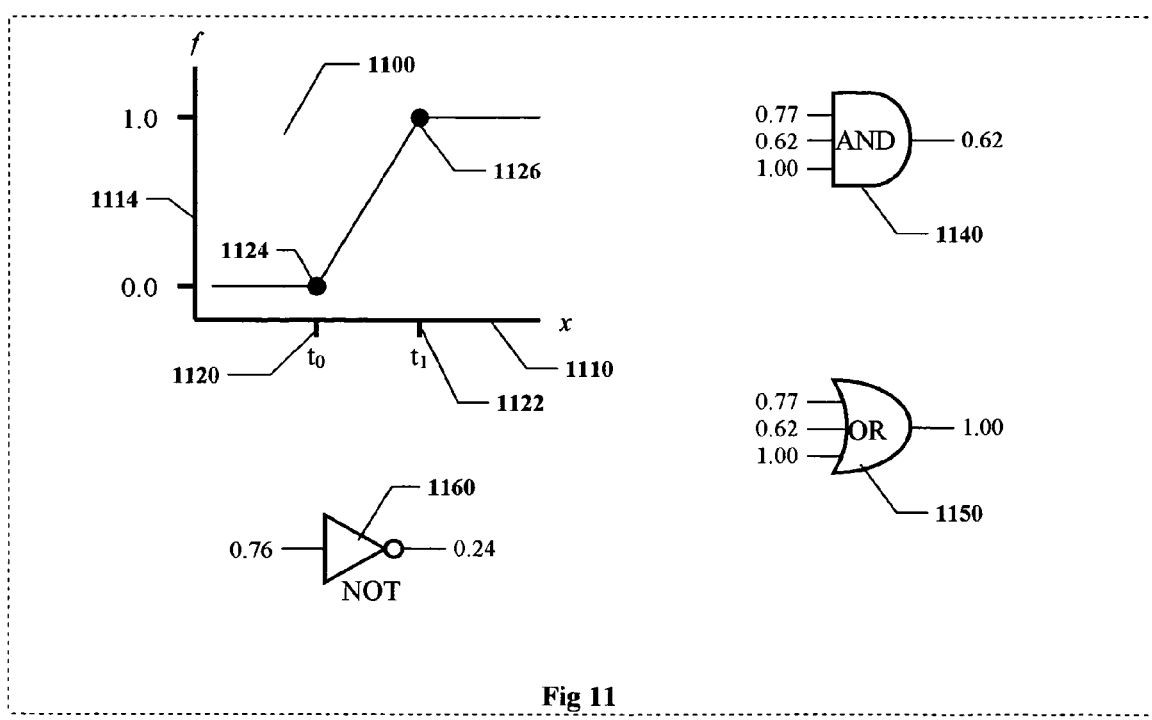
FIG. 11 shows fuzzy logic elements used in an illustrative embodiment to weigh evidence and make judgments, including judging whether an object is present and whether it passes inspection.

FIG. 11 shows fuzzy logic elements used in an illustrative embodiment to weigh evidence and make judgments, including judging whether an object is present and whether it passes inspection.

A fuzzy logic value is a number between 0 and 1 that represents an estimate of confidence that some specific condition is true. A value of 1 signifies high confidence that the condition is true, 0 signifies high confidence that the condition is false, and intermediate values signify intermediate levels of confidence.

The more familiar binary logic is a subset of fuzzy logic, where the confidence values are restricted to just 0 and 1. Therefore, any embodiment described herein that uses fuzzy logic values can use as an alternative binary logic values, with any fuzzy logic method or apparatus using those values replaced with an equivalent binary logic method or apparatus.

Just as binary logic values are obtained from raw measurements by using a threshold, fuzzy logic values are obtained using a fuzzy threshold. Referring to FIG. 11, a graph 1100 illustrates a fuzzy threshold. The x-axis 1110 represents a raw measurement, and the f-axis 1114 represents the fuzzy logic value, which is a function whose domain includes all possible raw measurements and whose range is $0 \leq f \leq 1$.

In an illustrative embodiment, a fuzzy threshold comprises two numbers shown on the x-axis, low threshold to 1120, and high threshold $t_1$ 1122, corresponding to points on the function 1124 and 1126. The fuzzy threshold can be defined by the equation $$f = \min\left(\max\left(\frac{x - t_0}{t_1 - t_0}, 0\right), 1\right) \quad (3)$$

Note that this function works just as well when $t_1 < t_0$. Other functions can also be used for a fuzzy threshold, such as the sigmoid $$f = \frac{1}{1 + e^{-(x-t)/\sigma}} \quad (4)$$

where t and σ are threshold parameters. In embodiments where simplicity is a goal, a conventional binary threshold can be used, resulting in binary logic values.

Fuzzy decision making is based on fuzzy versions of AND 1140, OR 1150, and NOT 1160. A fuzzy AND of two or more fuzzy logic values is the minimum value, and a fuzzy OR is the maximum value. Fuzzy NOT off is 1−f. Fuzzy logic is identical to binary when the fuzzy logic values are restricted to 0 and 1.

In an illustrative embodiment, whenever a hard true/false decision is needed, a fuzzy logic value is considered true if it is at least 0.5, false if it is less than 0.5.

It will be clear to one skilled in the art that there is nothing critical about the values 0 and 1 as used in connection with fuzzy logic herein. Any number could be used to represent high confidence that a condition is true, and any different number could be used to represent high confidence that the condition is false, with intermediate values representing intermediate levels of confidence.

Dynamic Image Analysis

Figure 12:
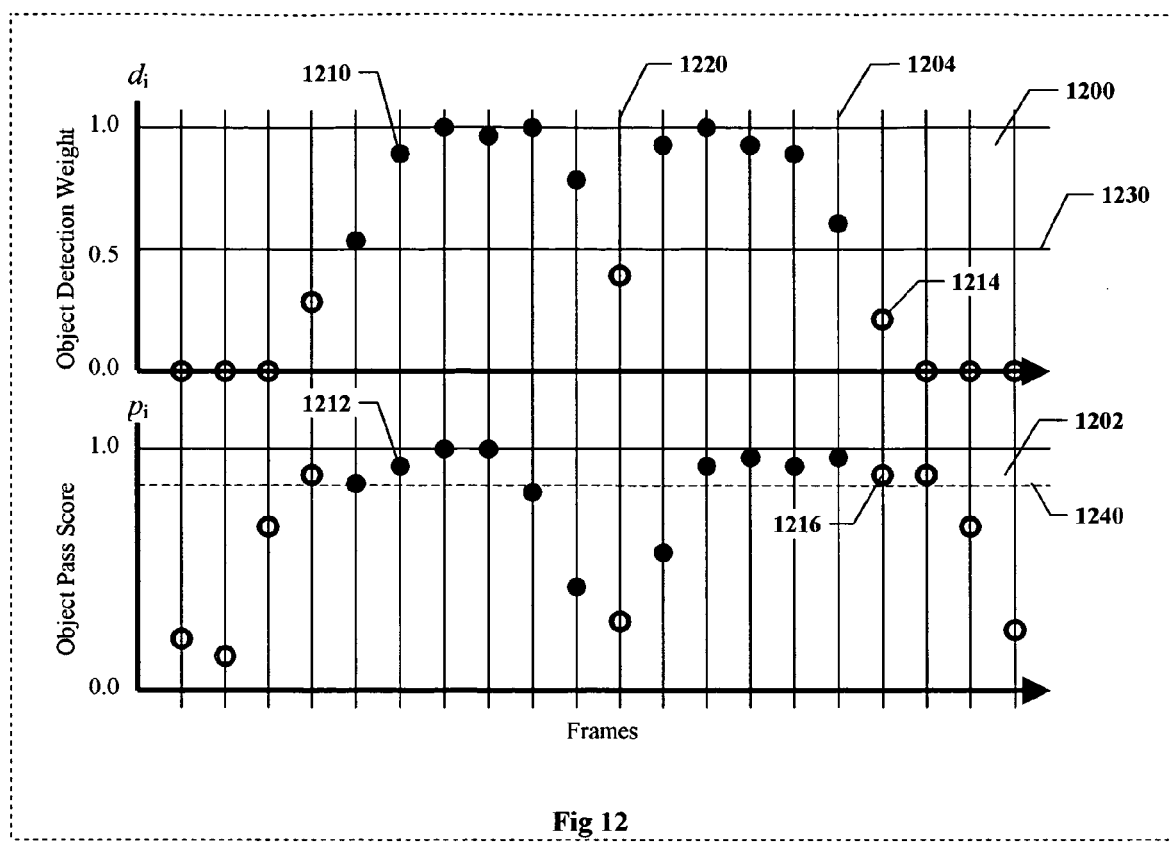
FIG. 12 illustrates how evidence is weighed for dynamic image analysis in an illustrative embodiment.

FIG. 12 illustrates how evidence is weighed for dynamic image analysis in an illustrative embodiment. In this embodiment two decisions, called the primary decisions, must be made:

1. Is an object, or a set of visible features of an object, located in the field of view?
2. If so, what is the status of the object?

Information comprising evidence that an object is located in the field of view is called an object detection weight. Information comprising evidence regarding the status of an object is called an object pass score. In various illustrative embodiments, the status of the object comprises whether or not the object satisfies inspection criteria chosen as appropriate by a user. In the following, an object that satisfies the inspection criteria is sometimes said to "pass inspection".

FIG. 12 shows two plots, object detection plot 1200 and object pass plot 1202. The horizontal axes of the two plots represent a frame sequence number i; each frame is represented by a vertical line, such as example line 1204.

In the illustrative embodiment of FIG. 12, object detection weights are fuzzy logic values $d_i$, representing evidence that an object is located in the FOV in frame i, and are computed by the vision detector on each frame using methods further described below. Object pass scores are fuzzy logic values $p_i$, representing evidence that an object satisfies appropriate inspection criteria in frame i, and are computed by the vision detector on selected frames using methods further described below. The vertical axis of object detection plot 1200 represents $d_i$, and the vertical axis of object pass plot 1202 represents $p_i$.

In the illustrative embodiment of FIG. 12, frames where $d_i \geq 0.5$ are considered active (refer to the above description of FIG. 5 for an explanation of active frames). For reference, a line 1230 where $d_i = 0.5$ is plotted. Object detection weights and pass scores for active frames are plotted as solid circles, for example points 1210 and 1212, and those for inactive frames are plotted as open circles, for example points 1214 and 1216. In some embodiments, the object pass weights are only computed for active frames; while in the embodiment of FIG. 12, they are computed for all frames, whether or not deemed "active".

In the example of FIG. 12, all of the active frames correspond to the inspection of a single object; as explained in the above description of FIG. 5, the isolated inactive frame 1220 does not terminate the inspection.

In one embodiment, an object is judged to have been detected if the number of active frames found exceeds some threshold. An another embodiment, an object is judged to have been detected if the total object detection weight over all active frames exceeds some threshold. These thresholds are set as appropriate for a given application (see FIG. 34).

In the illustrative embodiment of FIG. 12, an object is judged to pass inspection if the weighted average of the object pass scores, each weighted by the corresponding object detection weight, is at least 0.5. More precisely, the object passes inspection if $$\frac{\sum_i d_i p_i}{\sum_i d_i} \geq 0.5 \quad (5)$$

where the summation is over all active frames. The effect of this formula is to average the object pass scores, but to weight each score based on the confidence that the object really did appear in the corresponding frame.

In an alternate embodiment, an object is judged to pass inspection if the average of the object pass scores is at least 0.5. This is equivalent to a weighted average wherein all of the weights are equal.

In the example of FIG. 12, the weighted average pass score is around 0.86, which is plotted as line 1240. The number of active frames is 11, and the total object detection weight is around 9.5. In this example an object is detected and passes inspection.

Figure 13:
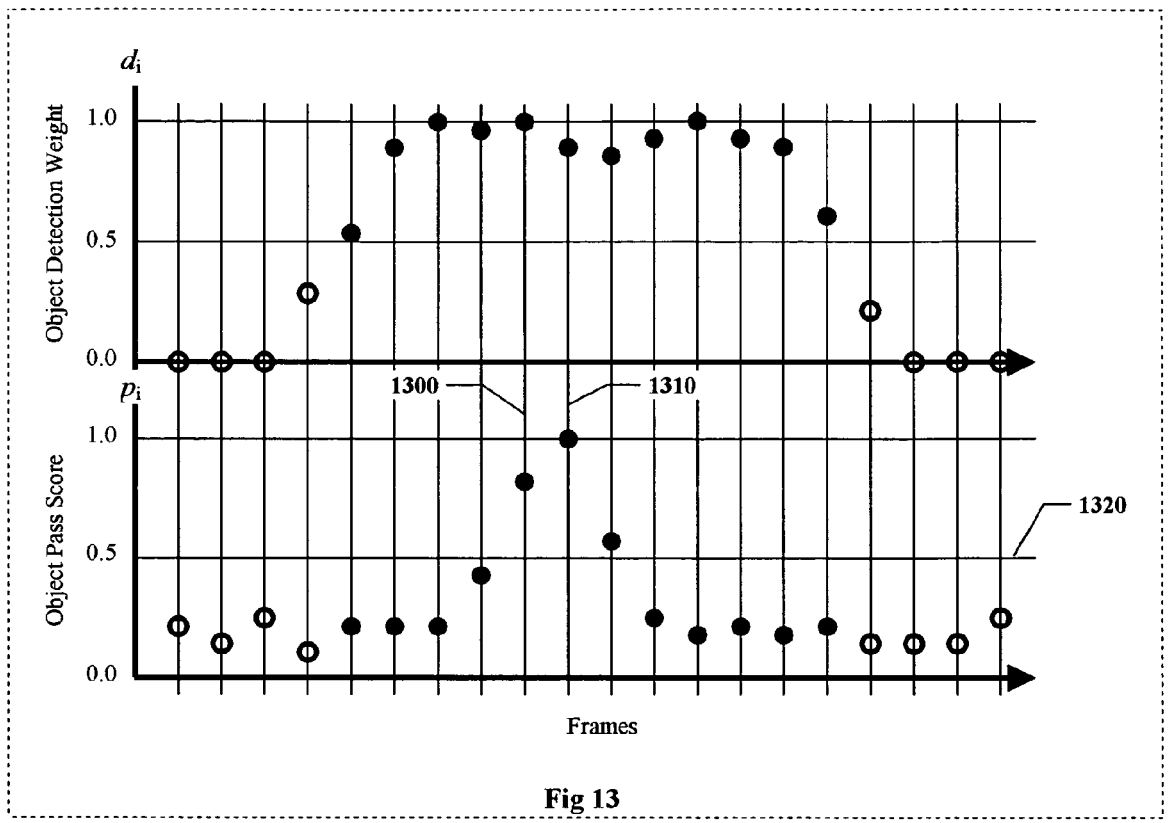
FIG. 13 illustrates how evidence is weighed for dynamic image analysis in another illustrative embodiment.

FIG. 13 illustrates how evidence is weighed for dynamic image analysis in another illustrative embodiment. In this example, object features being inspected are difficult to see and only appear with confidence in a small number of the active frames, primarily frames 1300 and 1310, when the viewing and illumination perspective is just right as the object moves through the field of view. As long as the evidence is sufficient in these few frames that the features are present, the object should pass inspection. In this scenario, there is no way to know in advance which of the active frames will contain this evidence. Thus, weighted average pass score is not appropriate in this case. An alternative is to pass the object if the pass score exceeds some threshold in any of the active frames, but this alternative may pass objects on the basis of too little evidence. In the illustrative embodiment of FIG. 13, a weighted percentile method is used.

The weighted percentile method is based on the fraction Q(p) of total weight where the pass score is at least p:

$$Q(p) = \frac{\sum_{k | p_k \geq p} d_k}{\sum_i d_i} \quad (6)$$

The object is judged to pass if Q(p) is at least some threshold t. In the illustrative embodiment of FIG. 13, p=0.5, which is plotted as line 1320. A reasonable threshold t for this case would be 10%.

Useful behavior is obtained using different values of t. For example, if t=50%, the object is judged to pass inspection if the weighted median score is at least p. Weighted median is similar to weighted average, but with properties more appropriate in some cases. For higher values, for example t=90%, the object will be judged to pass inspection only if the overwhelming majority of the weight corresponds to active frames where the pass score is at least p. For t=100%, the object will be judged to pass inspection only if all of the active frames have a pass score that is at least p. The object may also be judged to pass inspection if Q(p) is greater than 0, which means that any active frame has frame a pass score that is at least p.

In another useful variation, the object is judged to pass inspection based on the total weight where the pass score is at least p, instead of the fraction of total weight.

In an alternate embodiment, a percentile method is used based on a count of the frames where the pass score is at least p. This is equivalent to a weighted percentile method wherein all of the weights are equal.

The above descriptions of methods for weighing evidence to determine whether an object has been detected, and whether it passes inspection, are intended as examples of useful embodiments, but do not limit the methods that can be used within the scope of the invention. For example, the exemplary constants 0.5 used above may be replaced with any suitable value. Many additional methods for dynamic image analysis will occur to those skilled in the art.

Software Elements of the Present Invention

Figure 14:
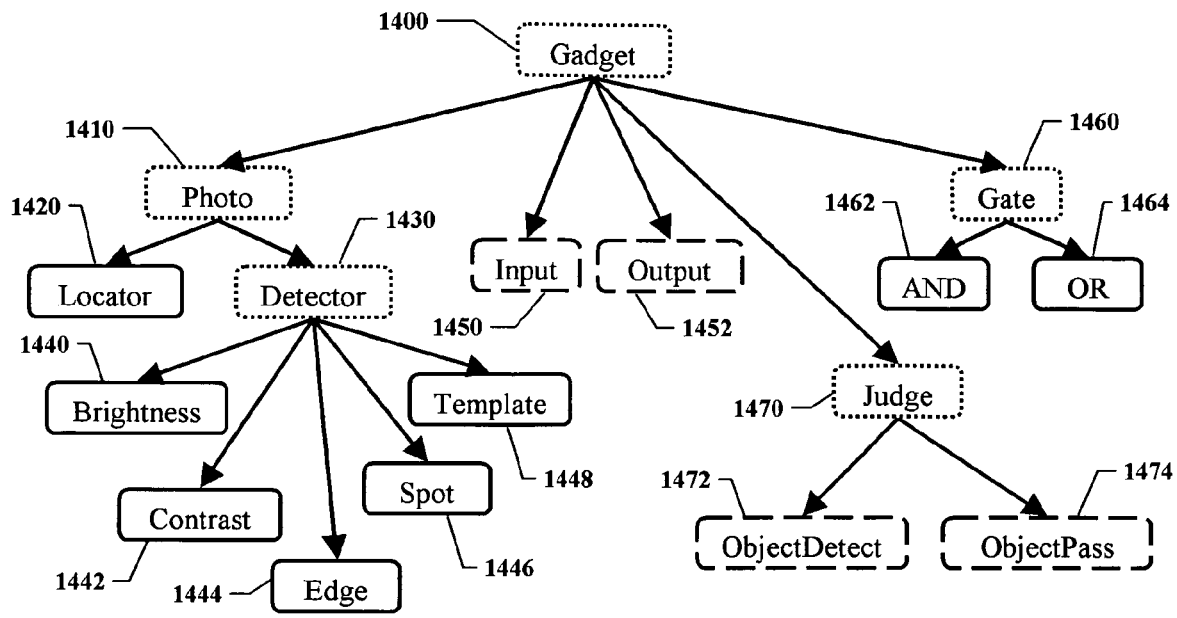
FIG. 14 shows the organization of a set of software elements (e.g., program instructions of a computer readable medium) used by an illustrative embodiment to analyze frames, make judgments, sense inputs, and control output signals.

FIG. 14 shows the organization of a set of software elements (e.g., program instructions of a computer readable medium) used by an illustrative embodiment to analyze frames, make judgments, sense inputs, and control output signals. The elements may be implemented using a class hierarchy in a conventional object-oriented programming language such as C++, so that each of the elements corresponds to a class. However, any acceptable programming technique and/or language can be used to carry out the processes described herein.

As illustrated, classes with a dotted border, such as Gadget class 1400, are abstract base classes that do not exist by themselves but are used to build concrete derived classes such as Locator class 1420. Classes with a solid border represent dynamic objects that can be created and destroyed as needed by the user in setting up an application, using an HMI 830. Classes with a dashed border, such as Input class 1450, represent static objects associated with specific hardware or software resources. Static objects always exist and cannot be created or destroyed by the user.

All classes are derived from Gadget class 1400, and so all objects that are instances of the classes shown in FIG. 14 are a kind of Gadget. In an illustrative embodiment, every Gadget:

1. has a name that can be chosen by the user;
2. has a logic output (a fuzzy logic value) that can be used as a logic input by other gadgets to make judgments and control output signals;
3. has a set of parameters than can be configured by a user to specify its operation;
4. has one such parameter that can be used to invert the logic output (i.e. fuzzy NOT); and
5. can be run, which causes its logic output to be updated based on its parameters, logic inputs if any, and for certain Gadgets the contents of the current frame, and which may also cause side-effects such as the setting of an output signal.

The act of analyzing a frame consists of running each Gadget once, in an order determined to guarantee that all logic inputs to a Gadget have been updated before the Gadget is run. In some embodiments, a Gadget is not run during a frame where its logic output is not needed.

The Photo class 1410 is the base class for all Gadgets whose logic output depends on the contents of the current frame. These are the classes that actually do the image analysis. Every Photo measures some characteristic of a region of interest (ROI) of the current frame. The ROI corresponds to a visible feature on the object to be inspected. This measurement is called the Photo's analog output. The Photo's logic output is computed from the analog output by means of a fuzzy threshold, called the sensitivity threshold, that is among its set of parameters that can be configured by a user. The logic output of a Photo can be used to provide evidence to be used in making judgments.

The Detector class 1430 is the base class for Photos whose primary purpose is to make measurements in an ROI and provide evidence to be used in making judgments. In an illustrative embodiment all Detector ROIs are circles. A circular ROI simplifies the implementation because there is no need to deal with rotation, and having only one ROI shape simplifies what the user has to learn. Detector parameters include the position and diameter of the ROI.

A Brightness Detector 1440 measures a weighted average or percentile brightness in the ROI. A Contrast Detector 1442 measures contrast in the ROI. An Edge Detector 1444 measures the extent to which the ROI looks like an edge in a specific direction. A Spot Detector 1446 measures the extent to which the ROI looks like a round feature such as a hole. A Template Detector 1448 measures the extent to which the ROI looks like a pre-trained pattern selected by a user. The operation of the Detectors is further described below.

The Locator class 1420 represents Photos that have two primary purposes. The first is to produce a logic output that can provide evidence for making judgments, and in this they can be used like any Detector. The second is to determine the location of an object in the field of view of a vision detector, so that the position of the ROI of other Photos can be moved so as to track the position of the object. Any Locator can be used for either or both purposes.

In an illustrative embodiment, a Locator searches a one-dimensional range in a frame for an edge. The search direction is normal to the edge, and is among the parameters to be configured by the user. The analog output of a Locator is similar to that for an Edge Detector. Locators are further described below.

The Input class 1450 represents input signals to the vision detector, such as an external trigger. The Output class 1452 represents output signals from the vision detector, such as might be used to control a reject actuator. There is one static instance of the Input class for each physical input, such as exemplary input signal 926 (FIG. 9), and one static instance of the Output class for each physical output, such as exemplary output signals 922 and 924.

The Gate base class 1460 implements fuzzy logic decision making. Each Gate has one or more logic inputs than can be connected to the logic outputs of other Gadgets. Each logic input can be inverted (fuzzy NOT) by means of a parameter that a user can configure. An AND Gate 1462 implements a fuzzy AND operation, and an OR Gate 1464 implements a fuzzy OR operation.

The Judge class 1470 is the base class for two static objects, the ObjectDetect Judge 1472 and the ObjectPass Judge 1474. Judges implement dynamic image analysis by weighing evidence over successive frames to make the primary decisions. Each Judge has a logic input to which a user connects the logic output of a Photo or, more typically, a Gate that provides a logical combination of Gadgets, usually Photos and other Gates.

The ObjectDetect Judge 1472 decides if an object has been detected, and the ObjectPass Judge 1474 decides if it passes inspection. The logic input to the ObjectDetect Judge provides the object detection weight for each frame, and the logic input to the ObjectPass Judge provides the object pass score for each frame.

The logic output of the ObjectDetect Judge provides a pulse that indicates when a judgment has been made. In one mode of operation, called "output when processing", the leading edge of the pulse occurs when the inspection of an object begins, for example at the end of analysis step 540 in FIG. 5, and the trailing edge occurs when the inspection of an object is complete, for example at the end of analysis step 548. In another mode, called "output when done", the leading edge of the pulse occurs when the inspection of an object is complete, for example at the end of analysis step 548 in FIG. 5, and the trailing edge occurs some time after that, for example at the end of idle step 580.

The logic output of the ObjectPass Judge provides a level that indicates whether the most recently inspected object passed. The level changes state when the inspection of an object is complete, for example at the end of analysis step 548.

Figure 15:
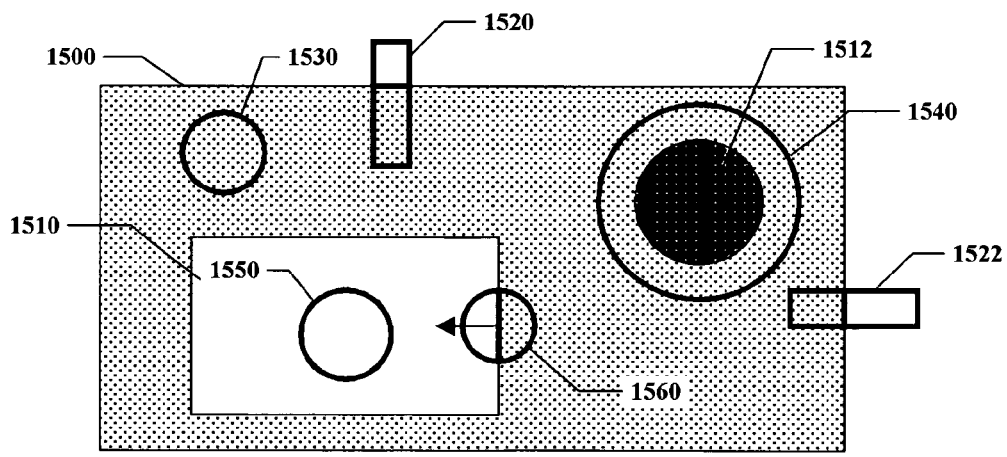
FIG. 15 shows a portion of an exemplary configuration of a vision detector that may be used to inspect an exemplary object.

FIG. 15 shows an example of how Photos can be used to inspect an object. FIG. 15 represents an image of object 110 (from FIG. 1), containing label feature 120 and hole feature 124, with superimposed graphics representing the Photos, and is displayed on an HMI 830 for a user to view and manipulate. A display of an image and superimposed graphics on an HMI is called an image view.

FIG. 15 represents an image view, showing an object 1500 containing a label 1510 and a hole 1512. The object in this example contains 6 visible features to be inspected, corresponding to the two Locators and four Detectors further described below.

A Locator 1520 is used to detect and locate the top edge of the object, and another Locator 1522 is used to detect and locate the right edge.

A Brightness Detector 1530 is used to help detect the presence of the object. In this example the background is brighter than the object, and the sensitivity threshold is set to distinguish the two brightness levels, with the logic output inverted to detect the darker object and not the brighter background.

Together the Locators 1520 and 1522, and the Brightness Detector 1530, provide the evidence needed to judge that an object has been detected, as further described below.

A Contrast Detector 1540 is used to detect the presence of the hole 1512. When the hole is absent the contrast would be very low, and when present the contrast would be much higher. A Spot Detector could also be used.

An Edge Detector 1560 is used to detect the presence and position of the label 1510. If the label is absent, mis-positioned horizontally, or significantly rotated, the analog output of the Edge Detector would be very low.

A Brightness Detector 1550 is used to verify that the correct label has been applied. In this example, the correct label is white and incorrect labels are darker colors.

As the object moves from left to right through the field of view of the vision detector, Locator 1522 tracks the right edge of the object and repositions Brightness Detector 1530, Contrast Detector 1540, Brightness Detector 1550, and Edge Detector 1560 to be at the correct position relative to the object. Locator 1520 corrects for any variation in the vertical position of the object in the field of view, repositioning the detectors based on the location of the top edge of the object. In general Locators can be oriented in any direction.

A user can manipulate Photos in an image view by using well-known HMI techniques. A Photo can be selected by clicking with a mouse, and its ROI can be moved, resized, and rotated by dragging. Additional manipulations for Locators are described below.

Figure 16:
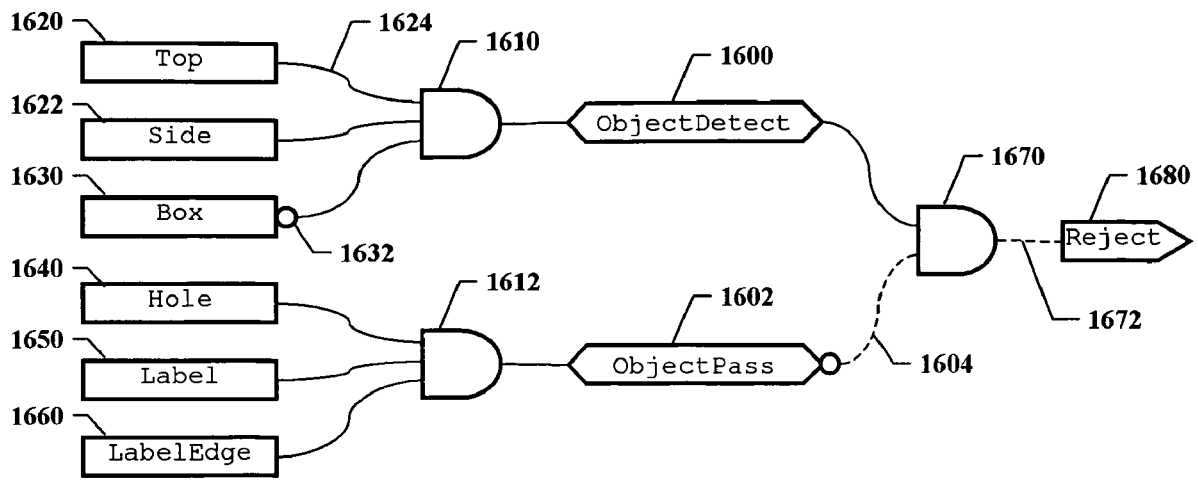
FIG. 16 shows another portion of the configuration corresponding to the exemplary setup of FIG. 15.

FIG. 16 shows a logic view containing a wiring diagram corresponding to the example setup of FIG. 15. A wiring diagram shows all Gadgets being used to inspect objects and interface to automation equipment, and the connections between logic inputs and outputs of the Gadgets. A wiring diagram is displayed on an HMI 830 for a user to view and manipulate. A display of gadgets and their logic interconnections on an HMI is called a logic view.

Referring still to the wiring diagram of FIG. 16, a Locator 1620 named "Top", corresponding to Locator 1520 in the image view of FIG. 15, is connected to AND Gate 1610 by wire 1624. Similarly, "Side" Locator 1622, corresponding to Locator 1522, and "Box" Detector 1630, corresponding to Brightness Detector 1530, are also wired to AND Gate 1610. The logic output of "Box" detector 1630 is inverted, as shown by the small circle 1632 and as described above to detect the darker object against a lighter background.

The logic output of AND Gate 1610 represents the level of confidence that the top edge of the object has been detected, the right edge of the object has been detected, and the background has not been detected. When confidence is high that all three conditions are true, confidence is high that the object itself has been detected. The logic output of AND Gate 1610 is wired to the ObjectDetect Judge 1600 to be used as the object detection weight for each frame.

Since the logic input to the ObjectDetect Judge in this case depends on the current frame, the vision detector is operating in visual event detection mode. To operate in external trigger mode, an Input Gadget would be wired to ObjectDetect. To operate in continuous analysis mode, nothing would be wired to ObjectDetect.

The choice of Gadgets to wire to ObjectDetect is made by a user based on knowledge of the application. In the example of FIGS. 15 and 16, a user may have determined that detecting just the top and right edges was not sufficient to insure that an object is present. Note that Locator 1522 might respond to the label's left edge just as strongly as the object's right edge, and perhaps at this point in the production cycle Locator 1520 might occasionally find some other edge in the background. By adding Detector 1530, and requiring all three conditions by means of AND Gate 1610, object detection is made reliable.

In the wiring diagram, Contrast Detector "Hole" 1640, corresponding to Contrast Detector 1540, Brightness Detector "Label" 1650, corresponding to Brightness Detector 1550, and Edge Detector "LabelEdge" 1660, corresponding to Edge Detector 1560, are wired to AND Gate 1612. The logic output of AND Gate 1612 represents the level of confidence that all three image features have been detected, and is wired to ObjectPass Judge 1602 to provide the object pass score for each frame.

The logic output of ObjectDetect Judge 1600 is wired to AND Gate 1670. The logic output of ObjectPass Judge 1602 is inverted and also wired to AND Gate 1670. The ObjectDetect Judge is set to "output when done" mode, so a pulse appears on the logic output of ObjectDetect Judge 1600 after an object has been detected and inspection is complete. Since the logic output of ObjectPass 1602 has been inverted, this pulse will appear on the logic output of AND Gate 1670 only if the object has not passed inspection. The logic output of AND Gate 1670 is wired to an Output gadget 1680, named "Reject", which controls an output signal from the vision detector than can be connected directly to a reject actuator 170. The Output Gadget 1680 is configured by a user to perform the appropriate delay 570 needed by the downstream reject actuator.

A user can manipulate Gadgets in a logic view by using well-known HMI techniques. A Gadget can be selected by clicking with a mouse, its position can be moved by dragging, and wires can be created by a drag-drop operation.

To aid the user's understanding of the operation of the vision detector, Gadgets and/or wires can change their visual appearance to indicate fuzzy logic values. For example, Gadgets and/or wires can be displayed red when the logic value is below 0.5, and green otherwise. In FIG. 16, wires 1604 and 1672 are drawn with dashed lines to indicate a logic value below 0.5, and other wires, for example wire 1624, are drawn solid to indicate logic values equal to or greater than 0.5.

One skilled in the art will recognize that a wide variety of objects can be detected and inspected by suitable choice, configuration, and wiring of Gadgets. One skilled in the art will also recognize that the Gadget class hierarchy is only one of many software techniques that could be used to practice the invention.

Image Analysis Methods for Detectors

Figure 17:
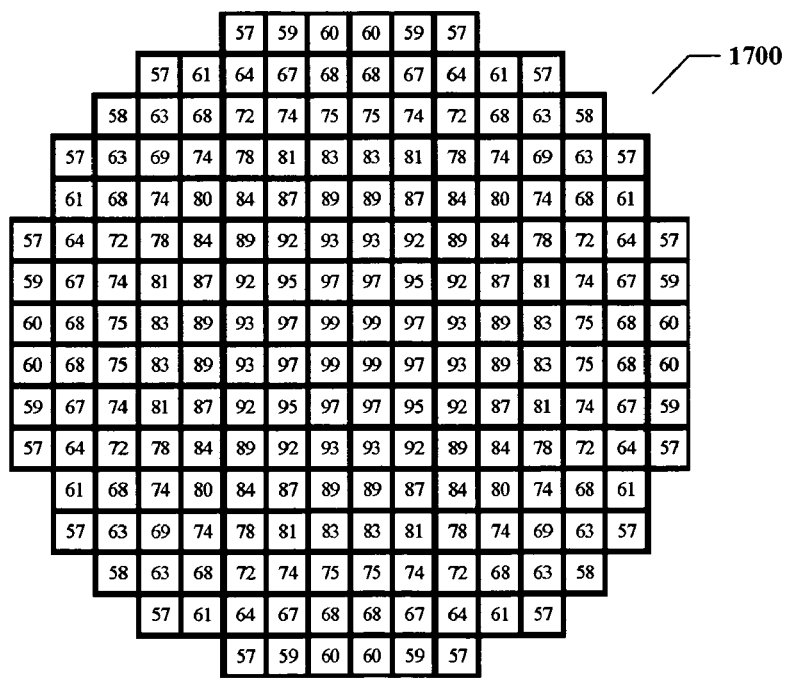
FIG. 17 illustrates a method for analyzing regions of interest to measure brightness and contrast of a visible feature.

FIG. 17 illustrates a method for implementing Brightness and Contrast Detectors. In one embodiment of a Brightness Detector, the analog output is the average gray level within the ROI. In an illustrative embodiment, a kernel of positive weights 1700 is created corresponding to the size and shape of the ROI, and the analog output A is the weighted average gray level $$A = \frac{\sum_i w_i z_i}{\sum_i w_i} \tag{7}$$

where $w_i$ is the $i^{th}$ weight and $z_i$ is the corresponding pixel gray level. In the illustrative embodiment of FIG. 17, the weights approximate a Gaussian function of distance r from the center of the kernel to the center of each weight, $$w(r) = ae^{-\frac{1}{2}(\frac{r}{\sigma})^2} \tag{8}$$

so that pixels near the center are weighted somewhat higher than those near the edge. One advantage of a center-weighted Brightness Detector is that if a bright feature happens to lie near the edge of the Detector's ROI, then slight variations in its position will not cause large variations in the analog output. In FIG. 17 a=99, but any suitable value can be used. The value σ is set based on the diameter d of the kernel, $$\sigma = b\frac{(d-1)}{2} \tag{9}$$

In the illustrative embodiment of FIG. 17, b=1.0.

In another illustrative embodiment, the analog output is defined by the function C(q), which is the gray level such that:

$$\frac{\sum_{k|z_k \leq C(q)} w_k}{\sum_i w_i} = q \tag{10}$$

where q is a percentile chosen by a user. C is the inverse cumulative weighted distribution of gray levels. Various useful values of q are given in the following table:

| q | C(q) |
| --- | --- |
| 0.0 | absolute minimum gray level in ROI |
| 0.1 | statistically reliable minimum gray level |
| 0.5 | weighted median gray level |
| 0.9 | statistically reliable maximum gray level |
| 1.0 | absolute maximum gray level |

In one embodiment of a Contrast Detector, the analog output is the standard deviation of the gray levels within the ROI. In an illustrative embodiment, the array of positive weights 1700 is used to compute a weighted standard deviation:

$$A = \sqrt{\frac{\sum_i w_i \sum_i w_i z_i^2 - \left(\sum_i w_i z_i\right)^2}{\sum_i w_i}} \quad (11)$$

In another illustrative embodiment, the analog output is given by $$C(q_{hi}) - C(q_{lo}) \quad (12)$$

where the q values may be chosen by the user. Useful values are $q_{hi}=0.95$, $q_{lo}=0.05$.

Figure 18:
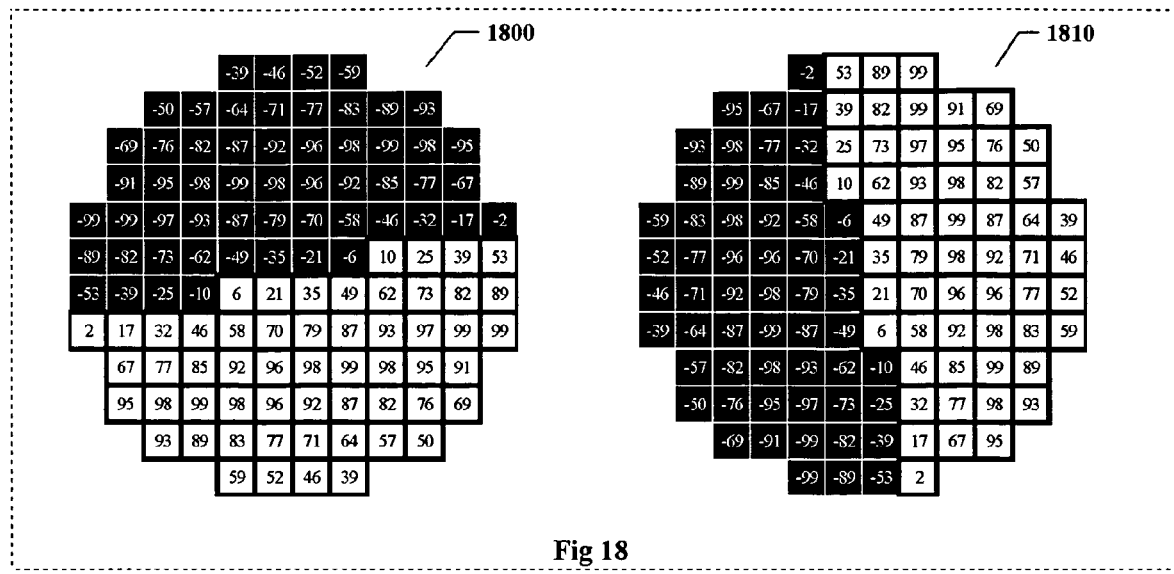
FIG. 18 illustrates a method for analyzing regions of interest to detect step edges.

FIG. 18 illustrates a method for implementing an Edge Detector to detect step edges. A step kernel 1800 is created corresponding to the size and shape of the ROI, and the intended direction of the edge. For step kernel 1800, the ROI is a circle 12 pixels in diameter, and the direction of the edge is 15 degrees from horizontal. The step kernel 1800 is an approximation of the first derivative of a Gaussian function of distance t from the edge to the center of each weight, $$w(r) = \frac{ar}{\sigma} e^{-\frac{1}{2}[(\frac{r}{\sigma})^2 - 1]} \quad (13)$$

In FIG. 18 a=99, but any suitable value can be used. In an illustrative embodiment, equation 9 is used with b=0.5.

The step kernel 1800, with values $k_i$, can be considered to be the product of an ideal step edge template $e_i$ and a kernel of positive weights $w_i$:

$$w_i = |k_i| \quad (14)$$

$$e_i = \frac{k_i}{w_i}$$

$$k_i = e_i w_i$$

Note that the ideal step edge template values $e_i$ are +1 when $k_i > 0$, corresponding to the black on white region of step kernel 1800, and −1 when $k_i < 0$, corresponding to the white on black region of step kernel 1800.

Define contrast C and weighted normalized correlation $R^2$ of the step kernel and a like-shaped ROI with pixel values $z_i$ as follows:

$$v = \sum_i w_i \sum_i w_i z_i^2 - \left(\sum_i w_i z_i\right)^2 \quad (15)$$

$$C = \frac{\sqrt{v}}{\sum_i w_i}$$

$$R^2 = \frac{\left(\sum_i k_i z_i\right)^2}{v}$$

The contrast C uses the standard formula for weighted standard deviation, and $R^2$ uses the standard formula for weighted normalized correlation, but simplified because for step kernel 1800

$$\sum_i w_i e_i = \sum_i k_i = 0 \quad (16)$$

$$\sum_i w_i e_i^2 = \sum_i w_i$$

An orthogonal step kernel 1810 with values $k_i'$ is also created that is identical to the step kernel 1800 but rotated 90 degrees. The ratio $$D = \left|\frac{\sum_i k_i' z_i}{\sum_i k_i z_i}\right| \quad (17)$$

is a reasonable estimate of the tangent of the angle between the actual and expected direction of an edge, particularly for small angles where D is also a good estimate of the angle itself. Note that an orthogonal step template 1810 doesn't need to be created—the values from the step template 1800 can be used, but corresponding to the pixels values in the ROI in a different order.

Figure 19:
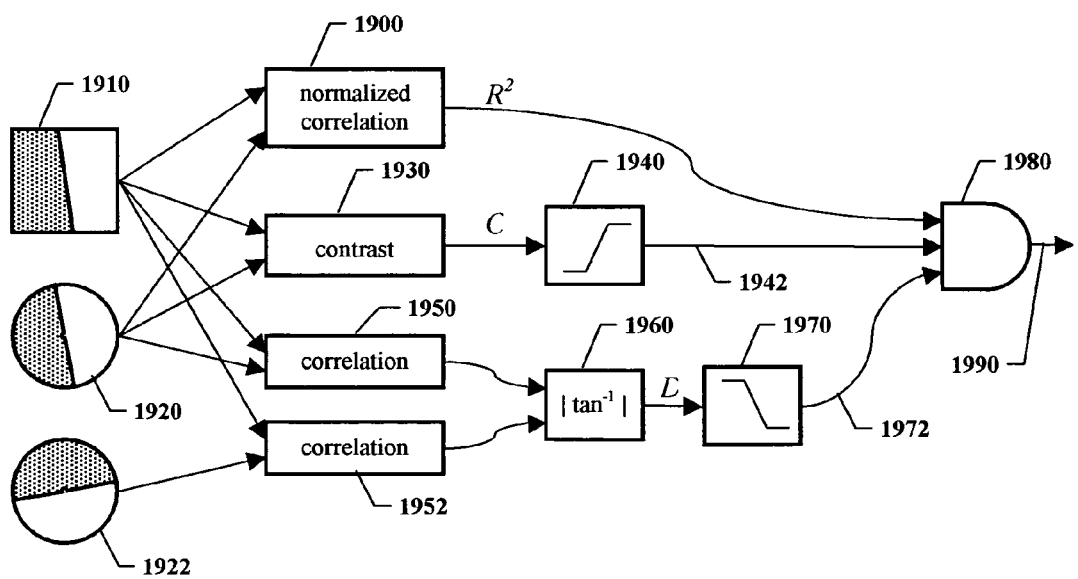
FIG. 19 further illustrates a method for analyzing regions of interest to detect step edges.

FIG. 19 shows how the values R2, C, and D are used to determine the analog output of an illustrative embodiment of the Edge Detector. One can be confident that an edge has been detected when three conditions are met:

1. The ROI looks like an ideal step edge, which means that the weighted normalized correlation $R^2$ of the ideal step edge template and the ROI is high;
2. The contrast C is significantly above some noise threshold; and
3. The angle D is small.

A weighted normalized correlation operation 1900 using ROI 1910 and step kernel 1920 computes $R^2$. A contrast operation 1930 using ROI 1910 and step kernel 1920 computes C, which is converted by fuzzy threshold operation 1940 into a fuzzy logic value 1942 indicating the confidence that the contrast is above the noise level. Weighted correlation operations 1950 and 1952, using ROI 1910, step kernel 1920, and orthogonal step kernel 1922, and absolute value of arctangent of ratio operation 1960, compute D, which is converted by fuzzy threshold operation 1970 into a fuzzy logic value 1972 indicating the confidence that the angle between the expected and actual edge directions is small.

A fuzzy AND element 1980 operates on $R^2$ and fuzzy logic values 1942 and 1972 to produce the analog output 1990 of the Edge Detector. Note that $R^2$, being in the range 0-1, can be used directly as a fuzzy logic value. The analog output 1990 is in the range 0-1, but it can be multiplied by some constant, for example 100, if a different range is desired. Note that the logic output of an Edge Detector is derived from the analog output using the sensitivity threshold that all Photos have.

Figure 20:
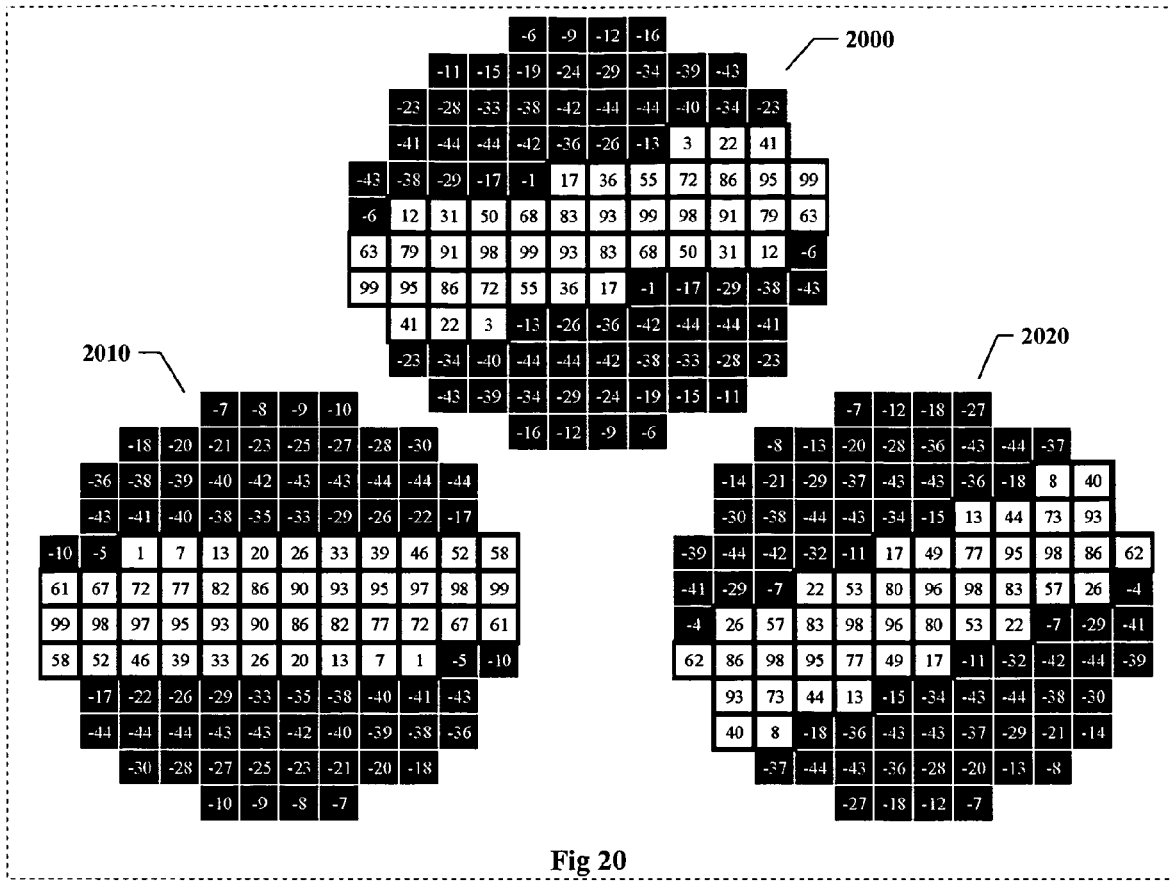
FIG. 20 illustrates a method for analyzing regions of interest to detect ridge edges.

FIG. 20 illustrates a method for implementing an Edge Detector to detect ridge edges. A ridge kernel 2000 is created corresponding to the size and shape of the ROI, and the intended direction θ of the edge. For ridge kernel 2000, the ROI is a circle 12 pixels in diameter, and the direction θ is 15 degrees from horizontal. The ridge kernel 2000 is an approximation of the second derivative of a Gaussian function of distance r from the edge to the center of each weight, $$w(r) = a\left[1 - \left(\frac{r}{\sigma}\right)^2\right]e^{-\frac{1}{2}(\frac{r}{\sigma})^2} \quad (18)$$

In FIG. 20 a=99, but any suitable value can be used. In an illustrative embodiment, equation 9 is used with b=0.33.

The use of ridge kernel 2000 is similar to that for step kernel 1800. The contrast C is computed using the same formula, but $R^2$ uses a different formula because the sum of the kernel values is not 0:

$$R^2 = \frac{\left(\sum_i w_i \sum_i k_i z_i - \sum_i w_i z_i \sum_i k_i\right)^2}{v\left[\left(\sum_i w_i\right)^2 - \left(\sum_i k_i\right)^2\right]} \quad (19)$$

Note that this formula reduces to the one used for step edges when the sum of the kernel values is 0.

A different method is used to determine the angle D between the actual and expected edge directions. A positive rotated ridge kernel 2020 with values $k_i^+$ is created with an edge direction θ+a, and a negative rotated ridge kernel 2010 with values $k_i^-$ is created with an edge direction θ−a. A parabola is fit to the three points $$\left(0, \sum_i k_i z_i\right) \quad (20)$$

$$\left(a, \sum_i k_i^+\right)$$

$$\left(-a, \sum_i k_i^-\right)$$

The x coordinate of the minimum of the parabola is a good estimate of the angle D between the actual and expected edge directions.

Figure 21:
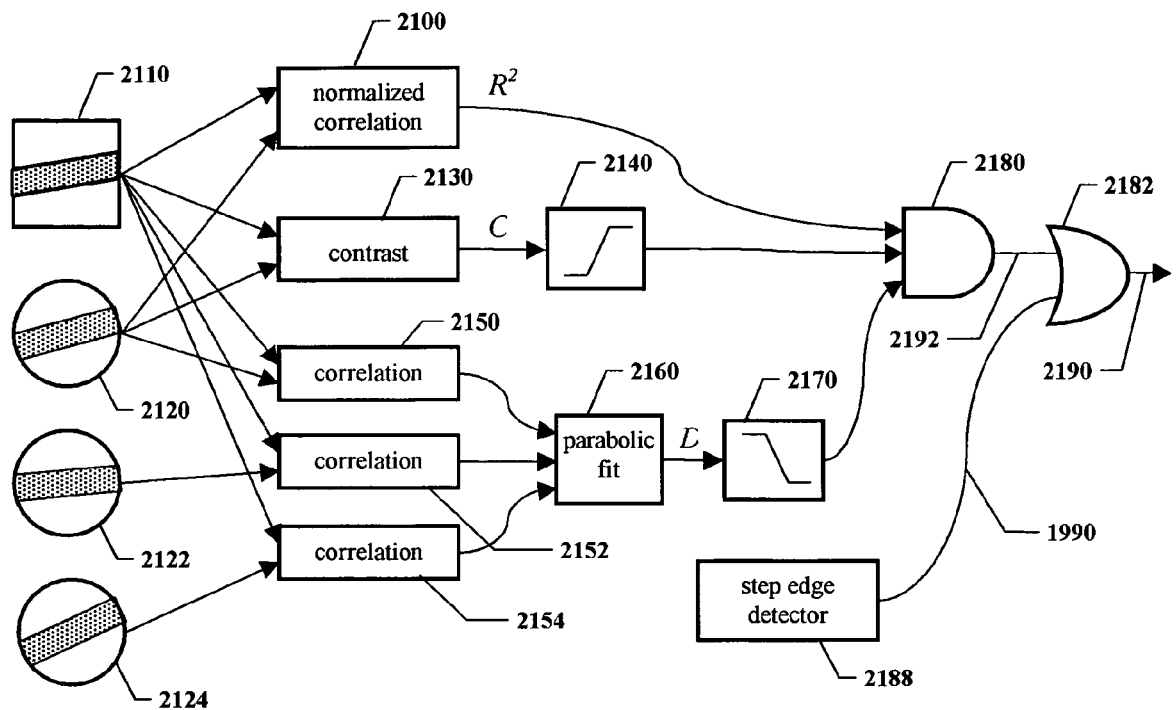
FIG. 21 further illustrates a method for analyzing regions of interest to detect ridge edges, and illustrates a method for detecting either step or ridge edges.

FIG. 21 shows how the ridge kernels are used to determine the analog output of an illustrative embodiment of an Edge Detector that can detect either step or ridge edges. For ridge edge detection, weighted normalized correlation 2100 uses ROI 2110 and ridge kernel 2120 to compute $R^2$. Contrast 2130 uses ROI 2110 and ridge kernel 2120 to compute C, which is then converted to a fuzzy logic value by fuzzy threshold 2140. Correlation elements 2150, 2152, and 2154 use ROI 2110 and ridge kernel 2120, positive rotated ridge kernel 2124, and negative rotated ridge kernel 2122 to provide input to parabolic fit 2160 to compute angle D, which is then converted to a fuzzy logic value by fuzzy threshold 2170.

$R^2$ and the fuzzy logic values are used by fuzzy AND element 2180 to produce a ridge analog output 2192 for an Edge Detector that can detect ridge edges. For an Edge Detector that can detect either step or ridge edges, the ridge analog output 2192 and analog output 1990 from a step edge detector 2188 can be used by fuzzy OR element 2182 to produce a combined analog output 2190.

Figure 22:
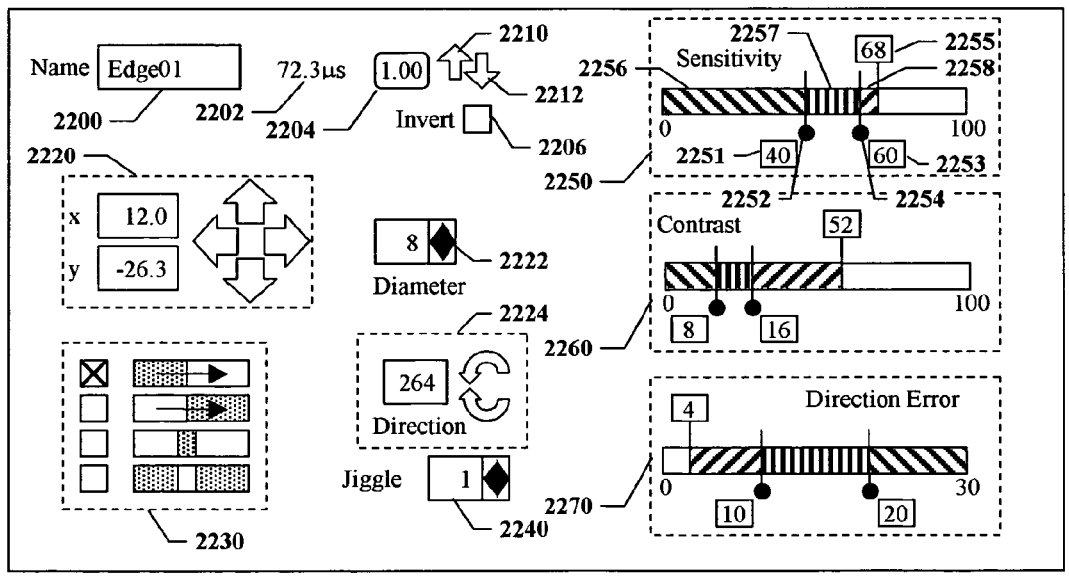
FIG. 22 shows graphical controls that can be displayed on an human-machine interface (HMI) for a user to view and manipulate in order to set parameters for detecting edges.

FIG. 22 shows graphical controls that can be displayed on an HMI for a user to view and manipulate in order to set parameters for an Edge Detector. A set of graphical controls displayed on HMI 830 for setting Gadget parameters is called a parameter view. The parameter view for other Photos is similar enough to FIG. 22 that it would be obvious to one skilled in the art how to construct them.

Name text box 2200 allows a user to view and enter a Gadget's name. Time label 2202 shows the time taken by the most recent run of a Gadget. Logic output label 2204 shows a Gadget's current logic output value, and may change color, shape, or other characteristic to distinguish between true (≧0.5) and false (<0.5). Invert checkbox 2206 allows a Gadget's logic output to be inverted.

Figure 45:
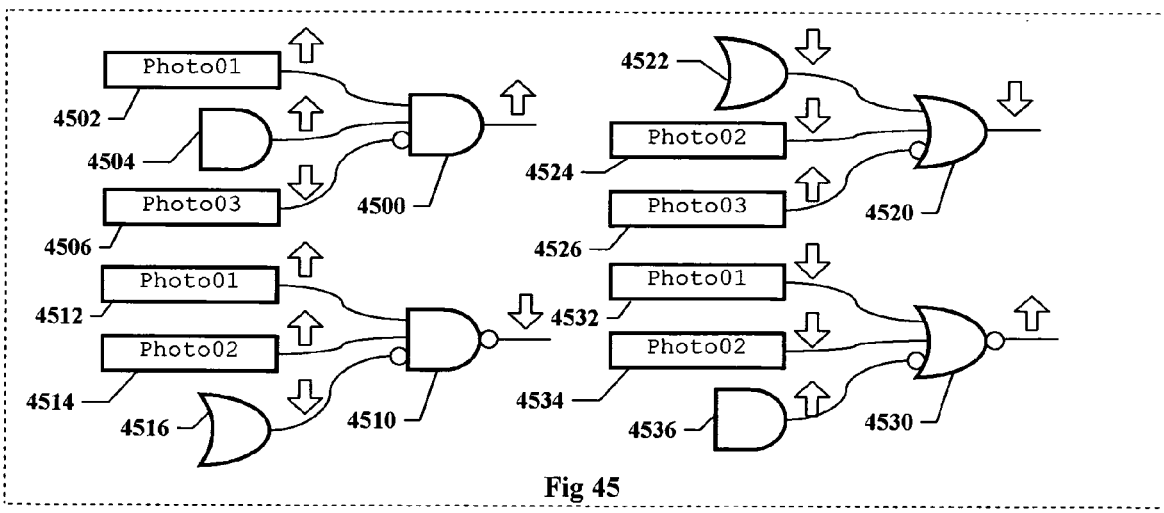
FIG. 45 illustrates rules that are used by an illustrative embodiment of a vision detector for learning appropriate parameter settings based on examples shown by a user.

Thumbs-up button 2210 and thumbs-down button 2212 are used for learning, as further described below (FIG. 45).

Position controls 2220 are used to position a Photo in the field of view. Diameter spinner 2222 is used to change the diameter of a Detector. Direction controls 2224 are used to orient an Edge Detector to the expected edge direction. Position, diameter, and orientation can also be set by manipulation of graphics in an image view, for example the image view of FIG. 15.

Edge type checkboxes 2230 are used to select the types of edges to be detected and the edge polarity. Dark-to-light step, light-to-dark step, dark ridge, and light ridge can be selected. Any combination of choices is allowed, except for choosing none.

Jiggle spinner 2240 allows the user to specify a parameter j such that the Edge Detector will be run at a set of positions ±j pixels around the specified position, and the position with the highest analog output will be used.

Sensitivity threshold controls 2250 allow the user to set the sensitivity fuzzy threshold of a Photo. Zero-point label 2251 shows value to 1120 (FIG. 11), which can be set by zero-point slider 2252. One-point label 2253 shows value $t_1$ 1122, which can be set by one-point slider 2254. Analog output label 2255 shows the current analog output of a Photo. The analog output is also shown graphically by the filled-in region to the left of analog output label 2255, which shrinks and grows like a mercury thermometer lying on its side. The filled-in region can be displayed in three distinct colors or patterns corresponding to a first zone 2256 below to, a second zone 2257 between $t_0$ and $t_1$, and a third zone 2258 above $t_1$.

Contrast threshold controls 2260 allow the user to view the contrast C and set the contrast fuzzy thresholds 1940 and 2140. These controls operate in the same manner as the sensitivity threshold controls 2250.

Direction error controls 2270 allow the user to view the angle between the actual and expected edge directions D and set the direction fuzzy thresholds 1970 and 2170. These controls operate in the same manner as the sensitivity threshold controls 2250, except that the thermometer display fills from right-to left instead of left-to-right because lower values of D correspond to higher fuzzy logic values.

Figure 23:
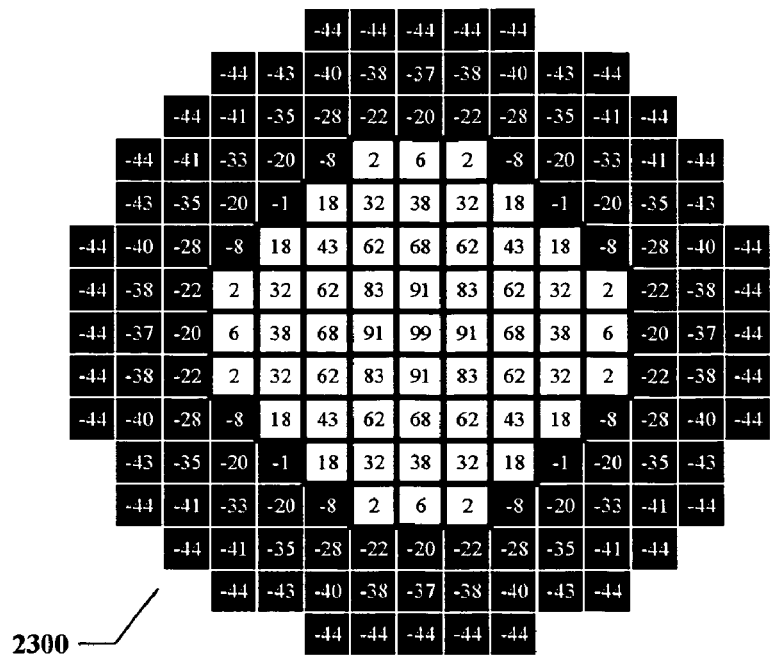
FIG. 23 illustrates a method for analyzing regions of interest to detect spots.

FIG. 23 illustrates a method for implementing a Spot Detector. A spot kernel 2300 is created corresponding to the size and shape of the ROI. For spot kernel 2300, the ROI is a circle 15 pixels in diameter. The spot kernel 2300 is an approximation of the second derivative of a Gaussian function of distance r from the center of the kernel to the center of each weight, using equations 18 and 9. In an illustrative embodiment, b=0.6.

The use of spot kernel 2300 is similar to that for ridge kernel 2000. Weighted normalized correlation $R^2$ and contrast C are computed using the same formulas as was used for the ridge kernel.

Figure 24:
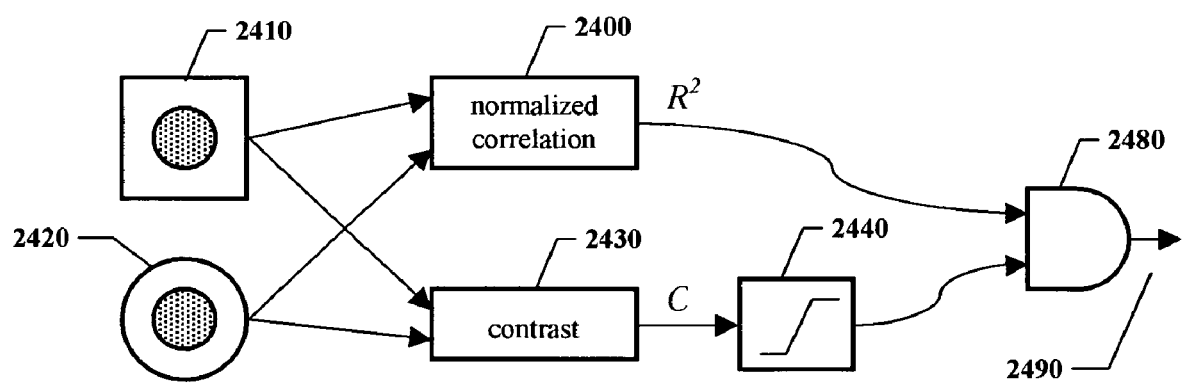
FIG. 24 further illustrates a method for analyzing regions of interest to detect spots.

FIG. 24 shows how the spot kernel is used to determine the analog output of an illustrative embodiment of a Spot Detector. Operation of the Spot Detector is identical to the Edge Detector embodiment shown in FIG. 19, except that angle D is not computed or used. A weighted normalized correlation

2400 uses ROI 2410 and spot kernel 2420 to compute $R^2$. Contrast 2430 uses ROI 2410 and spot kernel 2420 to compute C, which is then converted to a fuzzy logic value by fuzzy threshold 2440. $R^2$ and the fuzzy logic value are used by fuzzy AND element 2480 to produce a spot analog output 2490.

Methods and Human-Machine Interface for Locators

Figure 25:
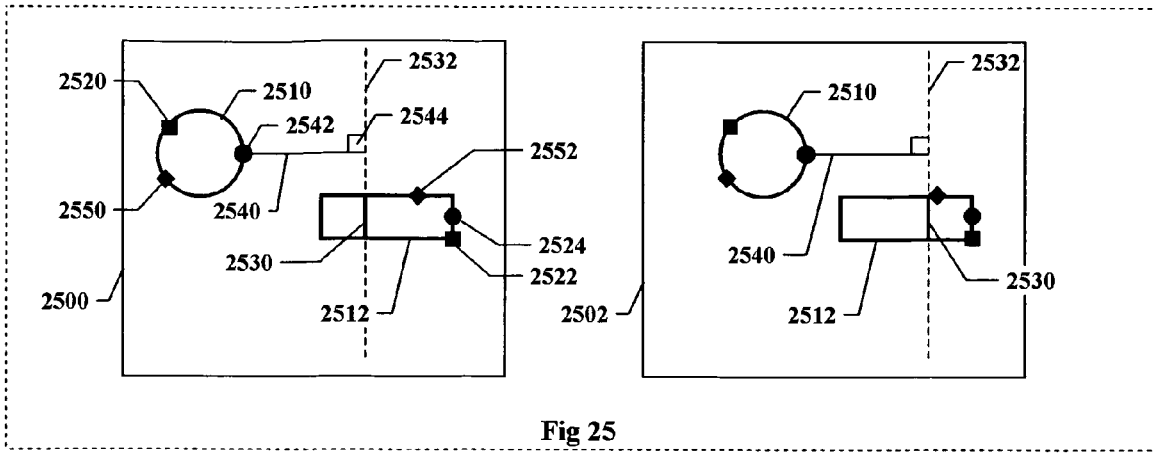
FIG. 25 illustrates a method for analyzing regions of interest to track the location of objects in the field of view, and using an HMI to configure the analysis.

FIG. 25 shows a pair of image views that will be used to describe the operation of Locators according to an illustrative embodiment. In a first image view 2500 and a second image view 2502 there is one Detector 2510 and one Locator 2512. The reader will understand that the following description of Detector 2510 and Locator 2512 applies generally to any Detector and Locator. The reader will further understand that many alternate methods can be devised for configuring Locators within the scope of the invention.

In an illustrative embodiment, a Locator searches a one-dimensional range for an edge, using any of a variety of well-known techniques. The search direction is normal to the edge, and a Locator has a width parameter that is used to specify smoothing along the edge, which is used in well-known ways. The analog output of a Locator depends on the particular method used to search for the edge.

In an illustrative embodiment, a Locator searches a one-dimensional range for an edge using the well-known method of computing a projection of the ROI parallel to the edge, producing a one-dimensional profile along the search range. The one-dimensional profile is convolved with a one-dimensional edge kernel, and the location of the peak response corresponds to the location of the edge. A interpolation, such as the well-known parabolic interpolation, can be used if desired to improve the edge location accuracy. In another embodiment, an edge can be located by searching for a peak analog output using the edge detector of FIG. 19 or FIG. 21, once again interpolating to improve accuracy if desired.

In another embodiment, a Locator searches a multi-dimensional range, using well-known methods, that may include translation, rotation, and size degrees of freedom. It will be clear to one skilled in the art how to employ multi-dimensional Locators to position Photos in practicing the invention, so the following discussion will be limited to one-dimensional Locators, which are preferred due to their simplicity.

Detector 2510 and Locator 2512 can be moved around in the FOV by clicking anywhere on their border and dragging. Detector 2510 has a resize handle 2520 for changing its diameter, and Locator 2512 has a resize handle 2522 for changing its width and range, and a rotate handle 2524 for changing its direction. All Photos can be moved by dragging the border, and have similar handles as appropriate to their operation.

In the illustrative embodiment of FIG. 25, a Locator is drawn in an image view as a rectangle with a inside line segment called the plunger 2530. The width of the Locator is along the plunger, and its range is normal to the plunger. A locator is oriented by a user so that the plunger is approximately parallel to the edge to be found. The rectangle shows the search range, and the plunger shows the location of a detected edge, if any. If no edge is detected, the plunger is drawn in the center of the range.

A Locator has a rail 2532, shown in the Figure as a dashed line, that is coincident with the plunger but extending in both directions to the edge of the image view.

Every Photo can be linked to zero or more locators, up to some maximum number determined by the particular embodiment of the invention. The number of links determines the number of degrees of freedom that the Locators can control. Degrees of freedom include rotation, size, and the two degrees of freedom of translation. In an illustrative embodiment, the maximum number of links is two and only the translation degrees of freedom are controlled.

A linkage defines how a Photo moves as the Locator's plunger moves, following an edge in the image. The movements are defined to keep the Photo at a constant relative distance to the rail or rails of the locators to which it is linked. In an illustrative embodiment the linkages are drawn using a mechanical analogy, such that one could actually build a linkage out of structural elements and bearings and the Photos would move in the same way as forces are applied to the plungers.

In FIG. 25 the linkage from Detector 2510 to Locator 2512 includes a rod 2540, which is rigidly attached to Detector 2510 by a post 2542, and to a slider 2544 that is free to move along the rail 2532, but which holds the rod at right angles to the rail. The post is drawn on the border of a Photo such that the rod, if extended, would pass through the center of the Photo and at the closest of the two possible such points to the rail. A Locator's rail is only shown if there are linkages to it.

Every photo has an emitter, a diamond-shaped handle drawn somewhere on the border. For example Detector 2510 has emitter 2550 and Locator 2512 has emitter 2552. A link is created by drag-dropping a Photo's emitter to any point on a Locator. If the link already exists, the drag-drop might delete the link, or another mechanism for deleting might be used. The user may not create more than the maximum number of allowable links from any Photo, nor any circular dependencies. To aid the user during an emitter drag over a Locator, a tool tip can be provided to tell the user whether a link would be created, deleted, or rejected (and why).

Dragging a Locator does not change the behavior of its plunger—it stays locked on an edge if it can find one, or reverts to the center if not. Thus dragging a locator while an edge is detected just changes its search range; the plunger does not move relative to the FOV. More generally, dragging a Locator never changes the position of any Photo to which it is linked. Dragging a Locator will adjust the rod lengths as necessary to insure that no other Photo moves relative to the FOV.

Any plunger may be dragged manually within the range of its Locator, whether or not it has found an edge, and any linked Photos will move accordingly. This allows users to see the effect of the linkages. As soon as the mouse button is released, the plunger will snap back to its proper position (moving linked Photos back as appropriate).

In FIG. 25 Detector 2510 is linked to one Locator 2512, and so one translation degree of freedom is controlled. The degree of freedom is normal to the edge direction, which means that it is in the direction of rod 2540. Comparing second image view 2502 with first image view 2500, the plunger 2530 has moved to the right as it follows an edge (not shown) in the image. Note that the position in the FOV of Locator 2512 has not changed, but Detector 2510 has moved to the right to follow the plunger, which is following an edge of an object and therefore following the motion of the object itself. In our mechanical analogy, Detector 2510 moves because it is rigidly attached to rail 2532 by rod 2540, and the rail moves with the plunger.

Figure 26:
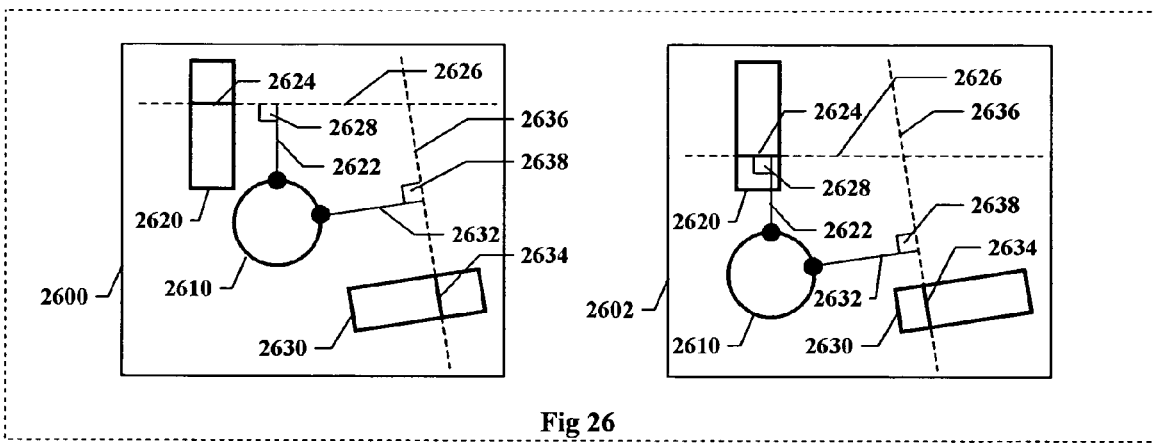
FIG. 26 further illustrates a method for analyzing regions of interest to track the location of objects in the field of view, and using an HMI to configure the analysis.

FIG. 26 shows a pair of image views that will be used to explain the behavior of a Detector linked to two Locators. In a first image view 2600 and a second image view 2602 Detector 2610 is linked to a first Locator 2620 and a second Locator 2630, and so two translation degrees of freedom are controlled. The degrees of freedom are in the direction of first rod 2622 and second rod 2632. Note that the two degrees of freedom are not independent because they are not orthogonal. Handles and emitters are not shown in FIG. 26.

Comparing second image view 2602 with first image view 2600, first plunger 2624 has moved down as it follows a first edge (not shown) in the image, and second plunger 2634 has moved to the left and slightly down as it follows a second edge (not shown). Note that the positions in the FOV of Locators 2620 and 2630 have not changed, but Detector 2610 has moved down and to the left to follow the plungers, which is following the edges of an object and therefore following the motion of the object itself.

In our mechanical analogy, Detector 2610 moves because it is rigidly attached to first rail 2626 by first rod 2622, and to second rail 2636 by second rod 2632. Note that first slider 2628 has slid to the left along first rail 2626, and second slider 2638 has slid down along second rail 2636. The sliders slide along the rails when two non-orthogonal Locators are linked to a Photo.

If a Photo is linked to two nearly parallel Locators, its motion would be unstable. It is useful to set an angle limit between the Locators, below which the linked Photo will not be moved. This state can be indicated in some way in the image view, such as by displaying the two rods using a special color such as red.

The ability to have Locators either at fixed positions or linked to other Locators provides important flexibility. In FIG. 26 neither Locator is linked and so they remain at fixed positions in the FOV, and therefore at fixed positions relative to the illumination, which is often desirable.

Figure 27:
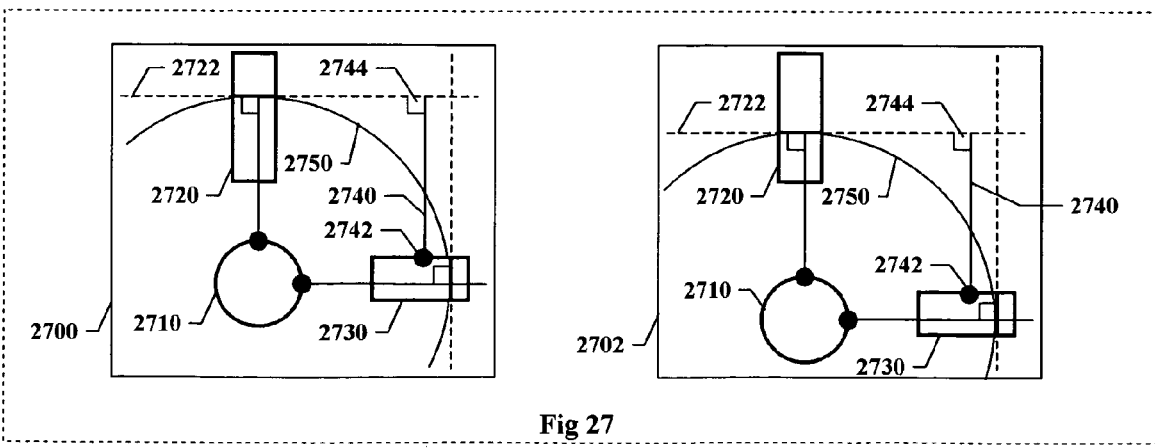
FIG. 27 further illustrates a method for analyzing regions of interest to track the location of objects in the field of view, and using an HMI to configure the analysis.

FIG. 27 shows a pair of image views that will be used to explain the behavior of a Detector linked to two Locators, where one of the Locators in linked to the other. In a first image view 2700 and a second image view 2702 Detector 2710 is linked to a first Locator 2720 and a second Locator 2730. Second Locator 2730 is also linked to first Locator 2720 via rod 2740, post 2742, and slider 2744. Slider 2744 slides along rail 2722 of first locator 2720.

Note that there need be no limit on the number of Photos that can be linked to a Locator; the degree of freedom limit is on the number of links one Photo can have to Locators. In the example of FIG. 27, Detector 2710 is linked to two Locators and is controlled in two translation degrees of freedom. Second Locator 2730 is linked to one Locator and is controlled in one translation degree of freedom. First Locator 2720 is linked to no Locators and remains fixed in the FOV.

The Locators are configured to follow the top and right edges of a circular feature 2750. Comparing second image view 2702 with first image view 2700, the circular feature 2750 has moved down, causing rail 2722 to move down to follow it. This moves both Detector 2710 and second Locator 2730 down. Note that Detector 2710 is at the same position relative to the object, and so is second Locator 2730. This is desirable in this case, because if second Locator 2730 were fixed in the FOV, it might miss the right edge of circular feature 2750 as it moves up and down. Note that this would not be problematic if the edge of an object in the image was a straight line.

First Locator 2720 has no Locator to move it left and right so as to find the top edge of circular feature 2750. It can't link to second Locator 2730 because that would create a circular chain of links, which is not allowed because one Locator has to run first and it can't be linked to anything. Instead, the motion of the object through the FOV insures that first Locator 2720 will find the top edge. In the example of FIG. 27 the motion is left to right, and due to the high frame rate of a vision detector the object moves only slightly each frame. Eventually, first Locator 2720 will find the top edge, and will do so on a number of frames, depending on the speed of the object, where the top of circular feature 2750 is close to the center of the Locator. On those frames, second Locator 2730 will be positioned properly to find the right edge, and it will move Detector 2710 left and right as needed to keep it in the right position.

Figure 28:
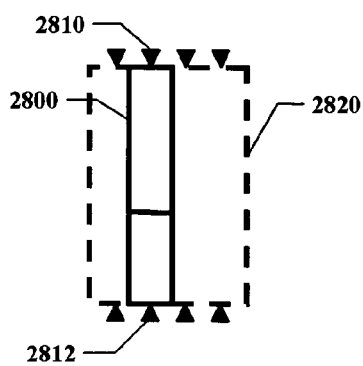
FIG. 28 illustrates a method for analyzing regions of interest to track the location of objects in the field of view, and using an HMI to configure the analysis, in certain cases where placement of the regions of interest must be fairly precise along an object boundary.

FIG. 28 shows a method for handling cases where the edge to be found by a Locator does not extend in a straight line, and so placement of the locator must be fairly precise along the object boundary. This method could be used for first Locator 2720 in FIG. 27 in an application where objects move at very high speed, and so there might be a chance of missing the top edge entirely as the object moves through the FOV.

To handle cases like this, Locators have a parameter that can be used to specify the number of parallel sweeps to be made in searching for the edge. The sweeps are spaced apart along the edge by an amount that provides sufficient overlap so that the edge won't fall between the cracks of the sweeps.

FIG. 28 shows a Locator 2800 with four sweeps that has found an edge on the second sweep from the left. Triangular-shaped sweep markers, including example sweep markers 2810 and 2812, are shown outside the dashed sweep rectangle 2820 to avoid interference from the locator graphics within. If an edge is not found on any of the sweeps, the Locator reverts to the center of the sweep rectangle (which won't be at a sweep marker for even sweep counts).

Figure 29:
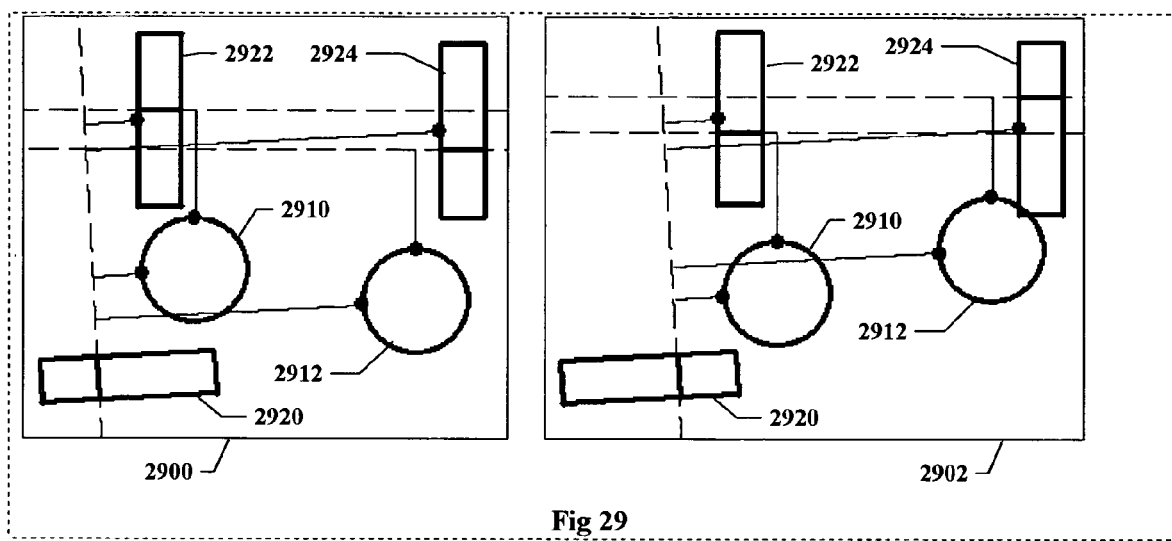
FIG. 29 illustrates a method for analyzing regions of interest to track the location of objects in the field of view, and using an HMI to configure the analysis, in cases where objects may rotation and change size.

FIG. 29 shows how Locators can be used to handle object rotation and size change even in embodiments where only two translation degrees of freedom are controlled. The restriction to translation only provides considerable simplicity and transparency for the user, but small object rotation and size changes can still be handled since Photos in different parts of the FOV can translate differently in response to different Locators. Small rotations and size changes are well-approximated by translations within a small region of the FOV, so as long as Photos are linked to at least one nearby Locator, object rotation and size change will look like translation.

Referring still to FIG. 29, a first image view 2900 and a second image view 2902 contain a first Detector 2910, a second Detector 2912, a first Locator 2920, a second Locator 2922, and a third Locator 2924.

First Detector 2910 is linked to nearby first Locator 2920 and second Locator 2922, and will be positioned properly even if the object rotates or changes size (as long as the change is not too big). But second Detector 2912 is too far away—a rotation would tend to mis-position second Detector 2912 vertically relative to second Locator 2922, and a size change would tend to mis-position it horizontally relative to first Locator 2920. Third Locator 2924 is used instead of second Locator 2922 to get the vertical position of second Detector 2912, allowing overall object rotation to be handled. The remote first Locator 2920 is used to get horizontal position for second Detector 2912, so the object size should not vary much. If size variation needs to be handled in addition to rotation, one would add a fourth Locator, near second Detector 2912 and oriented horizontally.

Comparing second image view 2902 with first image view 2900, the object (not shown) has moved to the right and rotated counterclockwise, which can be seen by the motion of the Detectors as the Locators follow the object edges. Note that second Locator 2922 and third Locator 2924 are linked to first Locator 2920 so that they stay close to the Detectors.

Alternate Logic View using Ladder Diagrams

FIG. 30 shows an alternative representation for a logic view, based on a ladder diagram, a widely used industrial programming language. The ladder diagram of FIG. 30 is essentially equivalent to the wiring diagram shown in FIG. 16, in that it represents the same set of Gadgets and their logic interconnections. In an illustrative embodiment, a user can switch the logic view between a wiring diagram and a ladder diagram at will, and can manipulate and edit either diagram.

In an illustrative embodiment, to render a ladder diagram for a configuration of Gadgets one rung is created for each Gadget that has logic inputs: Gates, Judges, and Outputs. The order of the rungs is the automatically determined run order for the Gadgets. Each rung consists of one contact for each logic input, followed by an icon for the Gadget. Contacts are normally open for non-inverted connections and normally closed for inverted connections. For AND Gates the contacts are in series, and for OR Gates the contacts are in parallel. Labels associated with each contact indicate the name of the Gadget that is connected to the logic input.

To simplify the ladder diagram, the user may choose to hide any Gate whose logic output is connected to exactly one logic input of another Gadget via a non-inverted connection. When a Gate is hidden, the rung for that Gate is not displayed. Instead the contacts for that Gate replace the normally open contact that would have appeared on the one rung in which that Gate is used.

Referring to FIG. 30, rung 3000 shows the inputs to Object-Detect Judge 3002, rung 3010 shows the inputs to ObjectPass Judge 3012, and rung 3020 shows the inputs to Output Gadget 3022 named "Reject". Normally open contacts Top 3030 and Side 3032, and normally closed contact Box 3034, represent the inputs to AND Gate 1610 (FIG. 16), which has replaced the contact that would have appeared on rung 3000 because AND Gate 1610 is connected to exactly one logic input via a non-inverted connection.

Similarly, rung 3010 shows normally open contacts Hole 3040, Label 3042, and LabelEdge 3044 connected to an AND Gate (hidden AND Gate 1612), whose output is connected to ObjectPass Judge 3012.

Rung 3020 shows normally open contact 3050 and normally closed contact 3052 connected to an AND Gate (hidden AND Gate 1670), whose output is connected to Output Gadget 3022 named "Reject".

Note that the ladder diagrams used by the above-described embodiment of the invention are a limited subset of ladder diagrams widely used in industry. They are provided primarily to aid users who are familiar with ladder diagrams. The subset is chosen to match the capabilities of wiring diagrams, which simplifies the implementation and also allows a user to choose between wiring and ladder diagrams as need arises.

In another embodiment, a more complete implementation of ladder diagrams is provided and wiring diagrams are not used. The result combines the capabilities of a vision detector with those of a PLC, resulting in a powerful industrial inspection machine but at a cost of increased complexity.

Marking, Synchronized Outputs, and Related Measurements

FIG. 31 shows a timing diagram that will be used to explain how vision detector output signals may be synchronized with the mark time. Signal synchronization is desirable for a variety of industrial inspection purposes, such as control of a downstream reject actuator. The requirements for these signals depends on how objects are presented and how they are detected.

As discussed above, objects are detected either by visual event detection or external trigger (continuous analysis mode is used when there are no discrete objects). Furthermore, objects may be presented either by indexing, in which case they come to a stop in the FOV, or continuous motion. When using an external trigger the analysis is typically the same regardless of how objects are presented. For visual event detection, however, the analysis may depend on whether the object will come to a stop (indexing) or be in roughly uniform motion (continuous). For example, a vision detector may not be able to measure or use object speed in an indexed application.

Visual event detection is a novel capability and suggests novel output signal control, particularly when continuous object presentation is used. It is desirable that a vision detector be able to control some external actuator, either directly or by serving as input to a PLC. This suggests, for continuous presentation at least, that the timing of output signals be related with reasonable precision to the point in time when the object passed a particular, fixed point in the production flow. In the example of FIG. 4 the fixed point is mark point 430, and in the timelines of FIGS. 5 and 6 the time is mark times 550, 552, and 680. In FIG. 31, the time is mark time 3100. Note that an encoder count may be used instead of time.

For prior art vision systems this goal is addressed by the external trigger, which is typically a photodetector that responds within microseconds of the mark time. This signal, which triggers the vision system (e.g. signal 166 in FIG. 1), is also used by a PLC (signal 162) to synchronize vision system outputs with a downstream actuator. The vision system outputs come many milliseconds later, at a time that is far too variable to be used without synchronization.

The present invention, when used in visual event detection mode, can provide outputs synchronized to reasonable precision with the mark time, whether it controls the actuator directly or is used by a PLC. One concern, however, is that like a vision system and unlike a photodetector, a vision detector makes its decision about the object many milliseconds after the mark time. Furthermore, the delay may be quite variable, depending on how many frames were analyzed and, to a lesser extent, when in the acquire/process cycle the mark time occurs.

FIG. 31 shows the ObjectDetect logic output 3140 and the ObjectPass logic output 3150. Note that the ObjectDetect Judge is in "output when done" mode, which is the mode used for output signal synchronization. ObjectPass logic output 3150 changes state, and a detect pulse 3170 appears on ObjectDetect logic output 3140, when the decision is made at decision point 3110. Note that the decision delay 3130 from mark time 3100 to the decision point 3110 may be variable.

If ObjectDetect logic output 3140 and ObjectPass logic output 3150 are wired to an AND Gate, a pulse (not shown) will be produced only when an object that passes inspection is detected. If the logic output of ObjectPass is inverted, the AND Gate will produce a pulse (not shown) only when an object that fails inspection is detected.

The detect pulse 3170, and pulses indicating passing object detected and failing object detected, are all useful. In an indexed application they might be used directly by actuators. A PLC can use an external trigger to synchronize these pulses with actuators. But when objects are in continuous motion and no external trigger is used, the pulses often cannot be used directly to control actuators because of the variable decision delay 3130.

The invention solves this problem by measuring the mark time 3100 and then synchronizing an output pulse 3180 on output signal 3160 to it. The output pulse 3180 occurs at a fixed output delay 3120 from mark time 3100. Referring also to the timing diagram in FIG. 5, output pulse 3180 is an example of a report step 560, and output delay 3120 corresponds to delay 570.

The act of measuring the mark time is called marking. The mark time can be determined to sub-millisecond accuracy by linear interpolation, least-squares fit, or other well-known methods, using the known times (counts) at which the images were captured and the known positions of the object as determined by appropriate Locators. Accuracy will depend on shutter time, overall acquisition/processing cycle time, and object speed.

In an illustrative embodiment a user chooses one Locator whose search range is substantially along the direction of motion to be used for marking. The mark point is arbitrarily chosen to be the center point of the Locator's range—as discussed above, the mark point is an imaginary reference point whose exact position doesn't matter as long as it is fixed. The user can achieve the desired synchronization of output signals by adjusting the delay from this arbitrary time. If an object is detected that does not cross the mark point during the active frames, the mark time can be based on an extrapolation and the accuracy may suffer.

The user may as an alternative specify that the mark time occurs when the object is first detected. This option might be selected in applications where Locators are not being used, for example when visual event detection relies on Detectors placed in fixed positions in the FOV (see FIG. 44). Marking at the point of first detection might be less accurate than when locators are used, although in some applications it may be possible to improve accuracy by interpolating the fuzzy logic values input to the ObjectDetect Judge to find the time at which the value crosses 0.5.

Note that output signals can only be synchronized to the mark time if output delay 3120 is longer than the longest expected decision delay 3130. Thus the actuator should be sufficiently downstream of the mark point, which is expected to be the case in almost all applications.

When an external trigger is used, the mark time is relative to the time at which the trigger occurs (e.g. mark time 680 in FIG. 6). Output pulse 3180 can be synchronized to this time for direct control of a downstream actuator. When using an external trigger and a PLC, which is how prior art vision systems are used, marking can be used but is generally not necessary.

FIG. 32 shows an example of measuring the mark time in visual event detection mode, and also measuring object speed, pixel size calibration, and object distance and attitude in space. Each column in the Figure corresponds to one frame captured and analyzed by the invention, except for the first column which serves to label the rows. Frame row 3210 is a frame number that serves to identify the frame. Time row 3220 shows the time in milliseconds that the frame was captured, measured from some arbitrary reference time. Encoder row 3225 shows the encoder count at the time the frame was captured. Object detect row 3230 shows the logic input to the ObjectDetect Judge. From this it can be seen that the active frames are 59-64.

Location row 3240 shows the location of an edge measured by a Locator, oriented to have a search range substantially in the direction of motion and chosen by a user. The location is measured relative to the center of the Locator's search range, and is shown only for the active frames. It can be seen that the location crosses zero, the mark point, somewhere between frames 61 and 62, which is between times 44.2 and 46.2, and counts 569 and 617.

In this example, dynamic image analysis ends on frame 66, after two consecutive inactive frames are found. A mark time based on location, shown in sixth row 3250, is computed at the end of frame 66. The value shown, 45.0, is the linear interpolated time between frames 61 and 62 where the location crosses zero. As an alternative, a line can be fit to the points for the active frames from time row 3220 and location row 3240, and that line can be used to calculate the time value corresponding to location 0.

A mark time based on the time that the object was first detected is shown in the seventh row 3260.

A considerable amount of additional useful information can be obtained from the measured data, summarized in the following table:

|  | two points | least-squares fit |
|---|---|---|
| mark time (ms) | 45.00 | 45.01 |
| mark count | 588.2 | 587.6 |
| object speed (pixels/ms) | 0.725 | 0.725 |
| pixel size (counts/pixel) | 31.6 | 31.8 |

As can be seen, the information can be computed using two points (linear interpolation using zero-crossing frames 61 and 62 for the mark, and slope using frames 59 and 64 for speed and size), or by a least-squares fit, or by other methods known in the art. The results are similar for the two methods shown, with the least-squares method generally being more accurate but more complex.

Mark time and count may be used for output signal synchronization as explained above. Object speed may be communicated to automation equipment for a variety of purposes. The pixel size calculation gives a calibration of the size of a pixel in encoder counts, which are proportional to physical distance along the production line. Such a calibration can be used for a variety of well-known purposes, including presenting distances in the FOV in physical units for the user, and transporting a setup between vision detectors that may have slightly different optical magnifications by adjusting the size and position of Photos based on the calibrations.

Since pixel size can be calculated for every object, the value can be used to determine object distance. Smaller pixel sizes correspond to objects that are farther away. For constant speed production lines the same determination can be made using object speed, just as when looking out a car window distant objects appear to be moving slower than nearby ones.

The data in FIG. 32 may be obtained from a single Locator designated by a user for that purpose. In another embodiment, a user could designate two locators separated either parallel or normal to the direction of motion in the FOV. All such Locators would be oriented to have their search range parallel to the direction of motion. Differences in pixel size calibration obtained from two such Locators represents object rotation in space, about an axis normal to the direction of motion and in the plane of the object for Locators separated parallel to the direction of motion, and about an axis parallel to the direction of motion for Locators separated normal to the direction of motion.

Figure 33:
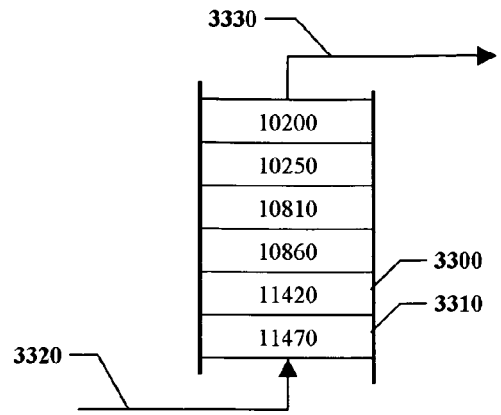
FIG. 33 shows an output buffer that is used to generate synchronized pulses for downstream control of actuators.

FIG. 33 shows an output FIFO that is used to generate synchronized pulses for downstream control of actuators. In general many objects may lie between the inspection point and a downstream actuator, and a FIFO or similar mechanism is needed to hold information about the output pulse, if any, corresponding to each such object until it reaches the actuator and the pulse is needed.

Referring to FIGS. 5 and 31, report step 560 for first object 500, corresponding to output pulse 3180, occurs after delay 570, corresponding to output delay 3120, which is after second object 510 has been analyzed. Whenever output delay 3120 is greater than the time between objects, a FIFO or similar mechanism is needed.

FIG. 33 shows a simple FIFO that can be used for this purpose. The FIFO holds numbers corresponding to the time at which an output signal should change state. At decision point 3110 (FIG. 31) an output pulse can be scheduled by placing times, for example leading edge time 3300 and trailing edge time 3310, into FIFO input 3320. A software timer or other mechanism runs at a scheduled time determined by removing a time from the FIFO output 3330. When the scheduled time arrives, the state of the output signal is changed and a new scheduled time is removed from the FIFO.

Judges, Outputs, and Examples of Use

Figure 34:
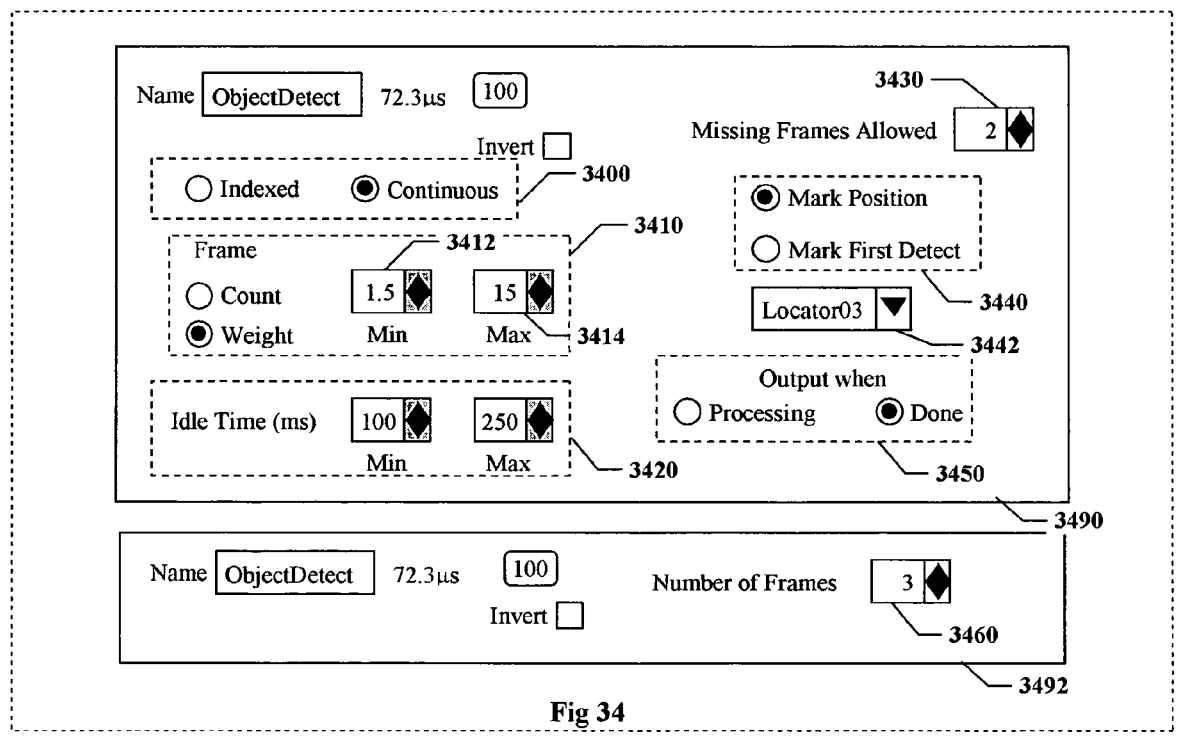
FIG. 34 shows a portion of the HMI for user configuration of object detection parameters.

FIG. 34 shows parameter views for user configuration of the ObjectDetect Judge. A first parameter view 3490 is used for visual event detection mode, and a second parameter view 3492 is used for external trigger mode.

Presentation control 3400 allows selection of either indexed or continuous object presentation.

Frame filtering controls 3410 allow the user to set limits on the count or total object detection weight of active frames. Minimum frame spinner 3412 allows a user to choose the minimum required count or weight threshold, as explained above in the description of FIG. 12 where it refers to FIG. 34. Maximum frame spinner 3414 allows a user to choose a maximum frame count or weight, after which dynamic image analysis will terminate and a decision will be made regardless of how many more active frames may be found. This allows the user to limit the amount of time the invention will spend on one object, and is particularly useful for indexed or slow-moving objects.

Idle time controls 3420 allow a user to specify minimum and maximum times for idle step 580 (FIG. 5). If the minimum and maximum are equal, the idle time is fixed by the user. If the maximum is greater than the minimum, the vision detector can automatically choose a time within the specified range based on the measured rate at which objects are being presented. A phase-locked loop, shown in FIGS. 47 and 48, can be used to measure the object presentation rate. In an illustrative embodiment, the automatically selected idle time is half the object presentation period, clamped if necessary to fall within the user-specified range.

Missing frame spinner 3430 allows a user to specify the maximum number of consecutive inactive frames that will be accepted without terminating dynamic image analysis. Such a frame is illustrated by analysis step 542 in FIG. 5.

Marking control 3440 allows a user to select the marking mode. If marking by location is selected, the user must specify a Locator using locator list control 3442.

Output mode control 3450 allows a user to select the mode that defines when a pulse appears on the logic output.

Frame count spinner 3460 allows a user to select the number of frames to analyze in external trigger mode.

Figure 35:
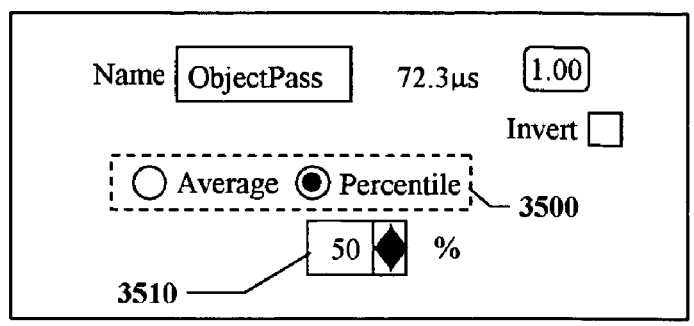
FIG. 35 shows a portion of the HMI for user configuration of object inspection parameters.

FIG. 35 shows a parameter view for user configuration of the ObjectPass Judge. Mode control 3500 allows a user to choose between the weighted average method described for FIG. 12, and the percentile method described for FIG. 13. If the percentile method is chosen, the threshold t therein described can be selected using percentile spinner 3510.

Figure 36:
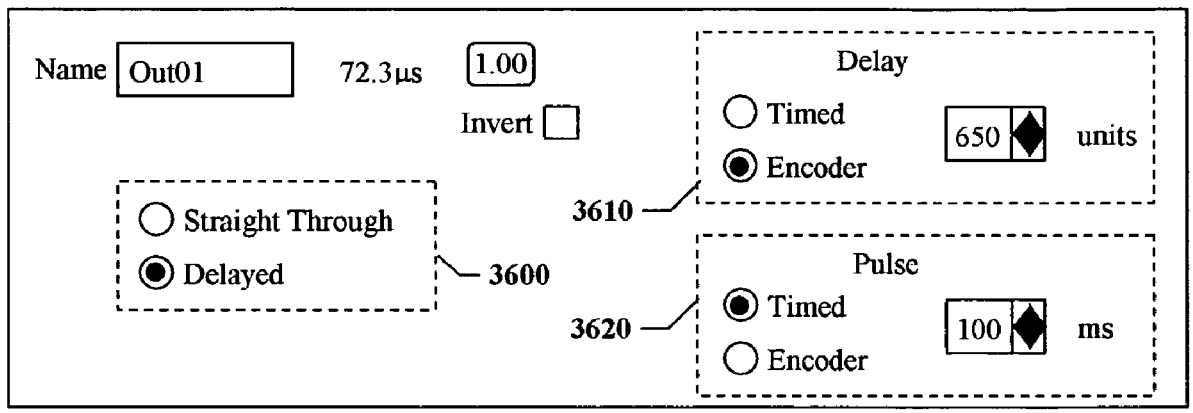
FIG. 36 shows a portion of the HMI for user configuration of output signals.

FIG. 36 shows a parameter view for user configuration of an Output Gadget. Mode control 3600 allows a user to choose how the output signal is controlled. In "straight through" mode, the logic input is passed directly to the output signal without any delay or synchronization. In "delayed" mode, on the rising edge of the logic input an output pulse is scheduled to occur at a time delayed from the most recently recorded mark time (or encoder count) by the amount specified by delay controls 3610, and of duration specified by pulse controls 3620. The scheduled pulse may be placed in a FIFO associated with the Output Gadget.

Figure 37:
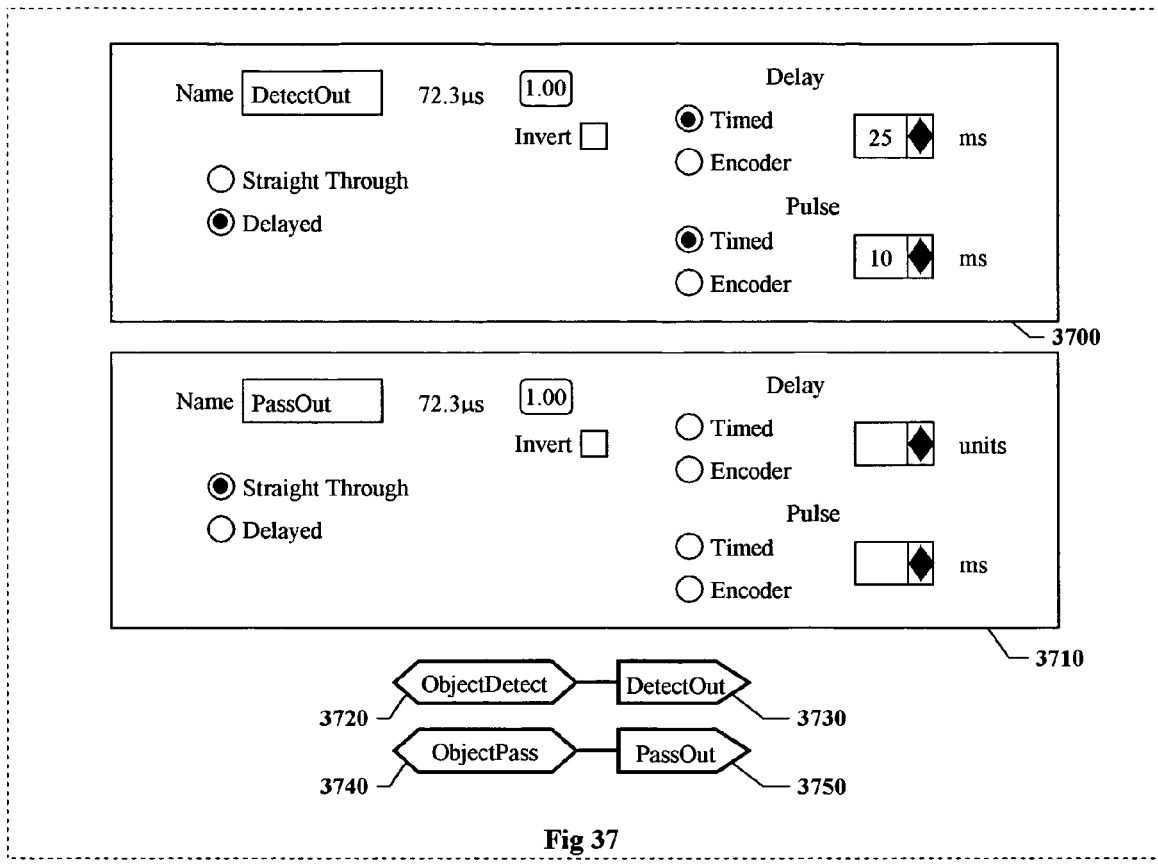
FIG. 37 illustrates one way to configure the invention to perform visual event detection when connected to a PLC.

FIG. 37 illustrates one way to configure the present invention to operate in visual event detection mode when connected to a PLC. A logic view shows ObjectDetect Judge 3720 wired to "DetectOut" Output Gadget 3730 and ObjectPass Judge 3740 wired to "PassOut" Output Gadget 3750. An appropriate set of Photos and Gates is wired to the Judges and not shown.

ObjectDetect Judge 3720 is configured for continuous presentation, mark by location, and output when done, as shown in FIG. 34.

A first parameter view 3700 shows that "DetectOut" Output Gadget 3730 is configured to generate a synchronized 10 ms. pulse 25 ms. after the mark time. This pulse will be triggered by the rising edge of ObjectDetect Judge 3720. A second parameter view 3710 shows that "PassOut" Output Gadget 3750 is configured to send the pass/fail result from ObjectPass Judge 3740 directly to its output signal.

A PLC could sense the two output signals, noting the time of the rising edge of the signal from "DetectOut" and latching the output of "PassOut" on that edge. The PLC would then know that an object has been detected, when it crossed the mark point (25 ms. before the rising edge of "DetectOut"), and the result of the inspection.

Figure 38:
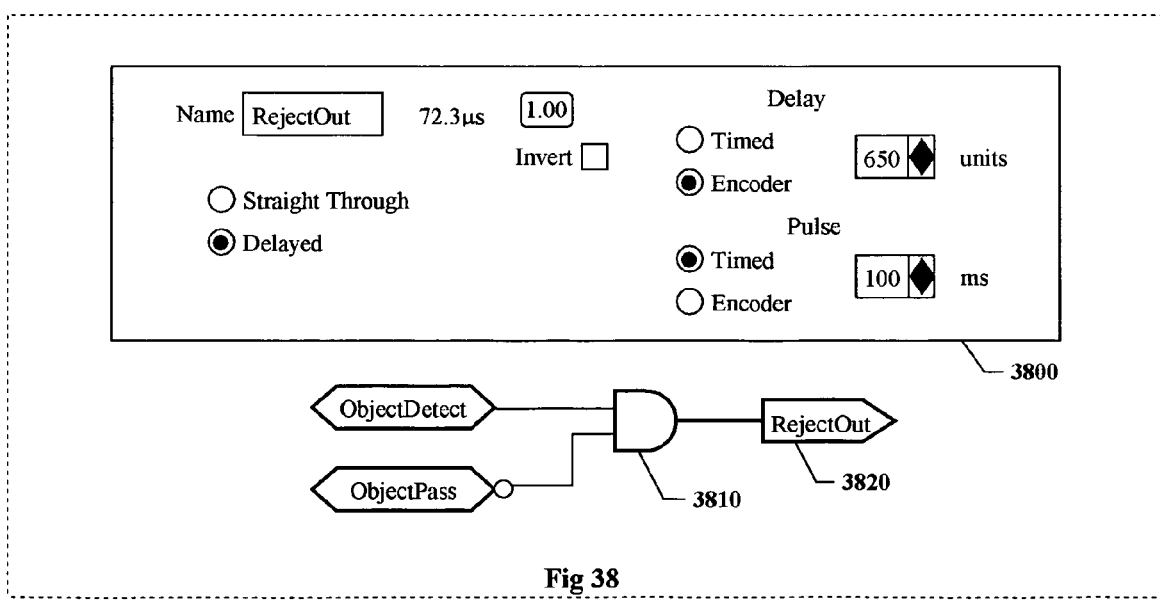
FIG. 38 illustrates one way to configure the invention to perform visual event detection for direct control of a reject actuator.

FIG. 38 illustrates one way to configure the invention to operate in visual event detection mode for direct control of a reject actuator. A logic view shows AND Gate 3810 wired to the ObejctDetect and ObjectPass Judges so as to generate a pulse when a failing object is detected. AND Gate 3810 is wired to "RejectOut" Output gadget 3820, thereby receiving this pulse. Parameter view 3800 shows that "RejectOut" Output Gadget 3820 is configured to generate a synchronized 100 ms. pulse 650 encoder counts after the mark time. This pulse will be triggered by the detection of a failed object. The ObjectDetect Judge is configured for continuous presentation, mark by location, and output when done.

Figure 39:
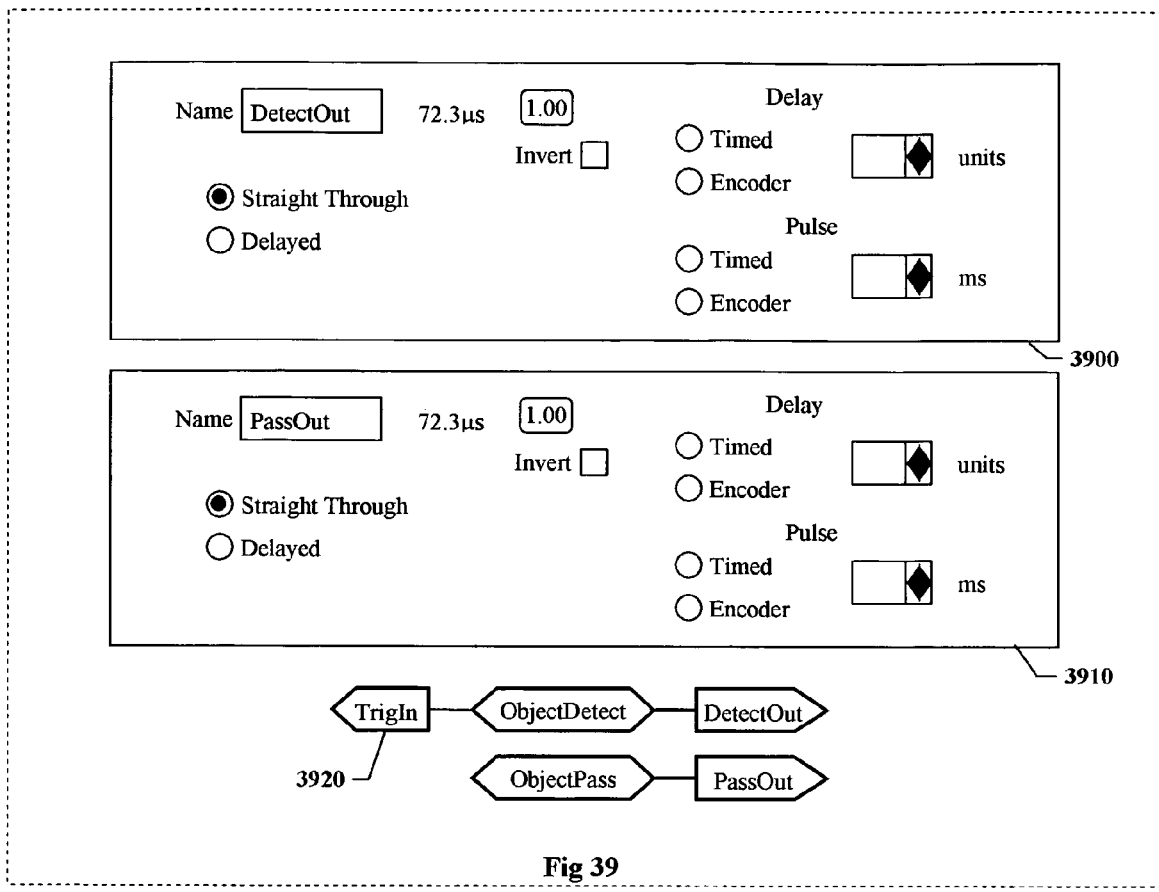
FIG. 39 illustrates one way to configure the invention to use a trigger signal when connected to a PLC.

FIG. 39 illustrates one way to configure the invention to operate in external trigger mode when connected to a PLC. A logic view shows the ObjectDetect Judge wired to "DetectOut" Output Gadget and the ObjectPass Judge wired to "PassOut" Output Gadget, as was shown in FIG. 37. However, instead of wiring a set of Photos and Gates to the logic input of the ObjectDetect Judge, "TrigIn" Input Gadget 3920 is used. It is the fact that the logic input of ObjectDetect depends on no Photos and at least one Input Gadget that tells the Judge to operate in external trigger mode. If nothing is wired to ObjectDetect, it will operate in continuous analysis mode.

First parameter view 3900 and second parameter view 3910 show that both Output Gadgets pass their logic inputs straight through to their output signals. A PLC could sense the two output signals and latch the output of "PassOut" on the rising edge of "DetectOut". The PLC would then be alerted that an object has been detected and the result of the inspection, and it would have to obtain the mark time, if needed, from the external trigger.

Another way to configure the invention to operate in external trigger mode when connected to a PLC would be to use the Output Gadget configuration of FIG. 37 to produce a synchronized output pulse. In this method the PLC could obtain the mark time from the vision detector and not waste a valuable input on a connection to the external trigger.

Figure 40:
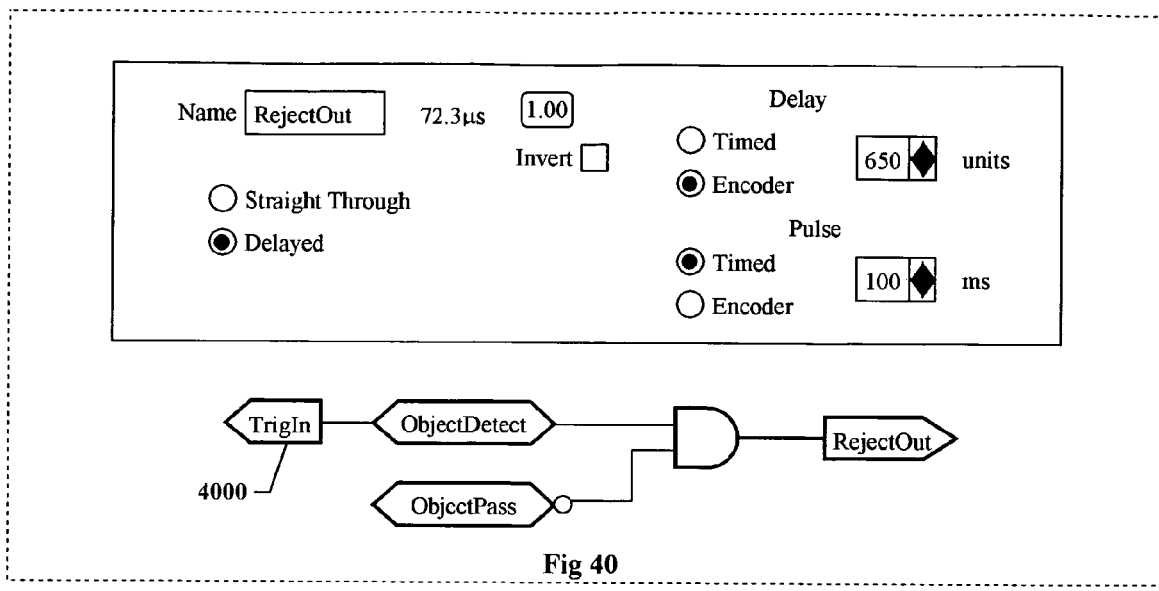
FIG. 40 illustrates one way to configure the invention to use a trigger signal for direct control of a reject actuator.

FIG. 40 illustrates one way to configure the invention to operate in external trigger mode for direct control of a reject actuator. Operation is identical to the configuration shown and described for FIG. 38, except that "TrigIn" Input Gadget 4000 is wired to ObjectDetect instead of a set of Photos and Gates. Note that the mark time is simply the time of the external trigger.

Continuous Analysis and Examples

Figure 41:
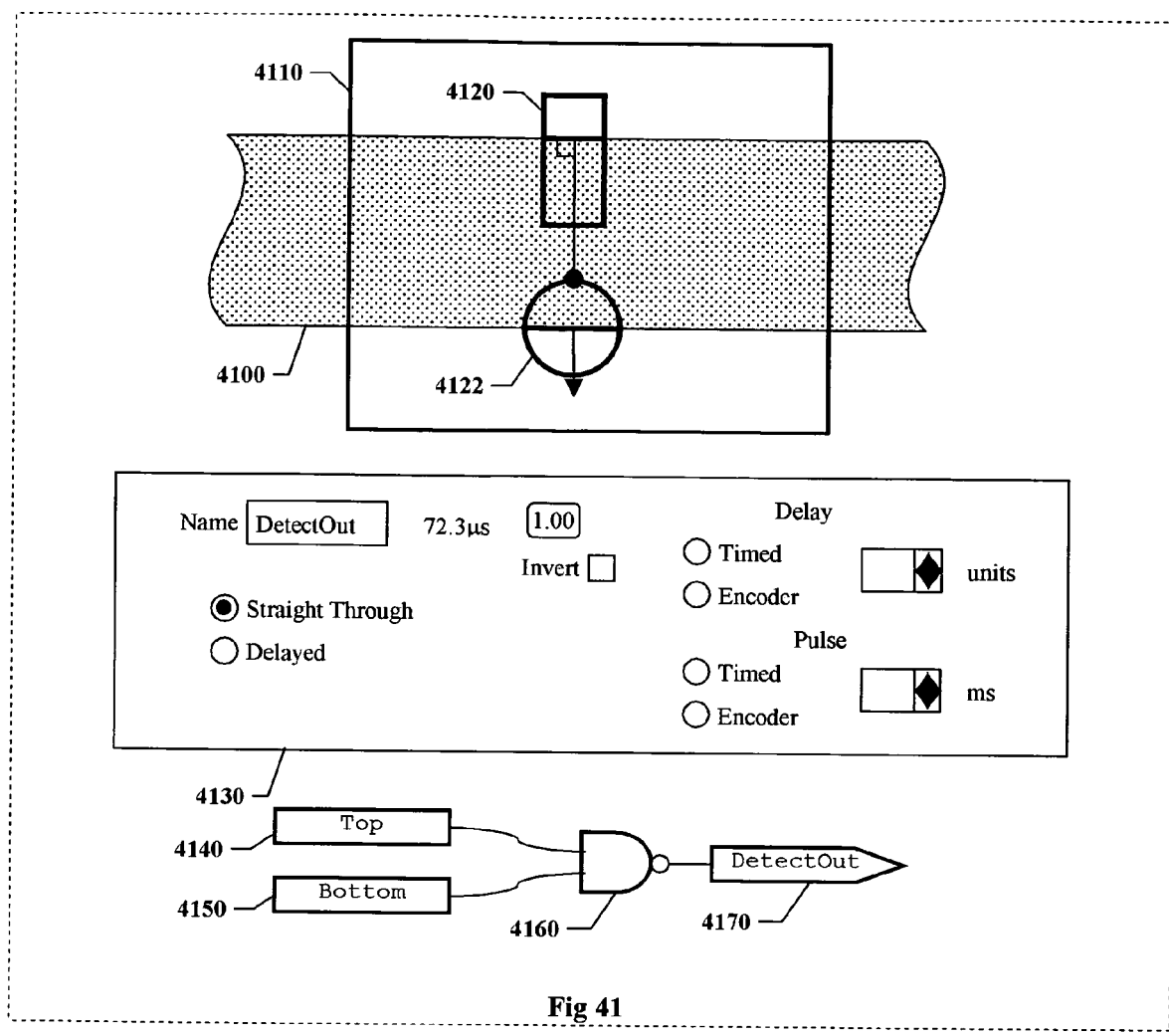
FIG. 41 illustrates one way to configure the invention to perform continuous analysis for detection of flaws on a continuous web.

FIG. 41 illustrates one way to configure the invention to operate in continuous analysis mode for detection of flaws on a continuous web. Image view 4110 shows a portion of continuous web 4100 that is moving past the vision detector.

Locator 4120 and Edge Detector 4122 are configured to inspect the web. If the web breaks, folds over, or becomes substantially frayed at either edge, then Locator 4120 and/or Edge Detector 4122 will produce a false output (logic value<0.5). If the web moves up or down Locator 4120 will track the top edge and keep Edge Detector 4122 in the right relative position to detect the bottom edge. However, if the width of the web changes substantially, Edge Detector 4142 will produce a false output.

In a logic view "Top" Locator 4140 represents Locator 4120, and "Bottom" Detector 4150 represents Edge Detector 4122. These are wired to AND Gate 4160, whose logic output is inverted and wired to "DetectOut" Output gadget 4170. As can be seen in parameter view 4130, the inverted output of AND Gate 4160 is passed directly to an output signal.

The output signal will therefore be asserted whenever either Photo's logic output is false. The signal will be updated at the high frame rate of the vision detector, providing a continuous indication of the status of the web.

Figure 42:
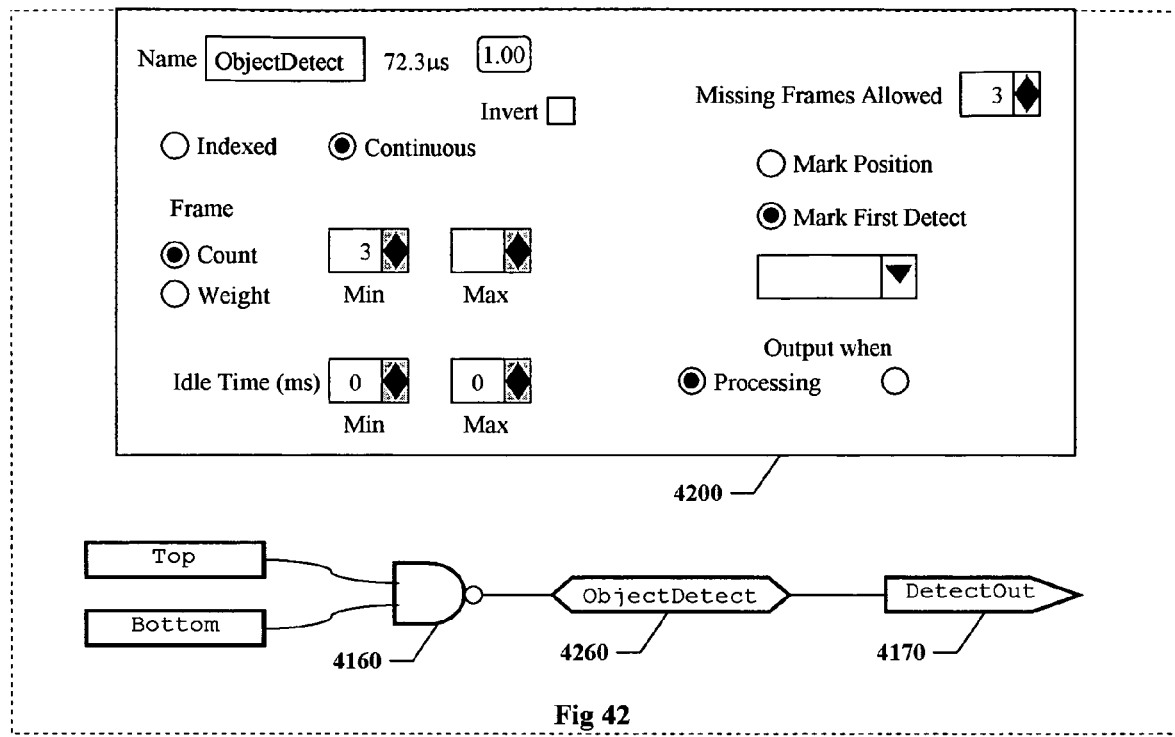
FIG. 42 illustrates one way to configure the invention for detection of flaws on a continuous web that provides for signal filtering.

FIG. 42 illustrates one way to configure the invention for detection of flaws on a continuous web that uses the ObjectDetect Judge for signal filtering. Configuration is similar to that of FIG. 41, with image view 4110 and parameter view 4130 applying to this Figure as well. A logic view shows the same configuration as FIG. 41, except that ObjectDetect Judge 4260 is placed between AND Gate 4160 and "DetectOut" Output Gadget 4170.

Parameter view 4200 shows how the ObjectDetect Judge is configured. In this application there are no discrete objects, but an "object" is defined to a stretch of defective web. The output mode is set to "output when processing", so one output pulse is produced for each stretch of defective web, whose duration is the duration of the defect.

By setting the minimum frame count to 3, insignificant stretches of defective web are filtered out and not detected. By allowing up to 3 missing frames, insignificant stretches of good web immersed in a longer defective portion are also filtered out. Thus the output signal will be similar to that of FIG. 41, but with insignificant glitches removed. Note that these values are intended to be exemplary, and would be chosen by a user to be suitable for a specific application.

There is no maximum frame count specified, so a stretch of defective web can continue indefinitely and be considered one defect. The idle time may be set to zero so that the web is always being inspected.

Figure 43:
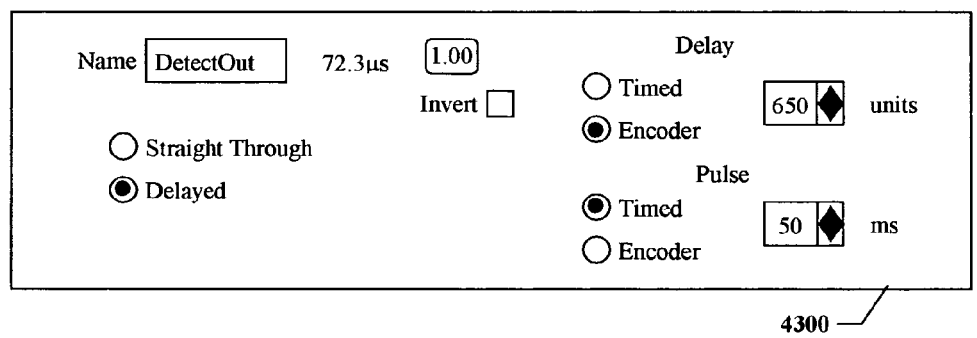
FIG. 43 illustrates one way to configure the invention for detection of flaws on a continuous web that provides for signal synchronization.

FIG. 43 illustrates one way to configure the invention for detection of flaws on a continuous web that uses the ObjectDetect Judge and an Output Gadget for signal synchronization. Configuration is identical to FIG. 42, except that "DetectOut" Output Gadget 4170 is configured as shown in parameter view 4300.

Note in parameter view 4200 that the ObjectDetect Judge is configured to set the mark time to the time that the "object", here a stretch of defective web, is first detected. As can be seen in parameter view 4300, a 50 ms. output pulse is generated 650 encoder counts after the mark time.

Detecting Objects Without Using Locators

Figure 44:
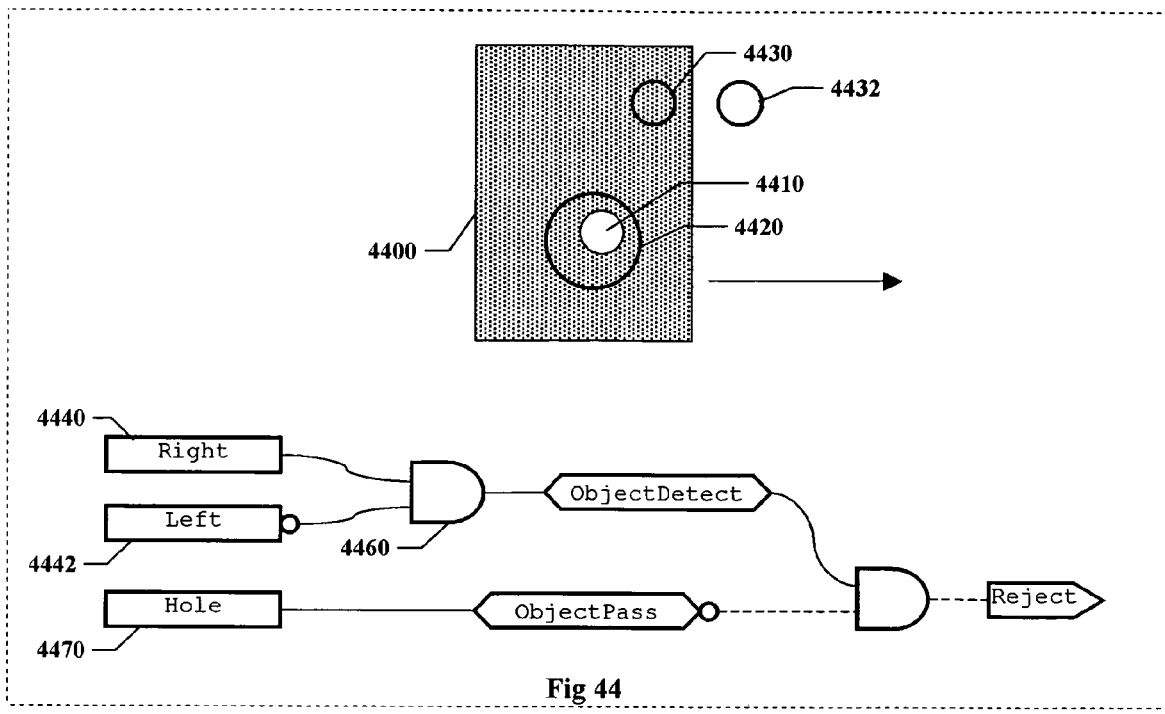
FIG. 44 illustrates one way to configure the invention to perform visual event detection without tracking the location of the object in the field of view.

FIG. 44 illustrates one way to configure the invention to operate in visual event detection mode without using Locators as input to the ObjectDetect Judge to determine active frames. An object 4400 containing a feature 4410 moves left to right in the FOV of a vision detector. Contrast Detector ROI 4420 is positioned to detect the presence of feature 4410. A left Brightness Detector ROI 4430 and a right Brightness Detector ROI 4432 are positioned to detect the object over a range in the FOV defined by their separation.

A logic view shows "Right" Brightness Detector 4440 corresponding to right Brightness Detector ROI 4432, and "Left" Brightness Detector 4442 corresponding to left Brightness Detector ROI 4430. "Right" Brightness Detector 4440 produces a true logic output when object 4400 is not covering right Brightness Detector ROI 4432, because the background in this example is brighter than object 4400. "Left" Brightness Detector 4442 produces a true logic output when object 4400 is covering left Brightness Detector ROI 4430, because its output is inverted. Therefore AND Gate 4460 produces a true logic output when the right edge of object 4400 is between left Brightness Detector ROI 4430 and right Brightness Detector ROI 4432.

Note that the logic output of AND Gate 4460 is actually a fuzzy logic level that will fall between 0 and 1 when the right edge of object 4400 partially covers either ROI. Contrast Detector ROI 4420 must be large enough to detect feature 4410 over the range of positions defined by the separation between left Brightness Detector ROI 4430 and right Brightness Detector ROI 4432, because since no locators are being used it will not be moved.

AND Gate 4460 is wired to the ObjectDetect Judge, and "Hole" Contrast Detector 4470, corresponding to Contrast Detector ROI 4420, is wired to the ObjectPass Judge. The Judges in this example are configured for visual event detection and direct control of a reject actuator, as in FIG. 38.

Note that in the example of FIG. 44, a Locator could readily have been used instead of the pair of Brightness Detectors, because the right edge of object 4400 is relatively straightforward to locate. There will be applications, however, where locators may be difficult to use due to lack of clean edges, and where using some combination of Detectors would be advantageous.

Learning

FIG. 45 illustrates rules that may be used by an illustrative embodiment of a vision detector for learning appropriate parameter settings based on examples shown by a user. This Figure will be used in conjunction with FIG. 22 to explain the exemplary learning method.

In an illustrative embodiment Photos can learn appropriate settings for the sensitivity fuzzy thresholds. The learning process may also provide suggestions as to what Detectors to use and, where appropriate, what settings are likely to work best. Learning is by example—users will present objects that they have judged to be good or bad, and will so indicate by interaction with HMI 830.

Learning is optional, as default or manual settings can be used, but is strongly recommended for the Brightness and Contrast Detectors because their analog outputs are in physical units (e.g. gray levels) that have no absolute meaning. Learning is less critical for the Edge, Spot, and Template Detectors, because their outputs are primarily based on a normalized correlation value that is dimensionless and with absolute meaning.

For example, if an Edge or Spot Detector has an analog output of 80, one can be fairly confident that an edge or spot has indeed been detected, because the correlation coefficient of the image ROI with an ideal edge or spot template is at least 0.8. If the output is 25, one can be fairly confident that no edge or spot has been detected. But with, for example, a Brightness Detector, is 80 bright enough? Is 25 dark enough? This is best learned by example in most instances.

There are two parts to the learning process. The first concerns how users interact with HMI 830 to teach a particular example. The second concerns what a Photo does when presented with such an example.

Referring to FIG. 22, parameter views for Photos contain thumbs-up button 2210 and thumbs-down button 2212. The buttons are next to logic output label 2204, which, as previously described, may change color or other characteristic to distinguish between true ($\geq 0.5$) and false ($<0.5$). For purposes of the following discussion, green will be used for true and red for false. Although not visible in FIG. 22, thumbs-up button 2210 is green and thumbs-down button 2212 is red. The proximity to logic output label 2204 and matching colors helps the user understand the function of the buttons.

Clicking green thumbs-up button 2210 means "learn that the logic output of this Photo should now be green (true)." This operation is called learn thumbs-up. Clicking red thumbs-down button 2212 means "learn that the logic output of this Photo should now be red (false)." This operation is called learn thumbs-down. These semantics are intended to be clear and unambiguous, particularly when the ability to invert the output comes into play. The terms "good" and "bad", often used in describing example objects used for learning, change meaning depending on whether the output is inverted and how it is used by Gates to which it is connected.

Suppose one is using three Detectors that all must have a true output for an object to pass inspection. One can teach each Detector individually, but this could be unnecessarily cumbersome. If a good object is presented, all three Detectors should be true and so a single click somewhere to say, "this is a good object" would be useful. On the other hand, if a bad object is presented, there is often no way to know which Detectors are supposed to be false, and so they are generally taught individually.

Likewise, if the three Detectors are OR'd instead, meaning that an object passes if any of them have a true output, then one might teach a bad object with a single click, but for a good object the Detectors are generally trained individually. Once again, however, these rules change as inputs and outputs are inverted.

Teaching multiple detectors with one click can be managed without confusion by adding thumbs-up and thumbs-down buttons to Gates, following rules shown in FIG. 45. The buttons are displayed and clicked in a parameter view for each Gate, but FIG. 45 shows them in a logic view for descriptive purposes. Once again, clicking a green (red) thumbs-up (-down) button tells the Gate to learn thumbs-up (-down), which means "learn that the logic output of this Gate should now be green (red)."

An AND Gate with a non-inverted output learns thumbs-up by telling Gadgets wired to its non-inverted inputs to learn thumbs-up, and Gadgets wired to its inverted inputs to learn thumbs-down. For example, non-inverted AND Gate 4500 learns thumbs-up by telling Photo 4502 to learn thumbs-up, AND Gate 4504 to learn thumbs-up, and Photo 4506 to learn thumbs-down. An AND Gate with a non-inverted output cannot learn thumbs-down, so that button can be disabled and it ignores requests to do so.

An AND Gate with an inverted output learns thumbs-down by telling Gadgets wired to its non-inverted inputs to learn thumbs-up, and Gadgets wired to its inverted inputs to learn thumbs-down. For example, inverted AND Gate 4510 learns thumbs-down by telling Photo 4512 to learn thumbs-up, Photo 4514 to learn thumbs-up, and OR Gate 4516 to learn thumbs-down. An AND Gate with an inverted output cannot learn thumbs-up, so that button can be disabled and it ignores requests to do so.

An OR Gate with a non-inverted output learns thumbs-down by telling Gadgets wired to its non-inverted inputs to learn thumbs-down, and Gadgets wired to its inverted inputs to learn thumbs-up. For example, non-inverted OR Gate 4520 learns thumbs-down by telling OR Gate 4522 to learn thumbs-down, Photo 4524 to learn thumbs-down, and Photo 4526 to learn thumbs-up. An OR Gate with a non-inverted output cannot learn thumbs-up, so that button can be disabled and it ignores requests to do so.

An OR Gate with an inverted output learns thumbs-up by telling Gadgets wired to its non-inverted inputs to learn thumbs-down, and Gadgets wired to its inverted inputs to learn thumbs-up. For example, inverted OR Gate 4530 learns thumbs-up by telling Photo 4532 to learn thumbs-down, Photo 4534 to learn thumbs-down, and AND Gate 4536 to learn thumbs-up. An OR Gate with an inverted output cannot learn thumbs-down, so that button can be disabled and it ignores requests to do so.

Photos that are told to learn thumbs-up or thumbs-down by a Gate act as if the equivalent button was clicked. Gates pass the learn command back to their inputs as just described. All other Gadgets ignore learning commands in this example.

One exception to the above rules is that any Gate that has exactly one input wired to Photos, either directly or indirectly through other Gates, can learn thumbs-up and thumbs-down, so both buttons are enabled. Learn commands for such Gates are passed back to said input, inverted if the Gate's output or said input is inverted, but not both.

Users need not remember or understand these rules. In essence, the only rule to remember is to click the color one wants the output to be. Whenever the mouse is over a thumbs button, a tool tip could be provided to tell exactly which Photos will be trained, or explains why the button is disabled. When a thumbs button is clicked, a clear but non-intrusive feedback can be provided to confirm that training has indeed occurred.

Figure 46:
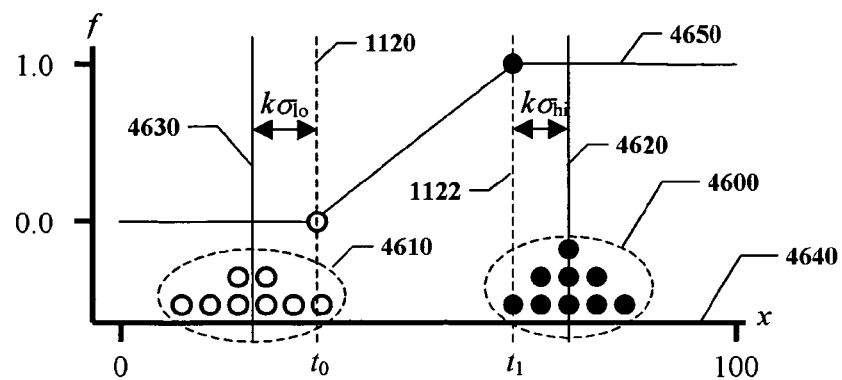
FIG. 46 further illustrates rules that are used by an illustrative embodiment of a vision detector for learning appropriate parameter settings based on examples shown by a user.

FIG. 46 illustrates how a Photo learns thumbs-up or thumbs-down. In an illustrative embodiment each Photo keeps two sets of statistics, called the output high statistics and the output low statistics. Each such set includes a count, a sum of analog outputs, and a sum of squared analog outputs, so that mean output low $m_{lo}$, mean output high $m_{hi}$, standard deviation of output low $\sigma_{lo}$, and standard deviation of output high $\sigma_{hi}$ can be computed. For each learn command, a Photo will add the analog output to a set of statistics as follows:

|  | logic output not inverted | logic output inverted |
| --- | --- | --- |
| thumbs-down | output low | output high |
| thumbs-up | output high | output low |

In the example of FIG. 46, x-axis 4640 corresponds to the analog output of a Photo. A distribution of output high values 4600, and a distribution of output low values 4610 have been learned from appropriate example objects. Mean output low 4630, mean output high 4620, standard deviation of output low (not shown), and standard deviation of output high (not shown) have been computed.

The statistics are used to compute the Photo's sensitivity fuzzy threshold 4650, defined by low threshold $t_0$ 1120 and high threshold $t_1$ 1122 (see also FIG. 11).

$$t_0 = m_{lo} + k\sigma_{lo}$$

$$t_1 = m_{hi} - k\sigma_{hi} \tag{21}$$

The parameter k may be chosen as appropriate. In an illustrative embodiment, k=0.

The method for learning thumbs-up or thumbs-down is summarized by the following steps:

1. Compute analog output and add to the output low or output high statistics as appropriate for thumbs-up or thumbs-down, and logic output inverted or not inverted;
2. Compute means and standard deviations for the output high and output low statistics; and
3. Update the sensitivity fuzzy threshold based on the means and standard deviations using equations 21.

Photos can also retain the most recent manual threshold settings, if any, so that they can be restored if desired by the user. All statistics and settings can be saved for all Photos on HMI 830, so that learning can continue over multiple sessions. Users can clear and examine the statistics using appropriate HMI commands.

If a set of statistics contains no examples, default values for the mean can be used. In an illustrative embodiment, the defaults are $$m_{lo}=a_{lo}+0.1(a_{hi}-a_{lo})$$

$$m_{hi}=a_{lo}+0.9(a_{hi}-a_{lo}) \quad (22)$$

where $a_{lo}$ is the lowest possible analog output and $a_{hi}$ is the highest. If a set of statistics contains fewer than two examples, the standard deviation can be assumed to be 0. This means that learning form a single example can be allowed, although it is generally not encouraged.

In another illustrative embodiment, a learn command for a Detector computes the analog outputs that would result from each type of Detector operating on the ROI of the Detector being taught. Statistics for each Detector type are computed and stored, and used to suggest better Detector choices by looking for larger separations between the output low and output high examples.

Using a Phase-Locked Loop for Missing and Extra Object Detection

Figure 47:
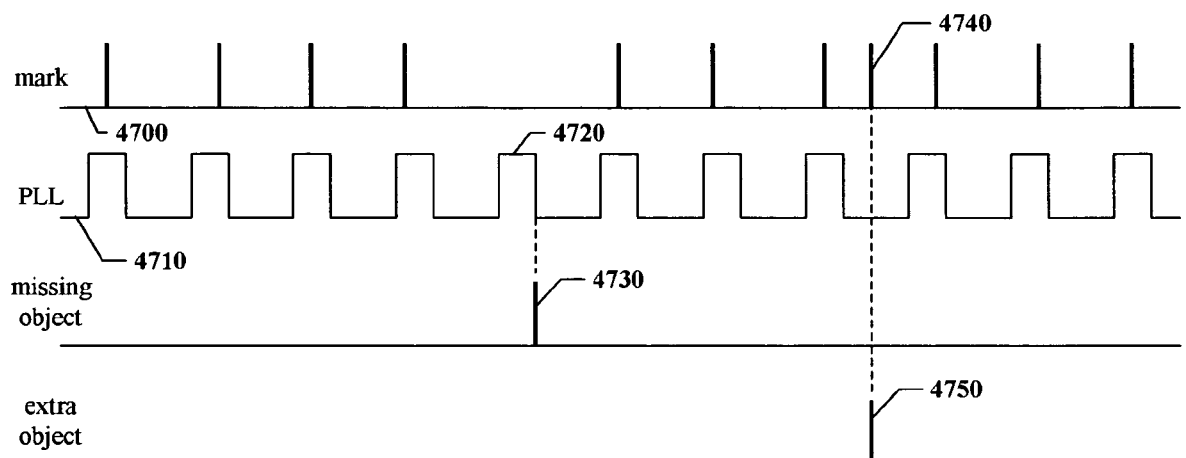
FIG. 47 illustrates the use of a phase-locked loop (PLL) to measure the object presentation rate, and to detect missing and extra objects, for production lines that present objects at an approximately constant rate.

FIG. 47 illustrates the use of a phase-locked loop (PLL) to measure the object presentation rate, and to detect missing and extra objects, for production lines that present objects at an approximately constant rate. The implementation of a PLL to synchronize to a train of pulses, and to detect missing and extra pulses, should be clear to those of ordinary skill.

In one embodiment, a signal containing output pulses synchronized to the mark time, for example output signal 3160 containing output pulse 3180 (FIG. 31), is connected to the input of a conventional PLL. Conventional PLL methods for missing and extra pulse detection are used to detect missing and extra objects. The frequency of the voltage-controlled oscillator used by a conventional PLL gives the object presentation rate.

In an illustrative embodiment, a software PLL internal to vision detector DSP 900 (FIG. 9) is used. Referring to FIG. 47, a sequence of mark times 4700 is used by a software PLL to compute a corresponding sequence of time windows 4710 during which a mark is expected to occur. Time window 4720 contains no mark time, so a missing object is detected at time 4730, corresponding to the end of time window 4720. A mark time 4740 is detected outside of any time window, so an extra object is detecting at time 4750 corresponding to mark time 4740. Information about object presentation rate, and missing and extra objects can be reported to automation equipment.

Figure 48:
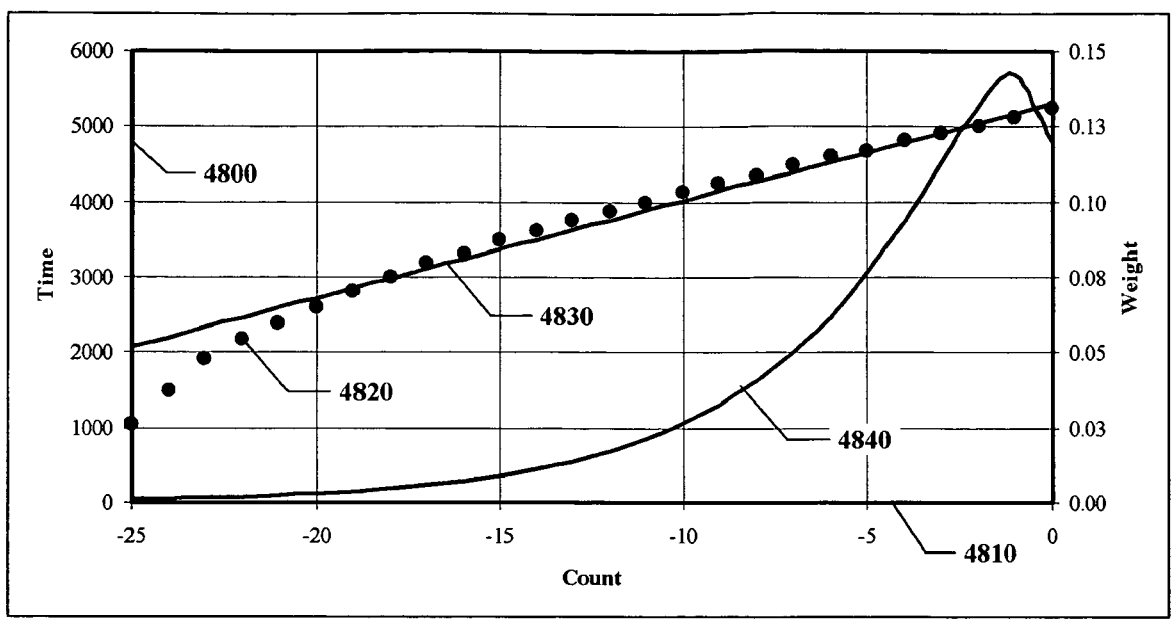
FIG. 48 illustrates the operation of a novel software PLL used in an illustrative embodiment.

FIG. 48 illustrates the operation of a novel software PLL used in an illustrative embodiment. Shown is a plot of mark time on vertical axis 4800 vs. object count on horizontal axis 4810. Each point plotted, including example point 4820, corresponds to one object detected. To insure numerical accuracy in the calculations, object count 0 can be used for the most recent object, and negative counts are used for previous objects. The next expected object corresponds to count 1.

A best-fit line 4830 is computed using a weighted least-squares method further described below. The weights are chosen to weight more recent points more strongly than more distant points. The slope of best-fit line 4830 gives the object presentation period, and the time corresponding to count=1 gives the expected time of the next object.

In one embodiment, a fixed number of the most recent points are given equal weight, and older points are given zero weight, so that only recent points are used. The set of recent points being used is stored in a FIFO buffer, and well-known methods are used to update the least-squares statistics as new points are added and old points are removed.

In an illustrative embodiment, weights 4840 corresponding to the impulse response of a discrete Butterworth filter are used. A discrete Butterworth filter is two-pole, critically-damped, infinite impulse response digital low-pass filter that is easily implemented in software. It has excellent low-pass and step response characteristics, considers the entire history of mark times, has one adjustable parameter to control frequency response, and does not need a FIFO buffer.

The output $y_i$ at count i of a Butterworth filter with inputs $x_i$ is $$v_i = v_{i-1} + f(x_i - y_{i-1}) - f'v_{i-1}$$

$$y_i = y_{i-1} + v_i \quad (23)$$

where f is the filter parameter, $$f' = 2\sqrt{f} \quad (24)$$

and $v_i$ are intermediate terms called velocity terms.

If the input is a unit impulse $x_0=1$, $x_i=0$ for $i \neq 0$, the output is the impulse response, which will be referred to by the symbol $w_i$. The effect of the filter is to convolve the input with the impulse response, which produces a weighted average of all previous inputs, where the weights are $w_{-i}$. Weights 4840 are the values $w_{-i}$ for f=0.12.

For the Butterworth PLL, three Butterworth filters are used, corresponding to the statistics needed to compute a least-squares best-fit line. Let the mark times be $t_i$, where i=0 corresponds to the most recent object, i<0 to previous objects, and i=1 to the next object. Furthermore, let all times be relative to $t_0$, i.e. $t_0=0$. The following weighted sums are needed:

$$y_t = \sum_i w_{-i} t_i \quad (25)$$

$$y_{xt} = \sum_i w_{-i} i t_i$$

$$y_{t2} = \sum_i w_{-i} t_i^2$$

Note that the summations are over the range $-\infty \leq i \leq 0$. These values are obtained as the outputs of the three Butterworth filters, which are given inputs $t_i$, $it_i$, and $t_i^2$.

The following additional values are needed, and are derived from the filter parameter f:

$$y_x = \sum_i w_{-i} i = 1 - \frac{f'}{f} \tag{26}$$

$$y_{x2} = \sum_i w_{-i} i^2 = y_x + \frac{6}{f}$$

$$C = \begin{pmatrix} y_{x2} & y_x \\ y_x & 1 \end{pmatrix}^{-1} = \frac{f}{f'+2} \begin{pmatrix} 1 & -y_x \\ -y_x & y_{x2} \end{pmatrix}$$

If best fit line 4830 is given by $t_i = ai + b$, then $$\begin{pmatrix} a \\ b \end{pmatrix} = C \begin{pmatrix} y_{xt} \\ y_t \end{pmatrix} \tag{27}$$

The value a is a very accurate measure of the current object presentation period. The equation of the line can be used to calculate the expected mark time at any point in the near future. The weighted RMS error of the best-fit line, as a fraction of object presentation period, is $$E = \frac{\sqrt{y_{t2} - (ay_{xt} + by_t)}}{a} \tag{28}$$

which is a measure of the variability in the object presentation rate.

A new mark time to be input to the three filters occurs at time $t_1$, which is simply the elapsed time between the new object and the most recent at $t_0 = 0$. For each of the three Butterworth filters, adjustments must be made to the output and velocity terms to reset $i=0$ and $t_0=0$ for the new object. This is necessary for equations 26 to be correct, and also for numerical accuracy. Without this correction, C would change with every input. Here are equations for the three filters, showing the corrections. Primes are used to indicate new values of the outputs and velocity terms, and the u terms are temporary values.

$$v'_t = v_t + f(t_1 - y_t) - f'v_t$$

$$u_t = y_t + v'_t$$

$$y'_t = u_t - t_1$$

$$u_{xt} = v_{xt} + f(t_1 - y_{xt}) - f'v_{xt}$$

$$v'_{xt} = u_{xt} - t_1 - v'_t$$

$$y'_{xt} = y_{xt} + v'_{xt} - u_t - y_x t_1$$

$$u_{t2} = v_{t2} + f(t_1^2 - y_{t2}) - f'v_{t2}$$

$$v'_{t2} = u_{t2} - 2t_1 v'_t$$

$$y'_{t2} = y_{t2} + u_{t2} - 2t_1 u_t + t_1^2 \tag{29}$$

A Butterworth PLL's output and velocity terms can be initialized to correspond to a set of values (a, b, E) as follows:

$$y_t = ay_x + b \tag{30}$$

$$y_{xt} = ay_{x2} + by_x$$

$$y_{t2} = ay_{xt} + by_t + E^2$$

$$v_t = \frac{y_t}{y_x}$$

$$v_{xt} = f \frac{(a+b-y_{xt}) - (a+b+v_t)}{f'}$$

$$v_{t2} = \frac{f[(a+b)^2 - y_{t2}] - 2(a+b)v_t}{f'}$$

This allows one to reset the PLL to start at a particular period p using equations 30 with a=p, b=0, and E=0. It also allows one to change the filter constant while the PLL is running by initializing the output and velocity terms using the current values of a, b, and E, and the new value of f.

In an illustrative embodiment, the Butterworth PLL determines whether or not it is locked onto the input mark times by considering the number of objects that have been seen since the PLL was reset, and the current value of E. The PLL is considered unlocked on reset and for the next n objects. Once at least n objects have been seen, the PLL locks when E goes below a lock threshold $E_l$, and unlocks when E goes above an unlock threshold $E_u$. In a further improvement, an unlocked filter parameter $f_u$ is used when the PLL is unlocked, and a locked filter parameter $f_l$ is used when the filter is locked. Switching filter parameters is done using equations 30 to initialize the output and velocity terms using the current values of a, b, and E.

In an illustrative embodiment, n=8, $E_l$=0.1, $E_u$=0.2, $f_l$=0.05, and $f_u$=0.25.

If m consecutive objects are missed, the next object will arrive at approximately $$t_{m+1} = a(m+1) + b \tag{31}$$

From this equation and the mark time $t_n$ of a new object, one may determine m:

$$m = \text{round}\left(\frac{t_n - b}{a} - 1\right) \tag{32}$$

To keep the equations for the Butterworth PLL correct, one must insert mark times for all of the missing objects. This may be accomplished by using $$t_1 = \frac{t_n}{m+1} \tag{33}$$

m+1 times as input to equations 29.

It will be understood that any discrete low-pass filter can be used in place of a Butterworth filter to implement a PLL according to the best-fit line method of the present invention. Based on the method described above, equations 23 through 33 would be replaced as appropriate for the filter chosen.

The foregoing has been a detailed description of various embodiments of the invention. It is expressly contemplated that a wide range of modifications and additions can be made hereto without departing from the spirit and scope of this invention. For example, the processors and computing devices herein are exemplary and a variety of processors and computers, both standalone and distributed can be employed to perform computations herein. Likewise, the imager and other vision components described herein are exemplary and improved or differing components can be employed within the teachings of this invention. Accordingly, this description is meant to be taken only by way of example, and not to otherwise limit the scope of this invention.

I claim:

1. A method for detecting an object, and determining a a mark count of the object, comprising:
    using a conveyor having motion relative to a two-dimensional field of view to transport the object;
    inputting an encoding signal responsive to the motion of the conveyor, from which can be obtained at desired times a corresponding encoder count indicating a relative location of the conveyor;
    capturing a plurality of frames, each frame of the plurality of frames comprising an image of the two-dimensional field of view;
    choosing, responsive to a first analysis of the plurality of frames, a plurality of active frames from the plurality of frames, such that the first analysis indicates sufficient evidence that the object is located in the field of view for each frame of the plurality of active frames;
    obtaining a plurality of capture counts corresponding to the plurality of active frames, each capture count of the plurality of capture counts being responsive to the encoder count corresponding to a time at which the corresponding active frame was captured;
    computing, responsive to a second analysis of the plurality of active frames, a plurality of location values, each location value of the plurality of location values responsive to a position of the object in the field of view in an associated active frame as computed by the second analysis;
    determining the mark count of the object using the plurality of location values and the plurality of capture counts, the mark count indicates the encoder count corresponding to a time when the object was located at a fixed mark point; and
    indicating a location of the object by producing a signal at a report time that occurs when the corresponding encoder count differs from the mark count by a delay count.

2. The method of claim 1 wherein determining the mark count comprises interpolating a pair of capture counts and a corresponding pair of location values.

3. The method of claim 1 wherein determining the mark count comprises extrapolating from the capture counts and the location values.

4. The method of claim 1 wherein determining the mark count comprises fitting a line to at least three capture counts and corresponding location values.

5. The method of claim 1, further comprising using a first-in first-out buffer to hold information needed for producing the signal at the report time.

6. The method of claim 1, wherein the location of the object, at the report time, is a downstream position that is separated from a mark point by a distance determined by the delay count.

7. The method of claim 6, further comprising adjusting the delay count so that the downstream position corresponds to a desired location of the object.

8. The method of claim 7, wherein the desired location corresponds to an actuator location.

9. The method of claim 8, further comprising judging, responsive to a third analysis of the plurality of active frames, whether the object satisfies an inspection criterion; and
    wherein producing the signal further comprises producing the signal only if the third analysis judges that the object does not satisfy the inspection criterion; and
    the actuator is a reject actuator; and further comprising using the signal to control the reject actuator.

10. The method of claim 7, wherein adjusting the delay count is responsive to a human-machine interface.

11. The method of any of claims 1 and 2-10 further comprising using the signal to indicate that the object was detected.

12. The method of any of claims 1 or 2-10, wherein the plurality of location values are computed responsive to at least one locator, the locator having a search range and oriented so that the search range is substantially parallel to a direction of motion of the object.

13. A system for detecting an object, and determining a mark count of the object, comprising:
    a conveyer, having motion relative to a two-dimensional field of view, that transports the object;
    an input device that receives an encoding signal responsive to the motion of the conveyer, from which can be obtained at desired times a corresponding encoder count indicating a relative location of the conveyer;
    an image capture device that captures a plurality of frames, each frame of the plurality of frames comprising an image of the two-dimensional field of view; and
    an analyzer that
        chooses, responsive to a first analysis of the plurality of frames, a plurality of active frames from the plurality of frames, such that the first analysis indicates sufficient evidence that the object is located in the field of view for each frame of the plurality of active frames;
        obtains a plurality of capture counts corresponding to the plurality of active frames, each capture count of the plurality of capture counts being responsive to the encoder count corresponding to a time at which the corresponding active frame was captured;
        computes, responsive to a second analysis of the plurality of active frames, a plurality of location values, each location value of the plurality of location values responsive to a position of the object in the field of view in an associated active frame as computed by the second analysis;
        determines the mark count of the object using the plurality of location values and the plurality of capture counts, wherein the a mark count indicates the encoder count corresponding to a time when the object was located at a fixed mark point; and
    an output signaler that indicates a location of the object by producing a signal at a report time that occurs when the corresponding encoder count differs from the mark count by a delay count.

14. The system of claim 13 wherein the analyzer determines the mark count by interpolating a pair of capture counts and a corresponding pair of location values.

15. The system of claim 13 wherein the analyzer determines the mark count by extrapolating from the capture counts and the location values.

16. The system of claim 13 wherein the analyzer determines the mark count by fitting a line to at least three capture counts and corresponding location values.

17. The system of claim 13, further comprising a first-in first-out buffer that holds information needed by the output signaler for producing the signal at the report time.

18. The system of claim 13, wherein the location of the object, at the report time, is a downstream position that is separated from the mark point by a distance determined by the delay count.

19. The system of claim 18, further comprising a controller that adjusts the delay count so that the downstream position corresponds to a desired location of the object.

20. The system of claim 19, further comprising an actuator having a location from which to act on the object; and
wherein the desired location corresponds to the location of the actuator.

21. The system of claim 20, wherein the analyzer judges, responsive to a third analysis of the plurality of active frames, whether the object satisfies an inspection criterion;
the output signaler produces the signal only if the analyzer judges that the object does not satisfy the inspection criterion;
the actuator is a reject actuator; and
the signal is used to control the reject actuator.

22. The system of claim 19, wherein the controller comprises a human-machine interface.

23. The system of any of claims 13, 14-22, wherein the analyzer computes the plurality of location values responsive to at least one locator, the locator having a search range and oriented so that the search range is substantially parallel to a direction of motion of the object.

24. A system for computing a mark count of an object transported by a transport medium, the transport medium in relative motion to a two-dimensional field of view, the object comprising a set of visible features, the set of visible features containing at least one visible feature; the system comprising:
a data processing device programmed to:
receive an encoder signal responsive to the relative motion of the transport medium, from which is obtained an encoder count indicating a relative location of the transport medium;
receive a plurality of active frames, each frame of the plurality of active frames comprising an image of the two-dimensional field of view;
obtain a plurality of capture counts corresponding to the plurality of active frames, each capture count of the plurality of capture counts being responsive to the encoder count corresponding to a time at which the corresponding active frame was captured;
compute a plurality of location values based on the plurality of active frames, each location value of the plurality of location values responsive to a position of a visible feature of the set of visible features of the object in an associated active frame; and
compute the mark count of the object using at least a portion of the plurality of location values and at least a portion of the plurality of capture counts, wherein the mark count indicates the encoder count corresponding to a time when the object was located at a fixed mark point; and
providing a value responsive to the mark count for consumption by an i/o module, wherein the i/o module uses the value responsive to the mark count to selectively signal a location of the object at a report time that occurs when the encoder count differs from the mark count by a delay count.

25. The system of claim 24, wherein the data processing device is further programmed to send the value to a first-in first-out buffer.

26. The system of claim 24, wherein the location of the object, at the report time, is a downstream position that is separated from the mark point by a distance determined by the delay count.

27. The system of claim 26, further comprising a controller that adjusts the delay count so that the downstream position corresponds to a desired location of the object.

28. The system of claim 27, wherein the downstream position corresponds to a location of an actuator.

29. The system of claim 24, wherein the data processing device is further programmed to:
judge, responsive to an analysis of the plurality of active frames, whether the object satisfies an inspection criterion; and
signal a reject actuator only when the object does not satisfy the inspection criterion.

30. The system of claim 27, wherein the controller comprises a human-machine interface.

31. The system of claim 24, wherein computing the mark count further comprises fitting a line to at least a portion of the plurality of location values and at least a portion of the plurality of capture counts.

32. The system of claim 24, wherein computing the mark count further comprises interpolating a pair of capture counts and a corresponding pair of location values.

33. The system of claim 24, wherein computing the mark count further comprises extrapolating from the capture counts and the location values.

34. The system of claim 24, wherein the data processing device is further programmed to receive a succession of frames, each frame of the succession of frames comprising an image of the two-dimensional field of view, such that the plurality of active frames comprises a subset of the succession of frames; and the data processing device is further programmed to:
compute a plurality of object detection weights based on and corresponding respectively to the succession of frames, each object detection weight of the plurality of object detection weights comprising evidence that the object is located in the two-dimensional field of view for the corresponding frame; wherein the succession of frames comprise images recorded at least before and after the object is located in the two-dimensional field of view; and
select as the plurality of active frames a portion of the succession of frames where the evidence is sufficient.

35. The system of claim 24, wherein the received frames are obtained by an imager with a global shutter.

36. The system of claim 35, wherein the data processing device is further programmed to compute the plurality of location values responsive to at least one locator, the locator having a search range and oriented so that the search range is substantially parallel to a direction of motion of the object.

37. A computer program product to compute a mark count of an object transported by a transport medium, the transport medium in relative motion with a two-dimensional field of view, the object comprising a set of visible features, the set of visible features containing at least one visible feature, the product tangibly embodied in a non-transitory computer readable medium, the computer program product comprising instructions being operable to cause a data processing apparatus to:
receive, an encoder signal responsive to the relative motion of the transport medium from which is obtained an encoder count indicating a relative location of the transport medium;

receive a plurality of active frames, each frame of the plurality of active frames comprising an image of the two-dimensional field of view;

obtain a plurality of capture counts corresponding to the plurality of active frames, each capture count of the plurality of capture counts being responsive to the encoder count corresponding to a time at which the corresponding active frame was captured;

compute a plurality of location values based on the plurality of active frames, each location value of the plurality of location values responsive to a position of a visible feature of the set of visible features of the object in an associated active frame; and compute the mark count of the object using at least a portion of the plurality of location values and at least a portion of the plurality of capture counts, wherein the mark count indicates the encoder count corresponding to a time when the object was located at a fixed mark point; and providing a value responsive to the mark count for consumption by an i/o module, wherein the i/o module uses the mark count to selectively signal a location of the object at a report time that occurs when the encoder count differs from the mark count by a delay count.

38. The medium of claim 37, further comprising instructions to send the value to a first-in first-out buffer.

39. The medium of claim 36, wherein the location of the object, at the report time, is a downstream position that is separated from the mark point by a distance determined by the delay count.

40. The medium of claim 39, further comprising a controller that adjusts the delay count so that the downstream position corresponds to a desired location of the object.

41. The medium of claim 40, wherein the downstream position corresponds to a location of an actuator.

42. The medium of claim 37, further comprising instructions to:

judge, responsive to an analysis of the plurality of active frames, whether the object satisfies an inspection criterion; and signal a reject actuator when the object does not satisfy the inspection criterion.

43. The medium of claim 40, wherein the controller comprises a human-machine interface.

44. The medium of claim 37, wherein computing the mark count further comprises fitting a line to at least a portion of the plurality of location values and at least a portion of the plurality of capture counts.

45. The medium of claim 37, computing the mark count further comprises interpolating a pair of capture counts and a corresponding pair of location values.

46. The medium of claim 37, wherein computing the mark count further comprises extrapolating from the capture counts and the location values.

47. The medium of claim 37, further comprising instructions to receive a succession of frames, each frame of the succession of frames comprising an image of the two-dimensional field of view, such that the plurality of active frames comprises a subset of the succession of frames; and further comprising instructions to:

compute a plurality of object detection weights based on and corresponding respectively to the succession of frames, each object detection weight of the plurality of object detection weights comprising evidence that the object is located in the two-dimensional field of view for the corresponding frame; wherein the succession of frames comprise images recorded at least before and after the object is located in the two-dimensional field of view; and select as the plurality of active frames a portion of the succession of frames where the evidence is sufficient.

48. The medium of claim 37, wherein the received frames are obtained by an imager with a global shutter.

49. The medium of claim 37, wherein the plurality of location values are computed responsive to at least one locator, the locator having a search range and oriented so that the search range is substantially parallel to a direction of motion of the object.

* * * * *